US007994305B2

(12) United States Patent
Reich et al.

(10) Patent No.: US 7,994,305 B2
(45) Date of Patent: Aug. 9, 2011

(54) COMPOSITIONS AND METHODS FOR SIRNA INHIBITION OF ANGIOPOIETIN 1 AND 2 AND THEIR RECEPTOR TIE2

(75) Inventors: Samuel Jotham Reich, Bala Cynwyd, PA (US); Michael J. Tolentino, Villanova, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 504 days.

(21) Appl. No.: 10/827,759

(22) Filed: Apr. 19, 2004

(65) Prior Publication Data

US 2004/0248174 A1 Dec. 9, 2004

Related U.S. Application Data

(60) Provisional application No. 60/463,981, filed on Apr. 18, 2003.

(51) Int. Cl.
*C07H 21/04* (2006.01)
(52) U.S. Cl. .................... 536/24.5; 536/24.1; 536/24.31; 435/6; 435/325; 435/375; 514/44
(58) Field of Classification Search ........................ None
See application file for complete search history.

(56) References Cited

U.S. PATENT DOCUMENTS

| | | | |
|---|---|---|---|
| 6,121,000 A | 9/2000 | Wright et al. | |
| 6,177,401 B1 | 1/2001 | Ullrich et al. | |
| 6,506,559 B1 | 1/2003 | Fire et al. | |
| 2002/0086356 A1 | 7/2002 | Tuschl et al. | |
| 2002/0132788 A1 | 9/2002 | Lewis et al. | |
| 2002/0162126 A1 | 10/2002 | Beach et al. | |
| 2002/0173478 A1 | 11/2002 | Gewirtz | |
| 2003/0143732 A1* | 7/2003 | Fosnaugh et al. | 435/325 |
| 2004/0115640 A1* | 6/2004 | Myers et al. | 435/6 |
| 2004/0259247 A1* | 12/2004 | Tuschl et al. | 435/375 |
| 2005/0159380 A1 | 7/2005 | Guerciolini et al. | |
| 2005/0197315 A1* | 9/2005 | Taira et al. | 514/44 |
| 2005/0246794 A1* | 11/2005 | Khvorova et al. | 800/286 |

FOREIGN PATENT DOCUMENTS

| | | | |
|---|---|---|---|
| CA | 2359180 | | 8/2000 |
| WO | WO 01/57206 A2 | | 8/2001 |
| WO | WO 01/68836 A2 | | 9/2001 |
| WO | WO 01/75164 A2 | | 10/2001 |
| WO | WO 02/44321 | * | 6/2002 |
| WO | WO 02/44321 A2 | | 6/2002 |
| WO | WO03/099298 A1 | | 12/2003 |
| WO | WO 2004/094606 A2 | | 11/2004 |

OTHER PUBLICATIONS

Ward et al. Genomic structre of the human angiopoietins show polymorphsm in angiopoietin-2. Cytogenetic and Genome Research 2001, Vo. 94: 147-154.*
Bass et al. The Short Answer. Nature 2001, vol. 41: 428-429. Macmillan Magazines Ltd.*
Hammond et al. Post-transcriptional gene silenceing by double-stranded RNA. Nature Reviews Genetics 2001, vol. 2: 110-119.*
Bartz et al. Production of High-Titer Human Immunodeficiency Virus Type 1 Pseudotyped with vesicular stomatitis virus glyoprotein. Methos to Enzymology 1997, vol. 12: 237-342. Academic Press.*
Scherer et al. Approaches for the Sequence-specific knockdown of mRNA (Nat. Biotechnol., 2003, 21(12), pp. 1457-1465).*
Mahato et al. Modulation of gene expression by antisense and antigene oligodeoxynucleotides and small interfering RNA. Expert Opin. Deliv. 2005, vol. 2(1): 3-28.*
Zhang et al. (Current Pharmaceutical Biotechnology 2004, vol. 5, p. 1-7).*
Vickers et al., Efficient reduction of target RNAs by small interfering RNA and RNase H-dependent antisense agents: A comparative analysis, 2003, J. Biol. Chem., Amer. Soc. Biolochemical Biologists. 278(9):7108-7118.
Shim et al., Inhibition of Angiopoietin-1 Expression in Tumor Cells by an Antisense RNA Approach Inhibited Xenograft Tumor Growth in Immunodeficient Mice, 2001, Int. J. Canc 94:6-15.
Hammond et al., Post-Transcriptional Gene Silencing by Double-Stranded RNA, 2001, Nature Reviews: Genetics 2:110-119.
Schroder et al., A single-stranded promoter for RNA polymerase III, 2003, PNAS 100(3):934-939.
White et al. "Inhibition of Rat Corneal Angiogenesis by a Nuclease-Resistant RNA Aptamer Specific for Angiopoietin-2" PNAS, Apr. 2003, 100(9):5028-5033.
Hayes et al. "Angiopoietin-1 and its Receptor Tie-2 Participate in the Regulation of Capillary-like Tubule Formation and Survival of Endothelial Cells" Microvacular Research, 1999, 58:224-237.
Miyagishi et al. "U6 Promoter-driven siRNAs with Four Uridine 3' Overhangs Efficiently Suppress Targeted Gene Expression in Mammalian Cells" Nature Biotechnology, May 2002, 19:497-500.
Bennett et al., *Hum Gene Ther* 10:1763-1769 (abstract) (Sep. 1996).
Elbashir et al., *Nature*, 411:494-498 (May 24, 2001).
Elbashir et al., *Genes&Development* 15:188-200 (2001).
Erickson, D., "RNAi Revs Up", Start-Up(A#2002900168) pp. 1-12 (Oct. 2002).
Fire et al., *Nature*, 391:806-811 (Feb. 19, 1998).
Holash et al., *PNAS*, 99(17):11393-11398 (Aug. 20, 2002).
Kim et al., *PNAS*, 99(17):11399-11404. (Aug. 20, 2002).
Novina et al., *Nature Medicine*, 8(7):81-686 (Jul. 2002).
Tischer et al., *J. Biol Chem* 266:11947-11954 (abstract) (Jun. 25, 1991).
Tuschl, T., The siRNA user guide (revised Oct. 11, 2002), Accessed from http://www.mpibpc.gwdg.de/abteilungen/100/105/sirna.html. on Nov. 1, 2002.

(Continued)

*Primary Examiner* — Kimberly Chong
(74) *Attorney, Agent, or Firm* — Pepper Hamilton LLP

(57) ABSTRACT

RNA interference using small interfering RNAs which are specific for mRNA produced from the Ang1, Ang2 or Tie2 genes inhibits expression of these genes. Diseases which involve Ang1, Ang2 or Tie2 mediated angiogenesis, such as inflammatory and autoimmune diseases, diabetic retinopathy, age related macular degeneration and many types of cancer, can be treated by administering the small interfering RNAs.

59 Claims, 4 Drawing Sheets

OTHER PUBLICATIONS

Tuschl, T., *Nat. Biotech* 20: 446-448 (May 2002).
Van Brunt, J., *Signals Magazine*: "Buzz—Shoot the Messenger" Aug. 22, 2002, Accessed from http://www.signalsmag.com/signalsmag . . . /3DF5AEF6049CC81C99256C1D0055BAA on Oct. 28, 2002.

Wu et al., *Mol Cell Biol*, vol. 22:22: 7758-7768 (abstract) (Nov. 2002).
Xia et al., *Nature Biotechnology*, vol. 20:1006-1010 (Oct. 2002).

* cited by examiner

SEQUENCE LISTING

<160> NUMBER OF SEQ ID NOS: 736

<210> SEQ ID NO 1
<211> LENGTH: 1493
<212> TYPE: DNA
<213> ORGANISM: Homo sapiens

<400> SEQUENCE: 1

```
atgacagttt tcctttcctt tgctttcctc gctgccattc tgactcacat agggtgcagc      60
aatcagcgcc gaagtccaga aaacagtggg agaagatata accggattca acatgggcaa     120
tgtgcctaca ctttcattct tccagaacac gatggcaact gtcgtgagag tacgacagac     180
cagtacaaca caaacgctct gcagagagat gctccacacg tggaaccgga tttctcttcc     240
cagaaacttc aacatctgga acatgtgatg gaaaattata ctcagtggct gcaaaaactt     300
gagaattaca ttgtggaaaa catgaagtcg gagatggccc agatacagca gaatgcagtt     360
cagaaccaca cggctaccat gctggagata ggaaccagcc tcctctctca gactgcagag     420
cagaccagaa agctgacaga tgttgagacc caggtactaa atcaaacttc tcgacttgag     480
atacagctgc tggagaattc attatccacc tacaagctag agaagcaact tcttcaacag     540
acaaatgaaa tcttgaagat ccatgaaaaa aacagtttat tagaacataa aatcttagaa     600
atggaaggaa aacacaagga agagttggac accttaaagg aagagaaaga gaaccttcaa     660
ggcttggtta ctcgtcaaac atatataatc caggagctgg aaaagcaatt aaacagagct     720
accaccaaca acagtgtcct tcagaagcag caactggagc tgatggacac agtccacaac     780
cttgtcaatc tttgcactaa gaagttttac taaagggagg aaaaagagag gaagagaaac     840
catttagaga ctgtgcagat gtatatcaag ctggttttaa taaagtgga atctacacta     900
tttatattaa taatatgcca gaacccaaaa aggtgttttg caatatggat gtcaatgggg     960
gaggttggac tgtaatacaa catcgtgaag atggaagtct agatttccaa agaggctgga    1020
aggaatataa aatgggtttt ggaaatccct ccggtgaata ttggctgggg aatgagttta    1080
tttttgccat taccagtcag aggcagtaca tgctaagaat tgagttaatg gactgggaag    1140
ggaaccgagc ctattcacag tatgacagat tccacatagg aaatgaaaag caaaactata    1200
ggttgtattt aaaaggtcac actgggacag caggaaaaca gagcagcctg atcttacacg    1260
gtgctgattt cagcactaaa gatgctgata atgacaactg tatgtgcaaa tgtgccctca    1320
tgttaacagg aggatggtgg tttgatgctt gtggcccctc aatctaaat ggaatgttct    1380
atactgcggg acaaaaccat ggaaactga atgggataaa gtggcactac ttcaagggc     1440
ccagttactc cttacgttcc acaactatga tgattcgacc tttagatttt tga           1493
```

<210> SEQ ID NO 2

<211> LENGTH: 2269
<212> TYPE: DNA
<213> ORGANISM: Homo sapiens
<220> FEATURE:
<223> OTHER INFORMATION: target sequence
<223> OTHER INFORMATION: target sequence

<400> SEQUENCE: 2

| | | | | | |
|---|---|---|---|---|---|
| tgggttggtg | tttatctcct | cccagccttg | agggagggaa | caacactgta | ggatctgggg | 60 |
| agagaggaac | aaaggaccgt | gaaagctgct | ctgtaaaagc | tgacacagcc | ctcccaagtg | 120 |
| agcaggactg | ttcttcccac | tgcaatctga | cagtttactg | catgcctgga | gagaacacag | 180 |
| cagtaaaaac | caggtttgct | actggaaaaa | gaggaaagag | aagactttca | ttgacggacc | 240 |
| cagccatggc | agcgtagcag | ccctgcgttt | cagacggcag | cagctcggga | ctctggacgt | 300 |
| gtgtttgccc | tcaagtttgc | taagctgctg | gtttattact | gaagaaagaa | tgtggcagat | 360 |
| tgttttcttt | actctgagct | gtgatcttgt | cttggccgca | gcctataaca | actttcggaa | 420 |
| gagcatggac | agcataggaa | agaagcaata | tcaggtccag | catgggtcct | gcagctacac | 480 |
| tttcctcctg | ccagagatgg | acaactgccg | ctcttcctcc | agccctacg | tgtccaatgc | 540 |
| tgtgcagagg | gacgcgccgc | tcgaatacga | tgactcggtg | cagaggctgc | aagtgctgga | 600 |
| gaacatcatg | gaaacaaca | ctcagtggct | aatgaagctt | gagaattata | tccaggacaa | 660 |
| catgaagaaa | gaaatggtag | agatacagca | gaatgcagta | cagaaccaga | cggctgtgat | 720 |
| gatagaaata | gggacaaacc | tgttgaacca | aacagctgag | caaacgcgga | agttaactga | 780 |
| tgtggaagcc | caagtattaa | atcagaccac | gagacttgaa | cttcagctct | tggaacactc | 840 |
| cctctcgaca | aacaaattgg | aaaaacagat | tttggaccag | accagtgaaa | taaacaaatt | 900 |
| gcaagataag | aacagtttcc | tagaaaagaa | ggtgctagct | atggaagaca | agcacatcat | 960 |
| ccaactacag | tcaataaaag | aagagaaaga | tcagctacag | gtgttagtat | ccaagcaaaa | 1020 |
| ttccatcatt | gaagaactag | aaaaaaaaat | agtgactgcc | acggtgaata | attcagttct | 1080 |
| tcaaaagcag | caacatgatc | tcatggagac | agttaataac | ttactgacta | tgatgtccac | 1140 |
| atcaaactca | gctaaggacc | ccactgttgc | taaagaagaa | caaatcagct | tcagagactg | 1200 |
| tgctgaagta | ttcaaatcag | gacacaccac | aaatggcatc | tacacgttaa | cattccctaa | 1260 |
| ttctacagaa | gagatcaagg | cctactgtga | catggaagct | ggaggaggcg | ggtgacaat | 1320 |
| tattcagcga | cgtgaggatg | gcagcgttga | ttttcagagg | acttggaaag | aatataaagt | 1380 |
| gggatttggt | aacccttcag | gagaatattg | gctgggaaat | gagtttgttt | cgcaactgac | 1440 |
| taatcagcaa | cgctatgtgc | ttaaaataca | ccttaaagac | tgggaaggga | atgaggctta | 1500 |
| ctcattgtat | gaacatttct | atctctcaag | tgaagaactc | aattatagga | ttcaccttaa | 1560 |
| aggacttaca | gggacagccg | gcaaaataag | cagcatcagc | caaccaggaa | atgattttag | 1620 |
| cacaaaggat | ggagacaacg | acaaatgtat | ttgcaaatgt | tcacaaatgc | taacaggagg | 1680 |
| ctggtggttt | gatgcatgtg | gtccttccaa | cttgaacgga | atgtactatc | cacagaggca | 1740 |
| gaacacaaat | aagttcaacg | gcattaaatg | gtactactgg | aaaggctcag | gctattcgct | 1800 |
| caaggccaca | accatgatga | tccgaccagc | agatttctaa | acatcccagt | ccacctgagg | 1860 |
| aactgtctcg | aactattttc | aaagacttaa | gcccagtgca | ctgaaagtca | cggctgcgca | 1920 |
| ctgtgtcctc | ttccaccaca | gagggcgtgt | gctcggtgct | gacgggaccc | acatgctcca | 1980 |
| gattagagcc | tgtaaacttt | atcacttaaa | cttgcatcac | ttaacggacc | aaagcaagac | 2040 |
| cctaaacatc | cataattgtg | attagacaga | acacctatgc | aaagatgaac | ccgaggctga | 2100 |
| gaatcagact | gacagtttac | agacgctgct | gtcacaacca | agaatgttat | gtgcaagttt | 2160 |

| | |
|---|---|
| atcagtaaat aactggaaaa cagaacactt atgttataca atacagatca tcttggaact | 2220 |
| gcattcttct gagcactgtt tatacactgt gtaaataccc atatgtcct | 2269 |

<210> SEQ ID NO 3
<211> LENGTH: 4138
<212> TYPE: DNA
<213> ORGANISM: Homo sapiens

<400> SEQUENCE: 3

| | |
|---|---|
| cttctgtgct gttccttctt gcctctaact tgtaaacaag acgtactagg acgatgctaa | 60 |
| tggaaagtca caaccgctg ggttttgaa aggatccttg ggacctcatg cacatttgtg | 120 |
| gaaactggat ggagagattt ggggaagcat ggactcttta gccagcttag ttctctgtgg | 180 |
| agtcagcttg ctcctttctg gaactgtgga aggtgccatg gacttgatct tgatcaattc | 240 |
| cctacctctt gtatctgatg ctgaaacatc tctcacctgc attgcctctg gtggcgccc | 300 |
| ccatgagccc atcaccatag aagggactt tgaagcctta atgaaccagc caggatcc | 360 |
| gctggaagtt actcaagatg tgaccagaga atgggctaaa aaagttgttt ggaagagaga | 420 |
| aaaggctagt aagatcaatg tgcttatttt ctgtgaaggg cgagttcgag agaggcaat | 480 |
| caggatacga accatgaaga tgcgtcaaca agcttccttc ctaccagcta ctttaactat | 540 |
| gactgtggac aagggagata cgtgaacat atctttcaaa aaggtattga ttaaagaaga | 600 |
| agatgcagtg atttacaaaa atggttcctt catccattca gtgccccggc atgaagtacc | 660 |
| tgatattcta gaagtacacc tgcctcatgc tcagccccag gatgctggag tgtactcggc | 720 |
| caggtatata ggaggaaacc tcttcacctc ggccttcacc aggctgatag tccggagatg | 780 |
| tgaagcccag aagtggggac ctgaatgcaa ccatctctgt actgcttgta tgaacaatgg | 840 |
| tgtctgccat gaagatactg gagaatgcat ttgccctcct gggtttatgg aaggacgtg | 900 |
| tgagaaggct tgtgaactgc acacgtttgg cagaacttgt aaagaaaggt gcagtggaca | 960 |
| agagggatgc aagtcttatg tgttctgtct ccctgacccc tatgggtgtt cctgtgccac | 1020 |
| aggctggaag ggtctgcagt gcaatgaagc atgccaccct ggttttttacg ggccagattg | 1080 |
| taagcttagg tgcagctgca acaatgggga gatgtgtgat cgcttccaag gatgtctctg | 1140 |
| ctctccagga tggcaggggc tccagtgtga gagagaaggc ataccgagga tgaccccaaa | 1200 |
| gatagtggat ttgccagatc atatagaagt aaacagtggt aaatttaatc ccatttgcaa | 1260 |
| agcttctggc tggccgctac ctactaatga agaaatgacc ctggtgaagc cggatgggac | 1320 |
| agtgctccat ccaaaagact ttaaccatac ggatcatttc tcagtagcca tattcaccat | 1380 |
| ccaccggatc ctccccctg actcaggagt ttgggtctgc agtgtgaaca cagtggctgg | 1440 |
| gatggtggaa aagcccttca acatttctgt taaagttctt ccaaagcccc tgaatgcccc | 1500 |
| aaacgtgatt gacactggac ataactttgc tgtcatcaac atcagctctg agccttactt | 1560 |
| tggggatgga ccaatcaaat ccaagaagct tctatacaaa cccgttaatc actatgaggc | 1620 |
| ttggcaacat attcaagtga caatgagat tgttacactc aactatttgg aacctcggac | 1680 |
| agaatatgaa ctctgtgtgc aactggtccg tcgtggagag ggtggggaag gcatcctgg | 1740 |
| acctgtgaga cgcttcacaa cagcttctat cggactccct cctccaagag gtctaaatct | 1800 |
| cctgcctaaa agtcagacca ctctaaattt gacctggcaa ccaatatttc caagctcgga | 1860 |
| agatgacttt tatgttgaag tggagagaag gtctgtgcaa aaaagtgatc agcagaatat | 1920 |
| taaagttcca ggcaacttga cttcggtgct acttaacaac ttcatcccca gggagcagta | 1980 |
| cgtggtccga gctagagtca acaccaaggc ccaggggaa tggagtgaag atctcactgc | 2040 |

```
ttggacccttagtgacattcttcctcctcaaccagaaaacatcaagatttccaacattac       2100
acactcctcggctgtgatttcttggacaatattggatggctattctatttcttctattac       2160
tatccgttacaaggttcaaggcaagaatgaagaccagcacgttgatgtgaagataaagaa       2220
tgccaccatcattcagtatcagctcaagggcctagagcctgaaacagcataccaggtgga       2280
cattttgcagagaacaacatagggtcaagcaacccagccttttctcatgaactggtgac        2340
cctcccagaatctcaagcaccagcggacctcggagggggaagatgctgcttatagccat       2400
ccttggctctgctggaatgacctgcctgactgtgctgttggcctttctgatcatattgca      2460
attgaagaggcaaatgtgcaaaggagaatggcccaagccttccaaaacgtgagggaaga       2520
accagctgtgcagttcaactcagggactctggccctaaacaggaaggtcaaaacaaccc       2580
agatcctacaatttatccagtgcttgactggaatgacatcaaatttcaagatgtgattgg     2640
ggagggcaattttggccaagttcttaaggcgcgcatcaagaaggatgggtacgatgga       2700
tgctgccatcaaaagaatgaaagaatatgcctccaaagatgatcacagggactttgcagg     2760
agaactggaagttctttgtaaacttggacaccatccaaacatcatcaatctcttaggagc      2820
atgtgaacatcgaggctactgtacctggccattgagtacgcgccccatgaaaccttct       2880
ggacttccttcgcaagagccgtgtgctggacggacccagcatttgccattgccaatag        2940
caccgcgtccacactgtcctcccagcagctccttcacttcgctgccgacgtggcccgggg     3000
catggactacttgagccaaaacagtttatccacagggatctggctgccagaaacatttt     3060
agttggtgaaactatgtggcaaaaatagcagattttggattgtcccgaggtcaagaggt    3120
gtacgtgaaaaagacaatggaaggctcccagtgcgctggatggccatcgagtcactgaa    3180
ttacagtgtgtacacaaccaacagtgatgtatggtcctatggtgtgttactatgggagat     3240
tgttagcttaggaggcacaccctactgcggatgacttgtgcagaactctacgagaagct       3300
gccccagggctacagactggagaagcccctgaactgtgatgatgaggtgtatgatctaat     3360
gagacaatgctggcgggagaagccttatgagaggccatcatttgcccagatattggtgtc     3420
cttaaacagaatgttagagggcgaaagactacgtgaataccacgctttatgagaagtt     3480
tacttatgcaggaattgactgttctgctgaagaagcggcctaggacagaacatctgtata     3540
ccctctgttccctttcactggcatgggagacccttgacaactgctgagaaacatgcct       3600
ctgccaaaggatgtgatataaagtgtacatatgtgctggaattctaacaagtcataggt       3660
taatatttaagacactgaaaaatcaagtgatataaatcagattcttctctctcattttta       3720
tccctcacctgtagcatgccagtcccgtttcatttagtcatgtgaccactctgtcttgtg      3780
tttccacagctgcaagttcagtccaggatgctaacatctaaaaatagacttaaatctca      3840
ttgcttacaagcctaagaatctttagagaagtatacataagtttaggataaataatggg      3900
atttctttttcttttctctggtaatattgacttgtatattttaagaaataacagaaagcc      3960
tgggtgacattgggagacatgtgacatttatatattgaattaatatccctacatgtatt      4020
gcacattgtaaaaagttttagttttgatgagttgtgagttaccttgtatactgtaggca      4080
cactttgcactgatatatcatgagtgaataatgtcttgcctactcaaaaaaaaaaa         4138
```

<210> SEQ ID NO 4  
<211> LENGTH: 159  
<212> TYPE: DNA  
<213> ORGANISM: Canis familiaris

<400> SEQUENCE: 4

```
aggaggaagtctagatttcaagaggttggaaagaatataaatggtttggaaatcc          60
```

| | |
|---|---|
| ctctggtgaa tattggctgg ggaatgagtt tattttttgcc attaccagtc agaggcagta | 120 |
| cacactaaga attgagttaa tggactggga aggaaaccc | 159 |

<210> SEQ ID NO 5
<211> LENGTH: 2424
<212> TYPE: DNA
<213> ORGANISM: Mus musculus
<220> FEATURE:
<221> NAME/KEY: misc_feature
<222> LOCATION: 2308
<223> OTHER INFORMATION: n = a, g, c or t

<400> SEQUENCE: 5

| | |
|---|---|
| ggctgctcct tcctctcagg acagctccga gtgtgccggg gagaagagaa gagaagagac | 60 |
| aggcactggg aaagagcctg ctgcgggacg gagaaggctc tcactgatgg acttattcac | 120 |
| acggcacagc cctgtgcctt agacagcagc tgagagctca ggacgcaagt ttgctgaact | 180 |
| cacagtttag aacccaaaaa gagagagaga atgtggcaga tcattttcct aacttttggc | 240 |
| tgggatcttg tcttggcctc agcctacagt aactttagga agagcgtgga cagcacaggc | 300 |
| agaaggcagt accaggtcca gaacggaccc tgcagctaca cgttcctgct gccggagacc | 360 |
| gacagctgcc gatcttcctc cagcccctac atgtccaatg ccgtgcagag ggatgcaccc | 420 |
| ctcgactacg acgactcagt gcaaaggctg caggtgctgg agaacattct agagaacaac | 480 |
| acacagtggc tgatgaagct ggagaattac attcaggaca catgaagaa ggagatggtg | 540 |
| gagatccaac agaatgtggt gcagaaccag acagctgtga tgatagagat tggaaccagc | 600 |
| ttgctgaacc agacagcagc acaaactcgg aaactgactg atgtggaagc ccaagtacta | 660 |
| aaccagacga caagactcga gctgcagctt ctccaacatt ctatttctac caacaaattg | 720 |
| gaaaagcaga ttttggatca gaccagtgaa ataaacaagc tacaaaataa gaacagcttc | 780 |
| ctagaacaga aagttctgga catggagggc aagcacagcg agcagctaca gtccatgaag | 840 |
| gagcagaagg acgagctcca ggtgctggtg tccaagcaga gctctgtcat tgacgagctg | 900 |
| gagaagaagc tggtgacagc cacggtcaac aactcgctcc ttcagaagca gcagcatgac | 960 |
| ctaatggaga ccgtcaacag cttgctgacc atgatgtcat cacccaactc caagagctcg | 1020 |
| gttgctatcc gtaaagaaga gcaaaccacc ttcagagact gtgcggaaat cttcaagtca | 1080 |
| ggactcacca ccagtggcat ctacacactg accttcccca actccacaga ggagatcaag | 1140 |
| gcctactgtg acatggacgt gggtggagga ggtggacag tcatccaaca ccgagaagat | 1200 |
| ggcagtgtgg acttccagag gacgtggaaa gaatacaaag agggcttcgg gaaccctctg | 1260 |
| ggagagtact ggctgggcaa tgagtttgtc tcccagctga ccggtcagca ccgctacgtg | 1320 |
| cttaagatcc agctgaagga ctgggaaggc aacgaggcgc attcgctgta tgatcacttc | 1380 |
| tacctcgctg gtgaagagtc caactacagg attcaccta caggactcac ggggaccgcg | 1440 |
| gccaaaataa gtagcatcag ccaaccagga agtgattta gcacaaagga ttcggacaat | 1500 |
| gacaaatgca tctgcaagtg ttcccagatg ctctcaggag gctggtggtt tgacgcatgt | 1560 |
| ggtccttcca acttgaatgg acagtactac ccacaaaaac agaatacaaa taagtttaac | 1620 |
| ggtatcaagt ggtactactg gaaggggtcc ggctactcgc tcaaggccac aaccatgatg | 1680 |
| atccggccag cagatttcta aatgcctgcc tacactacca gaagaacttg ctgcatccaa | 1740 |
| agattaactc caaggcactg agagacacca gtgcatagca gccccttccc acatcaggaa | 1800 |
| gtgctcctgg gggtggggag ggtctgtgtg taccagactg aagcgcatca cttaagcctg | 1860 |
| caccgctaac caaccaaagg cactgcagtc tggagaaaca cttctgggaa ggttgtggct | 1920 |

-continued

```
gaggatcaga aggacagcgt gcagactctg tcacaaggaa gaatgttccg tgggagttca    1980
gcagtaaata actggaaaac agaacactta gatggtgcag ataaatcttg ggaccacatt    2040
cctctaagca cggttttctag agtgaataca ttcacagctc ggctgtcaca atgacaaggc    2100
cgtgtcctcg cactgtggca gccagtatcc agggacttct aagtggtggg cacaggctat    2160
catctggaga agcacacatt cattgttttc ctcttgggtg cttaacatgt tcatttgaaa    2220
acaacacatt tacctatctt gatggcttag ttttttaatgg ctggctacta tttactatat    2280
ggcaaaaatg cccacatctc tggaatancc accaaataag cgccatgttg gtgaatgcgg    2340
aggctgtact attttgtttt cttcctggct ggtaaatatg aaggtatttt tagtaattaa    2400
atataagtta ttagttgaaa gacc                                           2424
```

<210> SEQ ID NO 6
<211> LENGTH: 4676
<212> TYPE: DNA
<213> ORGANISM: Mus musculus

<400> SEQUENCE: 6

```
ccacgcgtcc gagcaggagc cggagcagga gcagaagata agccttggat gaagggcaag      60
atggataggg ctcgctctgc cccaagccct gctgatacca agtgccttta agatacagcc     120
tttcccatcc taatctgcaa aggaaacagg aaaaaggaac ttaaccctcc ctgtgctcag     180
acagaaatga gactgttacc gcctgcttct gtggtgtttc tccttgccgc caacttgtaa     240
acaagagcga gtgaccatg cgagcgggaa gtcgcaaagt tgtgagttgt tgaaagcttc     300
ccagggactc atgctcatct gtggacgctg gatggggaga tctggggaag tatggactct     360
ttagccggct tagttctctg tggagtcagc ttgctccttt atggagtagt agaaggtgcc     420
atggacctga tcttgatcaa ttccctacct cttgtgtctg atgccgaaac atccctcacc     480
tgcattgcct ctgggtggca cccccatgag cccatcacca taggaaggga ctttgaagcc     540
ttaatgaacc agcaccaaga tccactggag gttactcaag atgtgaccag agaatgggcg     600
aaaaaagttg tttggaagag agaaaaggcc agtaagatta atggtgctta tttctgtgaa     660
ggtcgagttc gaggacaggc tataaggata cggaccatga agatgcgtca acaagcgtcc     720
ttcctacctg ctactttaac tatgaccgtg gacaggggag ataatgtgaa catatctttc     780
aaaaaggtgt taattaaaga agaagatgca gtgatttaca aaaatggctc ccttcatcca     840
ctcagtgccc ccggcatgaa gtaccttgat attttagaag ttcacttgcc gcatgctcag     900
ccccaggatg ctggtgtgta ctcggccagg tacataggag gaaacctgtt cacctcagcc     960
ttcaccaggc tgattgttcg gagatgtgaa gctcagaagt gggggcccga ctgtagccgt    1020
ccttgtacta cttgcaagaa caatggagtc tgccatgaag ataccgggga atgcatttgc    1080
cctcctgggt ttatggggag aacatgtgag aaagcttgtg agccgcacac atttggcagg    1140
acctgtaaag aaaggtgtag tggaccagaa ggatgcaagt cttatgtgtt ctgtctccca    1200
gaccccttacg ggtgttcctg tgccacaggc tggaggggggt tgcagtgcaa tgaagcatgc    1260
ccatctggtt actacggacc agactgtaag ctcaggtgcc actgtaccaa tgaagagata    1320
tgtgatcggt tccaaggatg cctctgctct caaggatggc aagggctgca gtgtgagaaa    1380
gaaggcaggc caaggatgac tccacagata gaggatttgc cagatcacat tgaagtaaac    1440
agtggaaaat ttaaccccat ctgcaaagcc tctgggtggc cactacctac tagtgaagaa    1500
atgccctag tgaagccaga tgggacagtg ctccaaccaa atgacttcaa ctatacagat    1560
cgtttctcag tggccatatt cactgtcaac cgagtcttac ctcctgactc aggagtctgg    1620
```

```
gtctgcagtg tgaacacagt ggctgggatg gtggaaaagc ctttcaacat ttccgtcaaa    1680
gttcttccag agcccctgca cgccccaaat gtgattgaca ctggacataa ctttgctatc    1740
atcaatatca gctctgagcc ttactttggg gatggaccca tcaaatccaa gaagcttttc    1800
tataaacctg tcaatcaggc ctggaaatac attgaagtga cgaatgagat tttcactctc    1860
aactacttgg agccgcggac tgactacgag ctgtgtgtgc agctggcccg tcctggagag    1920
ggtggagaag ggcatcctgg gcctgtgaga cgatttacaa cagcgtctat cggactccct    1980
cctccaagag gtctcagtct cctgccaaaa agccagacag ctctaaattt gacttggcaa    2040
ccgatattta caaactcaga agatgaattt tatgtggaag tcgagaggcg atccctgcaa    2100
acaacaagtg atcagcagaa catcaaagtc cctgggaacc tgacctcggt gctactgagc    2160
aacttagtcc ccagggagca gtacacagtc cgagctagag tcaacaccaa ggcgcagggg    2220
gagtggagtg aagaactcag ggcctggacc cttagtgaca ttctccctcc tcaaccagaa    2280
aacatcaaga tctccaacat cactgactcc acagctatgt tttcttggac aatagtggat    2340
ggctattcga tttcttccat catcatccgg tataaggttc agggcaaaaa tgaagaccag    2400
cacattgatg tgaagatcaa gaatgctacc gttactcagt accagctcaa gggcctagag    2460
ccagagacta cataccatgt ggatattttt gctgagaaca acataggatc aagcaaccca    2520
gccttttctc atgaactgag gacgcttcca cattccccag cctctgcaga cctcggaggg    2580
gggaaagatg ctactcatag ccatccttgg gtcggctgga atgactttgc atcaccgtgc    2640
ttgttggcgt ttctgattat gttgcaactg aagagagcaa atgtccaaag gagaatggct    2700
caggcattcc agaacgtgag agaagaacca gctgtgcagt ttaactcagg aactctggcc    2760
cttaacagga aggccaaaaa caatccggat cccacaattt atcctgtgct tgactggaat    2820
gacatcaagt ttcaagacgt gatcggagag ggcaactttg gccaggttct gaaggcacgc    2880
atcaagaagg atgggttacg gatggatgcc gccatcaaga ggatgaaaga gtatgcctcc    2940
aaagatgatc acagggactt cgcaggagaa ctggaggttc tttgtaaact tggacaccat    3000
ccaaacatca tcaatctctt gggagcatgt gaacaccgag gctatttgta cctagctatt    3060
gagtatgccc cgcatggaaa cctcctggac ttcctgggta agagcagagt gctagagaca    3120
gaccctgctt tttgccatcg ccaacagtac agttccacac tgtcctccca acagcttctt    3180
cattttgctg cagatgtggc ccgggggatg gactacttga gccagaaaca gtttatccac    3240
agggacctgg ctgccagaaa cattttagtt ggtgaaaact acatagccaa aatagcagat    3300
tttggattgt cacgaggtca agaagtgtat gtgaaaaaga caatgggaag gctcccagtg    3360
cgttggatgg caatcgaatc actgaactat agtgtctata caaccaacag tgatgtctgg    3420
tcctatggtg tattgctctg ggagattgtt agcttaggag gcaccccta ctgcggcatg    3480 acgtgcgcgg agctctatga gaagctaccc cagggctaca ggctggagaa gcccctgaac    3540
tgtgatgatg aggtgtatga tctaatgaga cagtgctgga gggagaagcc ttatgagaga    3600
ccatcatttg cccagatatt ggtgtcctta aacaggatgc tggaagaacg gaagacatac    3660
gtgaacacca cactgtatga aagtttacc tatgcaggaa ttgactgccc tgcggaagaa    3720
gcagcctaga gcagaactct tcatgtacaa cggccatttc tcctcactgg cgcgagacct    3780
ttgtacacct gtaccaagca agccaccac tgccaagaga tgtgatatat aagtttatat    3840
attgtgctgt gtttgggacc ctcctcatac agttcgtgcg gatctgcagt gtgttctgac    3900
tctaatgtga ctgtatatac tgctcggagt aagaatgtgc taagatcaga atgcctgtcc    3960
gtggtttcat ctaatatatt ttcctaaaag catagattgc acaggaaggt atgagtacaa    4020
```

```
atactgtaat gcataacttg ttattgtcct agatgtgttt gatattttcg ctttacaact    4080
gaatgctata aaagtgtttt gctgtgtaca cataagatac tgttcgttaa aataagcatt    4140
cccttgacag cacaggaaga aaagcgaggg aaatgtatgg attatattaa atgtgggtta    4200
ctacacaaga ggccgaacat tccaagtagc agaagagagg gtctctcaac tctgctcctc    4260
acctgcagaa gccagtttgt ttggccatgt gacaattgtc ctgtgttttt atagcaccca    4320
aatcattcta aaatatgaac atctaaaaac tttgctagga gactaagaac ctttggagag    4380
atagatataa gtacggtcaa aaaacaaaac tgcgggactt acatttattt tctatagtaa    4440
tctgttgtac attttaagga ggtaaactag gatttaggag tgatgtgtga catttctgcc    4500
atggagttac catccccaca tgtatcacat actgcatatt cccacatgta tcacacatgt    4560
attgtaaaat tttgtagttt tgatcacttg tgaatttact gttgatgtgg tagccacctg    4620
ctgcaatggt tcctcttgta ggtgaataaa tgtcttgtct acccacaaaa aaaaaa       4676
```

```
<210> SEQ ID NO 7
<211> LENGTH: 2135
<212> TYPE: DNA
<213> ORGANISM: Rattus norvegicus

<400> SEQUENCE: 7
```

```
agcccctgca tgcccaaat gttattgaca ctggacacaa ctttgctatc atcaacatca      60
gctctgagcc ttactttggg gatggaccga tcaaatccaa gaagctcttc tataaacctg    120
tcaatcaggc ttggaaatac attcaagtga tgaatgagat tgtcacactc aactacctgg    180
agcctcggac tgactacgag ctgtgtgtac agctggtccg tcctggagag ggtggagaag    240
gacatcctgg acctgtgaga agattcacaa cagcgtctat cggactccct cctccaagag    300
gtctcagtct cctacccaaa agccagacag ctctgaattt gacttggcaa ccgatattta    360
caagctcaga agatgaattt tatgtggaag ttgagaggtg gtcccagcaa acaagaagtg    420
atcagcagaa catcaaagtg cctgggaacc tgacttccgt gctgctgaac aacttactcc    480
ccagggagca gtacagcgtc cgagctagag tcaacaccaa ggcccagggg gagtggagtg    540
aagaactcag ggcctggacc cttagtgaca aaaacatcaa gatcaccaac atcactgatt    600
acacagctct ggtttcttgg acaatcgtgg acggctattc gatttcttcc atcatcatcc    660
ggtataaggt tcagggcaaa aatgaagacc agcacattga cgtgaagatc aagaatgcca    720
ccatcactca ataccagctc aagggcctag agccagagac tacataccat gtggatattt    780
ttgctgagaa caacatagga tcaagcaacc cagccttttc ccaagaaatt aggacacttc    840
cagcccctaa agaccttgga ggggaaaga tgctacttat agccattctt gggtcggctg    900
gaatgacttg catcaccgtg ctattggcgt ttctgattat gttgcaactg aagagagcaa    960
atgtccaaag aagaatggcc caggccttcc agaacgtgag agaagaacca gctgttcagt   1020
tcaactcagg aactctggcc ctaaacagga aggccaaaaa caatccggat cccacaattt   1080
atcctgtgct tgactggaat gacatcaagt tccagatgt gattggagag ggcaactttg   1140
gccaggttct gaaggcgcgc atcaagaagg atgggttacg gatggacgct gccatcaaga   1200
ggatgaaagg tttggaggac agcatttgct ggggtgggga gacaccgctt cctgttgaaa   1260
tcttccgttt gtggcatat attcttcaaa ccagatgtga agaagcaaca ttacaactct   1320 tggccttct tccagaatat gcctccaaag atgatcacag ggactttgca ggagaactgg   1380
aggttctttg taaacttgga caccatccga acatcattaa tctcttggga gcatgtgaac   1440
acagaggcta cttataccctg gctattgagt atgccccaca tggaaacctc ctggactttc   1500
```

```
tgcgtaagag ccgagtgcta gagacagacc ctgcctttgc catcgccaac agcacggctt    1560
ccacactgtc ctcccagcag cttcttcatt ttgctgcaga tgtggcccgg gggatggact    1620
acttgagcca aaacagtttt atccacaggg acctggctgc cagaaacatt ttagttggcg    1680
aaaactacat agccaaaata gcagattttg gattgtcacg aggtcaagaa gtgtatgtga    1740
aaaagacaat gggaaggctc ccagtgcgct ggatggcaat tgagtctctg aactatagtg    1800
tctatacaac caacagtgat gtatggtcct atggtgtatt gctctgggag atcgttagct    1860
taggaggcac tccatactgc ggcatgacat gtgcagaact ctatgagaag ctgccccagg    1920
gctacagatt ggagaagccc ctgaactgtg atgatgaggt gtatgatcta atgagacaat    1980
gctggaggga gaagccttat gagagaccat catttgccca gatattggtg tccttaaaca    2040
gaatgctgga agaacgaaag acatacgtga acaccacact ttatgagaag tttacctacg    2100
caggaattga ctgttctgct gaagaagcag cctag                              2135
```

<210> SEQ ID NO 8
<211> LENGTH: 1497
<212> TYPE: DNA
<213> ORGANISM: Homo sapiens

<400> SEQUENCE: 8

```
atgacagttt ccctttcctt tgctttcctc gctgccattc tgactcacat agggtgcagc      60
aatcagcgcc gaagtccaga aaacagtggg agaagatata accggattca acatgggcaa    120
tgtgcctaca ctttcattct tccagaacac gatggcaact gtcgtgagag tacgacagac    180
cagtacaaca caaacgctct gcagagagat gctccacacg tggaaccgga tttctcttcc    240
cagaaacttc aacatctgga acatgtgatg gaaaattata ctcagtggct gcaaaaactt    300
gagaattaca ttgtggaaaa catgaagtcg gagatggccc agatacagca gaatgcagtt    360
cagaaccaca cggctaccat gctggagata ggaaccagcc tcctctctca gactgcagag    420
cagaccagaa agctgacaga tgttgagacc caggtactaa atcaaacttc tcgacttgag    480
atacagctgc tggagaattc attatccacc tacaagctag agaagcaact tcttcaacag    540
acaaatgaaa tcttgaagat ccatgaaaaa aacagtttat tagaacataa atcttagaa    600 atggaaggaa acacaaagga agagttggac accttaaagg aagagaaaga gaaccttcaa    660
ggcttggtta ctcgtcaaac atatataatc caggagctgg aaaagcaatt aaacagagct    720
accaccaaca cagtgtcct tcagaagcag caactggagc tgatggacac agtccacaac    780
cttgtcaatc tttgcactaa agaaggtgtt ttactaaagg aggaaaaag agaggaagag    840 aaaccattta gagactgtgc agatgtatat caagctggtt ttaataaaag tggaatctac    900
actatttata ttaataatat gccagaaccc aaaaaggtgt tttgcaatat ggatgtcaat    960
gggggagggt tggactgtaa tacaacatcgt gaagatggaa gtctagattt ccaaagaggc   1020
tggaaggaat ataaaatggg ttttggaaat ccctccggtg aatattggct ggggaatgag   1080 tttattttg ccattaccag tcagaggcag tacatgctaa gaattgagtt aatggactgg   1140
gaagggaacc gagcctattc acagtatgac agattccaca taggaaatga aaagcaaaac   1200
tataggttgt atttaaaagg tcacactggg acagcaggaa acagagcag cctgatctta   1260 cacggtgctg atttcagcac taaagatgct gataatgaca actgtatgtg caaatgtgcc   1320
ctcatgttaa caggaggatg gtggtttgat gcttgtggcc cctccaatct aaatggaatg   1380
ttctatactg cgggacaaaa ccatggaaaa ctgaatggga taaagtggca ctacttcaaa   1440
gggcccagtt actccttacg ttccacaact atgatgattc gaccttaaga tttttga      1497
```

<210> SEQ ID NO 9
<211> LENGTH: 1376
<212> TYPE: DNA
<213> ORGANISM: Homo sapiens

<400> SEQUENCE: 9

```
ggtttattac tgaagaaaga atgtggcaga ttgttttctt tactctgagc tgtgatcttg      60
tcttggccgc agcctataac aactttcgga agagcatgga cagcatagga aagaagcaat     120
atcaggtcca gcatgggtcc tgcagctaca ctttcctcct gccagagatg gacaactgcc     180
gctcttcctc cagcccctac gtgtccaatg ctgtgcagag ggacgcgccg ctcgaatacg     240
atgactcggt gcagaggctg caagtgctgg agaacatcat ggaaaacaac actcagtggc     300
taatgaaggt attaaatcag accacgagac ttgaacttca gctcttggaa cactccctct     360
cgacaaacaa attggaaaaa cagattttgg accagaccag tgaaataaac aaattgcaag     420
ataagaacag tttcctagaa aagaaggtgc tagctatgga agacaagcac atcatccaac     480
tacagtcaat aaaagaagag aaagatcagc tacaggtgtt agtatccaag caaaattcca     540
tcattgaaga actagaaaaa aaaatagtga ctgccacggt gaataattca gttcttcaaa     600
agcagcaaca tgatctcatg gagacagtta ataacttact gactatgatg tccacatcaa     660
actcagctaa ggaccccact gttgctaaag aagaacaaat cagcttcaga gactgtgctg     720
aagtattcaa atcaggacac accacaaatg gcatctacac gttaacattc cctaattcta     780
cagaagagat caaggcctac tgtgacatgg aagctggagg aggcgggtgg acaattattc     840
agcgacgtga ggatggcagc gttgattttc agaggacttg gaaagaatat aaagtgggat     900
ttggtaaccc ttcaggagaa tattggctgg gaaatgagtt tgtttcgcaa ctgactaatc     960
agcaacgcta tgtgcttaaa atacacctta agactgggaa agggaatgag gcttactcat    1020
tgtatgaaca tttctatctc tcaagtgaag aactcaatta taggattcac cttaaaggac    1080
ttacagggac agccggcaaa ataagcagca tcagccaacc aggaaatgat tttagcacaa    1140
aggatggaga caacgacaaa tgtatttgca atgttcaca aatgctaaca ggaggctggt    1200
ggtttgatgc atgtggtcct tccaacttga acggaatgta ctatccacag aggcagaaca    1260
caaataagtt caacggcatt aaatggtact actggaaagg ctcaggctat tcgctcaagg    1320
ccacaaccat gatgatccga ccagcagatt tctaaacatc ccagtccacc tgagga        1376
```

<210> SEQ ID NO 10
<211> LENGTH: 2578
<212> TYPE: DNA
<213> ORGANISM: Homo sapiens

<400> SEQUENCE: 10

```
acatttgtgg aaactggatg gagagatttg gggaagcatg gactctttag ccagcttggt      60
tctctgtgga gtcagcttgc tccttctgga aactgtggaa ggtgccatgg actctttagc     120
cagcttagtt ctctgtggag tcagcttgct ccttctgga actgtggaag gtgccatgga     180
cttgatcttg atcaattccc tacctcttgt atctgatgct gaaacatctc tcacctgcat     240
tgcctctggg tggcgccccc atgagcccat caccatagga agggactttg aagccttaat     300
gaaccagcac caggatccgc tggaagttac tcaagatgtg accagagaat gggctaaaaa     360
agttgtttgg aagagagaaa aggctagtaa gatcaatggt gcttatttct gtgaagggcg     420
agttcgagga gaggcaatca ggatacgaac catgaagatg cgtcaacaag cttccttcct     480
accagctact ttaactatga ctgtggacaa gggagataac gtgaacatat ctttcaaaaa     540
```

```
ggtattgatt aaagaagaag atgcagtgat ttacaaaaat ggttccttca tccattcagt      600
gccccggcat gaagtacctg atattctaga agtacacctg cctcatgctc agccccagga      660
tgctggagtg tactcggcca ggtatatagg aggaaacctc ttcacctcgg ccttcaccag      720
gctgatagtc cggagatgtg aagcccagaa gtggggacct gaatgcaacc atctctgtac      780
tgcttgtatg aacaatggtg tctgccatga agatactgga gaatgcattt gccctcctgg      840
gtttatggga aggacgtgtg agaaggcttg tgaactgcac acgtttggca gaacttgtaa      900
agaaaggtgc agtggacaag agggatgcaa gtcttatgtg ttctgtctcc ctgaccccta      960
tgggtgttcc tgtgccacag gctggaaggg tctgcagtgc aatgaaggca taccgaggat     1020
gaccccaaag atagtggatt tgccagatca tatagaagta acagtggta aatttaatcc      1080 catttgcaaa gcttctggct ggccgctacc tactaatgaa gaaatgaccc tggtgaagcc     1140
ggatgggaca gtgctccatc caaaagactt taaccatacg gatcatttct cagtagccat     1200
attcaccatc caccggatcc tccccctga ctcaggagtt tgggtctgca gtgtgaacac      1260
agtggctggg atggtggaaa agcccttcaa catttctgtt aaagttcttc caaagcccct     1320
gaatgcccca acgtgattg acactggaca taactttgct gtcatcaaca tcagctctga      1380
gccttacttt ggggatggac caatcaaatc caagaagctt ctatacaaac ccgttaatca     1440
ctatgaggct tggcaacata ttcaagtgac aaatgagatt gttacactca actatttgga     1500
acctcggaca gaatatgaac tctgtgtgca actggtccgt cgtggagagg gtggggaagg     1560
gcatcctgga cctgtgagac gcttcacaac agcttctatc ggactccctc ctccaagagg     1620
tctaaatctc ctgcctaaaa gtcagaccac tctaaatttg acctggcaac aatatttcc      1680 aagctcggaa gatgactttt atgttgaagt ggagagaagg tctgtgcaaa aaagtgatca     1740
gcagaatatt aaagttccag gcaacttgac ttcggtgcta cttaacaact acatcccag      1800 ggagcagtac gtggtccgag ctagagtcaa caccaaggcc caggggaat ggagtgaaga      1860 tctcactgct tggacccta gtgacattct tcctcctcaa ccagaaaaca tcaagatttc     1920
caacattaca cactcctcgg ctgtgatttc ttggacaata ttggatggct attctatttc     1980
ttctattact atccgttaca aggttcaagg caagaatgaa gaccagcacg ttgatgtgaa     2040
gataaagaat gccaccatca ttcagtatca gctcaagggc ctagagcctg aaacagcata     2100
ccaggtggac atttttgcag agaacaacat agggtcaagc aacccagcct tttctcatga     2160
actggtgacc ctcccagaat ctcaagcacc agcggacctc ggaggggga agatgctgct     2220 tatagccatc cttggctctg ctggaatgac ctgcctgact gtgctgttgg cctttctgat     2280
catattgcaa ttgaagaggg caaatgtgca aaggagaatg gcccaagcct tccaaaacgt     2340
gagggaagaa ccagctgtgc agttcaactc agggactctg gccctaaaca ggaaggtcaa     2400
aaacaaccca gatcctacaa tttatccagt gcttgactgg aatgacatca aatttcaaga     2460
tgtgattggg gagggcaatt ttggccaagt tcttaaggcg cgcatcaaga aggatgggtt     2520
acggatggat gctgccatca aaagaatgaa agaatatgcc tccaaagatg atcacagg       2578
```

<210> SEQ ID NO 11
<211> LENGTH: 984
<212> TYPE: DNA
<213> ORGANISM: Homo sapiens

<400> SEQUENCE: 11

```
atgaagaaac atcatcatca tcatcatggc aaaaacaacc cagatcctac aatttatcca       60
gtgcttgact ggaatgacat caaatttcaa gatgtgattg gggagggcaa ttttggccaa      120
```

```
gttcttaagg cgcgcatcaa gaaggatggg ttacggatgg atgctgccat caaaagaatg    180
aaagaatatg cctccaaaga tgatcacagg gactttgcag gagaactgga agttctttgt    240
aaacttggac accatccaaa catcatcaat ctcttaggag catgtgaaca tcgaggcttc    300
ttgtacctgg ccattgagta cgcgccccat ggaaaccttc tggacttcct tcgcaagagc    360
cgtgtgctgg agacggaccc agcatttgcc attgccaata gcaccgcgtc cacactgtcc    420
tcccagcagc tccttcactt cgctgccgac gtggcccggg gcatggacta cttgagccaa    480
aaacagttta tccacaggga tctggctgcc agaaacattt tagttggtga aaactatgtg    540
gcaaaaatag cagattttgg attgtcccga ggtcaagagg tgtatgtgaa aaagacaatg    600
ggaaggctcc cagtgcgctg gatggccatc gagtcactga attacagtgt gtacacaacc    660
aacagtgatg tatggtccta tggtgtgtta ctatgggaga ttgttagctt aggaggcaca    720
ccctactgcg gaatgacttg tgcagaactc ttcgagaagc tgccccaggg ctacagactg    780
gagaagcccc tgaactgtga tgatgaggtg tatgatctaa tgagacaatg ctggcgggag    840
aagccttatg agaggccatc atttgcccag atattggtgt ccttaaacag aatgttagag    900
gagcgaaaga cctacgtgaa taccacgctt tatgagaagt ttacttatgc aggaattgac    960
tgtgctgctg aagaagcggc ctag                                            984

<210> SEQ ID NO 12
<211> LENGTH: 21
<212> TYPE: DNA
<213> ORGANISM: Artificial Sequence
<220> FEATURE:
<223> OTHER INFORMATION: Ang2 target sequence

<400> SEQUENCE: 12
aatgctgtgc agagggacgc g                                               21

<210> SEQ ID NO 13
<211> LENGTH: 21
<212> TYPE: RNA
<213> ORGANISM: Artificial Sequence
<220> FEATURE:
<223> OTHER INFORMATION: Ang2 siRNA sense strand

<400> SEQUENCE: 13
ugcugugcag agggacgcgu u                                               21

<210> SEQ ID NO 14
<211> LENGTH: 21
<212> TYPE: RNA
<213> ORGANISM: Artificial Sequence
<220> FEATURE:
<223> OTHER INFORMATION: Ang2 siRNA antisense strand

<400> SEQUENCE: 14
uuacgacacg ucucccugcg c                                               21

<210> SEQ ID NO 15
<211> LENGTH: 21
<212> TYPE: DNA
<213> ORGANISM: Artificial Sequence
<220> FEATURE:
<223> OTHER INFORMATION: Ang2 siRNA sense strand
<220> FEATURE:
<221> NAME/KEY: misc_feature
<222> LOCATION: (20)...(21)
<223> OTHER INFORMATION: deoxyribonucleotides

<400> SEQUENCE: 15
```

```
ugcugugcag agggacgcgt t                                              21
```

<210> SEQ ID NO 16
<211> LENGTH: 21
<212> TYPE: DNA
<213> ORGANISM: Artificial Sequence
<220> FEATURE:
<223> OTHER INFORMATION: Ang2 siRNA antisense strand
<220> FEATURE:
<221> NAME/KEY: misc_feature
<222> LOCATION: (20)...(21)
<223> OTHER INFORMATION: deoxyribonucleotides

<400> SEQUENCE: 16

```
ttacgacacg ucucccugcg c                                              21
```

<210> SEQ ID NO 17
<211> LENGTH: 21
<212> TYPE: DNA
<213> ORGANISM: Artificial Sequence
<220> FEATURE:
<223> OTHER INFORMATION: Ang2 target sequence

<400> SEQUENCE: 17

```
ttacgacacg ucucccugcg c                                              21
```

<210> SEQ ID NO 18
<211> LENGTH: 21
<212> TYPE: RNA
<213> ORGANISM: Artificial Sequence
<220> FEATURE:
<223> OTHER INFORMATION: Ang2 siRNA sense strand

<400> SEQUENCE: 18

```
guauuaaauc agaccacgau u                                              21
```

<210> SEQ ID NO 19
<211> LENGTH: 21
<212> TYPE: RNA
<213> ORGANISM: Artificial Sequence
<220> FEATURE:
<223> OTHER INFORMATION: Ang2 siRNA antisense strand

<400> SEQUENCE: 19

```
ucguggucug auuuaauacu u                                              21
```

<210> SEQ ID NO 20
<211> LENGTH: 21
<212> TYPE: DNA
<213> ORGANISM: Artificial Sequence
<220> FEATURE:
<223> OTHER INFORMATION: Ang2 siRNA sense strand
<220> FEATURE:
<221> NAME/KEY: misc_feature
<222> LOCATION: (20)...(21)
<223> OTHER INFORMATION: deoxyribonucleotides

<400> SEQUENCE: 20

```
guauuaaauc agaccacgat t                                              21
```

<210> SEQ ID NO 21
<211> LENGTH: 21
<212> TYPE: DNA
<213> ORGANISM: Artificial Sequence
<220> FEATURE:
<223> OTHER INFORMATION: Ang2 siRNA antisense strand
<220> FEATURE:
<221> NAME/KEY: misc_feature

```
<222> LOCATION: (20)...(21)
<223> OTHER INFORMATION: deoxyribonucleotides

<400> SEQUENCE: 21
ucguggucug auuuaauact t                                              21

<210> SEQ ID NO 22
<211> LENGTH: 21
<212> TYPE: DNA
<213> ORGANISM: Artificial Sequence
<220> FEATURE:
<223> OTHER INFORMATION: Ang1 target sequence

<400> SEQUENCE: 22
aatgcagttc agaaccacac g                                              21

<210> SEQ ID NO 23
<211> LENGTH: 21
<212> TYPE: RNA
<213> ORGANISM: Artificial Sequence
<220> FEATURE:
<223> OTHER INFORMATION: Ang1siRNA sense strand

<400> SEQUENCE: 23
ugcaguucag aaccacacgu u                                              21

<210> SEQ ID NO 24
<211> LENGTH: 21
<212> TYPE: RNA
<213> ORGANISM: Artificial Sequence
<220> FEATURE:
<223> OTHER INFORMATION: Ang1 siRNA antisense strand

<400> SEQUENCE: 24
uuacgucaag ucuuggugug c                                              21

<210> SEQ ID NO 25
<211> LENGTH: 21
<212> TYPE: DNA
<213> ORGANISM: Artificial Sequence
<220> FEATURE:
<223> OTHER INFORMATION: Ang1 siRNA sense strand
<220> FEATURE:
<221> NAME/KEY: misc_feature
<222> LOCATION: (20)...(21)
<223> OTHER INFORMATION: deoxyribonucleotides

<400> SEQUENCE: 25
ugcaguucag aaccacacgt t                                              21

<210> SEQ ID NO 26
<211> LENGTH: 21
<212> TYPE: DNA
<213> ORGANISM: Artificial Sequence
<220> FEATURE:
<223> OTHER INFORMATION: Ang1 siRNA antisense strand
<220> FEATURE:
<221> NAME/KEY: misc_feature
<222> LOCATION: (20)...(21)
<223> OTHER INFORMATION: deoxyribonucleotides

<400> SEQUENCE: 26
cgugugguuc ugaacugcat t                                              21

<210> SEQ ID NO 27
<211> LENGTH: 21
<212> TYPE: DNA
<213> ORGANISM: Artificial Sequence
```

```
<220> FEATURE:
<223> OTHER INFORMATION: Ang1 target sequence

<400> SEQUENCE: 27
cuucucgacu ugagauacau u                                              21

<210> SEQ ID NO 28
<211> LENGTH: 21
<212> TYPE: RNA
<213> ORGANISM: Artificial Sequence
<220> FEATURE:
<223> OTHER INFORMATION: Ang1 siRNA sense strand

<400> SEQUENCE: 28
cuucucgacu ugagauacau u                                              21

<210> SEQ ID NO 29
<211> LENGTH: 21
<212> TYPE: RNA
<213> ORGANISM: Artificial Sequence
<220> FEATURE:
<223> OTHER INFORMATION: Ang1 siRNA antisense strand

<400> SEQUENCE: 29
uguaucucaa gucgagaagu u                                              21

<210> SEQ ID NO 30
<211> LENGTH: 21
<212> TYPE: DNA
<213> ORGANISM: Artificial Sequence
<220> FEATURE:
<223> OTHER INFORMATION: Ang1 siRNA sense strand
<220> FEATURE:
<221> NAME/KEY: misc_feature
<222> LOCATION: (20)...(21)
<223> OTHER INFORMATION: deoxyribonucleotides

<400> SEQUENCE: 30
cuucucgacu ugagauacat t                                              21

<210> SEQ ID NO 31
<211> LENGTH: 21
<212> TYPE: DNA
<213> ORGANISM: Artificial Sequence
<220> FEATURE:
<223> OTHER INFORMATION: Ang1 siRNA antisense strand

<400> SEQUENCE: 31
uguaucucaa gucgagaagt t                                              21

<210> SEQ ID NO 32
<211> LENGTH: 21
<212> TYPE: DNA
<213> ORGANISM: Artificial Sequence
<220> FEATURE:
<223> OTHER INFORMATION: target sequence

<400> SEQUENCE: 32
aatcagcgcc gaagtccaga a                                              21

<210> SEQ ID NO 33
<211> LENGTH: 21
<212> TYPE: DNA
<213> ORGANISM: Artificial Sequence
<220> FEATURE:
<223> OTHER INFORMATION: target sequence

<400> SEQUENCE: 33
```
aagtccagaa aacagtggga g                                              21

<210> SEQ ID NO 34
<211> LENGTH: 21
<212> TYPE: DNA
<213> ORGANISM: Artificial Sequence
<220> FEATURE:
<223> OTHER INFORMATION: target sequence

<400> SEQUENCE: 34
aaaacagtgg gagaagatat a                                              21

<210> SEQ ID NO 35
<211> LENGTH: 21
<212> TYPE: DNA
<213> ORGANISM: Artificial Sequence
<220> FEATURE:
<223> OTHER INFORMATION: target sequence

<400> SEQUENCE: 35
aaacagtggg agaagatata a                                              21

<210> SEQ ID NO 36
<211> LENGTH: 21
<212> TYPE: DNA
<213> ORGANISM: Artificial Sequence
<220> FEATURE:
<223> OTHER INFORMATION: target sequence

<400> SEQUENCE: 36
aacagtggga gaagatataa c                                              21

<210> SEQ ID NO 37
<211> LENGTH: 21
<212> TYPE: DNA
<213> ORGANISM: Artificial Sequence
<220> FEATURE:
<223> OTHER INFORMATION: target sequence

<400> SEQUENCE: 37
aagatataac cggattcaac a                                              21

<210> SEQ ID NO 38
<211> LENGTH: 21
<212> TYPE: DNA
<213> ORGANISM: Artificial Sequence
<220> FEATURE:
<223> OTHER INFORMATION: target sequence

<400> SEQUENCE: 38
aaccggattc aacatgggca a                                              21

<210> SEQ ID NO 39
<211> LENGTH: 21
<212> TYPE: DNA
<213> ORGANISM: Artificial Sequence
<220> FEATURE:
<223> OTHER INFORMATION: target sequence

<400> SEQUENCE: 39
aacatgggca atgtgcctac a                                              21

<210> SEQ ID NO 40
<211> LENGTH: 21
<212> TYPE: DNA
<213> ORGANISM: Artificial Sequence

```
<220> FEATURE:
<223> OTHER INFORMATION: target sequence

<400> SEQUENCE: 40
aatgtgccta cactttcatt c                                              21

<210> SEQ ID NO 41
<211> LENGTH: 21
<212> TYPE: DNA
<213> ORGANISM: Artificial Sequence
<220> FEATURE:
<223> OTHER INFORMATION: target sequence

<400> SEQUENCE: 41
aacacgatgg caactgtcgt g                                              21

<210> SEQ ID NO 42
<211> LENGTH: 21
<212> TYPE: DNA
<213> ORGANISM: Artificial Sequence
<220> FEATURE:
<223> OTHER INFORMATION: target sequence

<400> SEQUENCE: 42
aactgtcgtg agagtacgac a                                              21

<210> SEQ ID NO 43
<211> LENGTH: 21
<212> TYPE: DNA
<213> ORGANISM: Artificial Sequence
<220> FEATURE:
<223> OTHER INFORMATION: target sequence

<400> SEQUENCE: 43
aacacaaacg ctctgcagag a                                              21

<210> SEQ ID NO 44
<211> LENGTH: 21
<212> TYPE: DNA
<213> ORGANISM: Artificial Sequence
<220> FEATURE:
<223> OTHER INFORMATION: target sequence

<400> SEQUENCE: 44
aaacgctctg cagagagatg c                                              21

<210> SEQ ID NO 45
<211> LENGTH: 21
<212> TYPE: DNA
<213> ORGANISM: Artificial Sequence
<220> FEATURE:
<223> OTHER INFORMATION: target sequence

<400> SEQUENCE: 45
aacgctctgc agagagatgc t                                              21

<210> SEQ ID NO 46
<211> LENGTH: 21
<212> TYPE: DNA
<213> ORGANISM: Artificial Sequence
<220> FEATURE:
<223> OTHER INFORMATION: target sequence

<400> SEQUENCE: 46
aaccggattt ctcttcccag a                                              21
```

```
<210> SEQ ID NO 47
<211> LENGTH: 21
<212> TYPE: DNA
<213> ORGANISM: Artificial Sequence
<220> FEATURE:
<223> OTHER INFORMATION: target sequence

<400> SEQUENCE: 47
aaacttcaac atctggaaca t                                             21

<210> SEQ ID NO 48
<211> LENGTH: 21
<212> TYPE: DNA
<213> ORGANISM: Artificial Sequence
<220> FEATURE:
<223> OTHER INFORMATION: target sequence

<400> SEQUENCE: 48
aacttcaaca tctggaacat g                                             21

<210> SEQ ID NO 49
<211> LENGTH: 21
<212> TYPE: DNA
<213> ORGANISM: Artificial Sequence
<220> FEATURE:
<223> OTHER INFORMATION: target sequence

<400> SEQUENCE: 49
aacatctgga acatgtgatg g                                             21

<210> SEQ ID NO 50
<211> LENGTH: 21
<212> TYPE: DNA
<213> ORGANISM: Artificial Sequence
<220> FEATURE:
<223> OTHER INFORMATION: target sequence

<400> SEQUENCE: 50
aacatgtgat ggaaaattat a                                             21

<210> SEQ ID NO 51
<211> LENGTH: 21
<212> TYPE: DNA
<213> ORGANISM: Artificial Sequence
<220> FEATURE:
<223> OTHER INFORMATION: target sequence

<400> SEQUENCE: 51
aaaattatac tcagtggctg c                                             21

<210> SEQ ID NO 52
<211> LENGTH: 21
<212> TYPE: DNA
<213> ORGANISM: Artificial Sequence
<220> FEATURE:
<223> OTHER INFORMATION: target sequence

<400> SEQUENCE: 52
aaattatact cagtggctgc a                                             21

<210> SEQ ID NO 53
<211> LENGTH: 21
<212> TYPE: DNA
<213> ORGANISM: Artificial Sequence
<220> FEATURE:
<223> OTHER INFORMATION: target sequence

<400> SEQUENCE: 53
```
aattatactc agtggctgca a                                              21

<210> SEQ ID NO 54
<211> LENGTH: 21
<212> TYPE: DNA
<213> ORGANISM: Artificial Sequence
<220> FEATURE:
<223> OTHER INFORMATION: target sequence

<400> SEQUENCE: 54
aaaaacttga gaattacatt g                                              21

<210> SEQ ID NO 55
<211> LENGTH: 21
<212> TYPE: DNA
<213> ORGANISM: Artificial Sequence
<220> FEATURE:
<223> OTHER INFORMATION: target sequence

<400> SEQUENCE: 55
aaaacttgag aattacattg t                                              21

<210> SEQ ID NO 56
<211> LENGTH: 21
<212> TYPE: DNA
<213> ORGANISM: Artificial Sequence
<220> FEATURE:
<223> OTHER INFORMATION: target sequence

<400> SEQUENCE: 56
aaacttgaga attacattgt g                                              21

<210> SEQ ID NO 57
<211> LENGTH: 21
<212> TYPE: DNA
<213> ORGANISM: Artificial Sequence
<220> FEATURE:
<223> OTHER INFORMATION: target sequence

<400> SEQUENCE: 57
aacttgagaa ttacattgtg g                                              21

<210> SEQ ID NO 58
<211> LENGTH: 21
<212> TYPE: DNA
<213> ORGANISM: Artificial Sequence
<220> FEATURE:
<223> OTHER INFORMATION: target sequence

<400> SEQUENCE: 58
aattacattg tggaaaacat g                                              21

<210> SEQ ID NO 59
<211> LENGTH: 21
<212> TYPE: DNA
<213> ORGANISM: Artificial Sequence
<220> FEATURE:
<223> OTHER INFORMATION: target sequence

<400> SEQUENCE: 59
aaaacatgaa gtcggagatg g                                              21

<210> SEQ ID NO 60
<211> LENGTH: 21
<212> TYPE: DNA
<213> ORGANISM: Artificial Sequence

```
<220> FEATURE:
<223> OTHER INFORMATION: target sequence

<400> SEQUENCE: 60
aaacatgaag tcggagatgg c                                              21

<210> SEQ ID NO 61
<211> LENGTH: 21
<212> TYPE: DNA
<213> ORGANISM: Artificial Sequence
<220> FEATURE:
<223> OTHER INFORMATION: target sequence

<400> SEQUENCE: 61
aacatgaagt cggagatggc c                                              21

<210> SEQ ID NO 62
<211> LENGTH: 21
<212> TYPE: DNA
<213> ORGANISM: Artificial Sequence
<220> FEATURE:
<223> OTHER INFORMATION: target sequence

<400> SEQUENCE: 62
aagtcggaga tggcccagat a                                              21

<210> SEQ ID NO 63
<211> LENGTH: 21
<212> TYPE: DNA
<213> ORGANISM: Artificial Sequence
<220> FEATURE:
<223> OTHER INFORMATION: target sequence

<400> SEQUENCE: 63
aatgcagttc agaaccacac g                                              21

<210> SEQ ID NO 64
<211> LENGTH: 21
<212> TYPE: DNA
<213> ORGANISM: Artificial Sequence
<220> FEATURE:
<223> OTHER INFORMATION: target sequence

<400> SEQUENCE: 64
aaccacacgg ctaccatgct g                                              21

<210> SEQ ID NO 65
<211> LENGTH: 21
<212> TYPE: DNA
<213> ORGANISM: Artificial Sequence
<220> FEATURE:
<223> OTHER INFORMATION: target sequence

<400> SEQUENCE: 65
aaccagcctc ctctctcaga c                                              21

<210> SEQ ID NO 66
<211> LENGTH: 21
<212> TYPE: DNA
<213> ORGANISM: Artificial Sequence
<220> FEATURE:
<223> OTHER INFORMATION: target sequence

<400> SEQUENCE: 66
aaagctgaca gatgttgaga c                                              21
```

```
<210> SEQ ID NO 67
<211> LENGTH: 21
<212> TYPE: DNA
<213> ORGANISM: Artificial Sequence
<220> FEATURE:
<223> OTHER INFORMATION: target sequence

<400> SEQUENCE: 67
aagctgacag atgttgagac c                                              21

<210> SEQ ID NO 68
<211> LENGTH: 21
<212> TYPE: DNA
<213> ORGANISM: Artificial Sequence
<220> FEATURE:
<223> OTHER INFORMATION: target sequence

<400> SEQUENCE: 68
aaatcaaact tctcgacttg a                                              21

<210> SEQ ID NO 69
<211> LENGTH: 21
<212> TYPE: DNA
<213> ORGANISM: Artificial Sequence
<220> FEATURE:
<223> OTHER INFORMATION: target sequence

<400> SEQUENCE: 69
aatcaaactt ctcgacttga g                                              21

<210> SEQ ID NO 70
<211> LENGTH: 21
<212> TYPE: DNA
<213> ORGANISM: Artificial Sequence
<220> FEATURE:
<223> OTHER INFORMATION: target sequence

<400> SEQUENCE: 70
aaacttctcg acttgagata c                                              21

<210> SEQ ID NO 71
<211> LENGTH: 21
<212> TYPE: DNA
<213> ORGANISM: Artificial Sequence
<220> FEATURE:
<223> OTHER INFORMATION: target sequence

<400> SEQUENCE: 71
aacttctcga cttgagatac a                                              21

<210> SEQ ID NO 72
<211> LENGTH: 21
<212> TYPE: DNA
<213> ORGANISM: Artificial Sequence
<220> FEATURE:
<223> OTHER INFORMATION: target sequence

<400> SEQUENCE: 72
aattcattat ccacctacaa g                                              21

<210> SEQ ID NO 73
<211> LENGTH: 21
<212> TYPE: DNA
<213> ORGANISM: Artificial Sequence
<220> FEATURE:
<223> OTHER INFORMATION: target sequence

<400> SEQUENCE: 73
```
aagctagaga agcaacttct t         21

<210> SEQ ID NO 74
<211> LENGTH: 21
<212> TYPE: DNA
<213> ORGANISM: Artificial Sequence
<220> FEATURE:
<223> OTHER INFORMATION: target sequence

<400> SEQUENCE: 74
aagcaacttc ttcaacagac a         21

<210> SEQ ID NO 75
<211> LENGTH: 21
<212> TYPE: DNA
<213> ORGANISM: Artificial Sequence
<220> FEATURE:
<223> OTHER INFORMATION: target sequence

<400> SEQUENCE: 75
aacttcttca acagacaaat g         21

<210> SEQ ID NO 76
<211> LENGTH: 21
<212> TYPE: DNA
<213> ORGANISM: Artificial Sequence
<220> FEATURE:
<223> OTHER INFORMATION: target sequence

<400> SEQUENCE: 76
aacagacaaa tgaaatcttg a         21

<210> SEQ ID NO 77
<211> LENGTH: 21
<212> TYPE: DNA
<213> ORGANISM: Artificial Sequence
<220> FEATURE:
<223> OTHER INFORMATION: target sequence

<400> SEQUENCE: 77
aaatgaaatc ttgaagatcc a         21

<210> SEQ ID NO 78
<211> LENGTH: 21
<212> TYPE: DNA
<213> ORGANISM: Artificial Sequence
<220> FEATURE:
<223> OTHER INFORMATION: target sequence

<400> SEQUENCE: 78
aatgaaatct tgaagatcca t         21

<210> SEQ ID NO 79
<211> LENGTH: 20
<212> TYPE: DNA
<213> ORGANISM: Artificial Sequence
<220> FEATURE:
<223> OTHER INFORMATION: target sequence

<400> SEQUENCE: 79
aaatcttgaa gatccatgaa           20

<210> SEQ ID NO 80
<211> LENGTH: 21
<212> TYPE: DNA
<213> ORGANISM: Artificial Sequence

```
<220> FEATURE:
<223> OTHER INFORMATION: target sequence

<400> SEQUENCE: 80
aatcttgaag atccatgaaa a                                              21

<210> SEQ ID NO 81
<211> LENGTH: 21
<212> TYPE: DNA
<213> ORGANISM: Artificial Sequence
<220> FEATURE:
<223> OTHER INFORMATION: target sequence

<400> SEQUENCE: 81
aagatccatg aaaaaaacag t                                              21

<210> SEQ ID NO 82
<211> LENGTH: 21
<212> TYPE: DNA
<213> ORGANISM: Artificial Sequence
<220> FEATURE:
<223> OTHER INFORMATION: target sequence

<400> SEQUENCE: 82
aaaaaaacag tttattagaa c                                              21

<210> SEQ ID NO 83
<211> LENGTH: 21
<212> TYPE: DNA
<213> ORGANISM: Artificial Sequence
<220> FEATURE:
<223> OTHER INFORMATION: target sequence

<400> SEQUENCE: 83
aaaaaacagt ttattagaac a                                              21

<210> SEQ ID NO 84
<211> LENGTH: 21
<212> TYPE: DNA
<213> ORGANISM: Artificial Sequence
<220> FEATURE:
<223> OTHER INFORMATION: target sequence

<400> SEQUENCE: 84
aaaaacagtt tattagaaca t                                              21

<210> SEQ ID NO 85
<211> LENGTH: 21
<212> TYPE: DNA
<213> ORGANISM: Artificial Sequence
<220> FEATURE:
<223> OTHER INFORMATION: target sequence

<400> SEQUENCE: 85
aaaacagttt attagaacat a                                              21

<210> SEQ ID NO 86
<211> LENGTH: 21
<212> TYPE: DNA
<213> ORGANISM: Artificial Sequence
<220> FEATURE:
<223> OTHER INFORMATION: target sequence

<400> SEQUENCE: 86
aaacagttta ttagaacata a                                              21
```

```
<210> SEQ ID NO 87
<211> LENGTH: 21
<212> TYPE: DNA
<213> ORGANISM: Artificial Sequence
<220> FEATURE:
<223> OTHER INFORMATION: target sequence

<400> SEQUENCE: 87
aacagtttat tagaacataa a                                              21

<210> SEQ ID NO 88
<211> LENGTH: 21
<212> TYPE: DNA
<213> ORGANISM: Artificial Sequence
<220> FEATURE:
<223> OTHER INFORMATION: target sequence

<400> SEQUENCE: 88
aacataaaat cttagaaatg g                                              21

<210> SEQ ID NO 89
<211> LENGTH: 21
<212> TYPE: DNA
<213> ORGANISM: Artificial Sequence
<220> FEATURE:
<223> OTHER INFORMATION: target sequence

<400> SEQUENCE: 89
aaaatcttag aaatggaagg a                                              21

<210> SEQ ID NO 90
<211> LENGTH: 21
<212> TYPE: DNA
<213> ORGANISM: Artificial Sequence
<220> FEATURE:
<223> OTHER INFORMATION: target sequence

<400> SEQUENCE: 90
aaatcttaga aatggaagga a                                              21

<210> SEQ ID NO 91
<211> LENGTH: 21
<212> TYPE: DNA
<213> ORGANISM: Artificial Sequence
<220> FEATURE:
<223> OTHER INFORMATION: target sequence

<400> SEQUENCE: 91
aatcttagaa atggaaggaa a                                              21

<210> SEQ ID NO 92
<211> LENGTH: 21
<212> TYPE: DNA
<213> ORGANISM: Artificial Sequence
<220> FEATURE:
<223> OTHER INFORMATION: target sequence

<400> SEQUENCE: 92
aaatggaagg aaaacacaag g                                              21

<210> SEQ ID NO 93
<211> LENGTH: 21
<212> TYPE: DNA
<213> ORGANISM: Artificial Sequence
<220> FEATURE:
<223> OTHER INFORMATION: target sequence

<400> SEQUENCE: 93
```

```
aatggaagga aaacacaagg a                                              21

<210> SEQ ID NO 94
<211> LENGTH: 21
<212> TYPE: DNA
<213> ORGANISM: Artificial Sequence
<220> FEATURE:
<223> OTHER INFORMATION: target sequence

<400> SEQUENCE: 94
aaggaaaaca caaggaagag t                                              21

<210> SEQ ID NO 95
<211> LENGTH: 21
<212> TYPE: DNA
<213> ORGANISM: Artificial Sequence
<220> FEATURE:
<223> OTHER INFORMATION: target sequence

<400> SEQUENCE: 95
aaaacacaag gaagagttgg a                                              21

<210> SEQ ID NO 96
<211> LENGTH: 21
<212> TYPE: DNA
<213> ORGANISM: Artificial Sequence
<220> FEATURE:
<223> OTHER INFORMATION: target sequence

<400> SEQUENCE: 96
aaacacaagg aagagttgga c                                              21

<210> SEQ ID NO 97
<211> LENGTH: 21
<212> TYPE: DNA
<213> ORGANISM: Artificial Sequence
<220> FEATURE:
<223> OTHER INFORMATION: target sequence

<400> SEQUENCE: 97
aacacaagga agagttggac a                                              21

<210> SEQ ID NO 98
<211> LENGTH: 21
<212> TYPE: DNA
<213> ORGANISM: Artificial Sequence
<220> FEATURE:
<223> OTHER INFORMATION: target sequence

<400> SEQUENCE: 98
aaggaagagt tggacacctt a                                              21

<210> SEQ ID NO 99
<211> LENGTH: 21
<212> TYPE: DNA
<213> ORGANISM: Artificial Sequence
<220> FEATURE:
<223> OTHER INFORMATION: target sequence

<400> SEQUENCE: 99
aagagttgga caccttaaag g                                              21

<210> SEQ ID NO 100
<211> LENGTH: 21
<212> TYPE: DNA
<213> ORGANISM: Artificial Sequence
```

```
<220> FEATURE:
<223> OTHER INFORMATION: target sequence

<400> SEQUENCE: 100
aaaggaagag aaagagaacc t                                      21

<210> SEQ ID NO 101
<211> LENGTH: 21
<212> TYPE: DNA
<213> ORGANISM: Artificial Sequence
<220> FEATURE:
<223> OTHER INFORMATION: target sequence

<400> SEQUENCE: 101
aaggaagaga aagagaacct t                                      21

<210> SEQ ID NO 102
<211> LENGTH: 21
<212> TYPE: DNA
<213> ORGANISM: Artificial Sequence
<220> FEATURE:
<223> OTHER INFORMATION: target sequence

<400> SEQUENCE: 102
aagagaaaga gaaccttcaa g                                      21

<210> SEQ ID NO 103
<211> LENGTH: 21
<212> TYPE: DNA
<213> ORGANISM: Artificial Sequence
<220> FEATURE:
<223> OTHER INFORMATION: target sequence

<400> SEQUENCE: 103
aaagagaacc ttcaaggctt g                                      21

<210> SEQ ID NO 104
<211> LENGTH: 21
<212> TYPE: DNA
<213> ORGANISM: Artificial Sequence
<220> FEATURE:
<223> OTHER INFORMATION: target sequence

<400> SEQUENCE: 104
aagagaacct tcaaggcttg g                                      21

<210> SEQ ID NO 105
<211> LENGTH: 21
<212> TYPE: DNA
<213> ORGANISM: Artificial Sequence
<220> FEATURE:
<223> OTHER INFORMATION: target sequence

<400> SEQUENCE: 105
aaccttcaag gcttggttac t                                      21

<210> SEQ ID NO 106
<211> LENGTH: 21
<212> TYPE: DNA
<213> ORGANISM: Artificial Sequence
<220> FEATURE:
<223> OTHER INFORMATION: target sequence

<400> SEQUENCE: 106
aaggcttggt tactcgtcaa a                                      21
```

```
<210> SEQ ID NO 107
<211> LENGTH: 21
<212> TYPE: DNA
<213> ORGANISM: Artificial Sequence
<220> FEATURE:
<223> OTHER INFORMATION: target sequence

<400> SEQUENCE: 107
aaacatatat aatccaggag c                                              21

<210> SEQ ID NO 108
<211> LENGTH: 21
<212> TYPE: DNA
<213> ORGANISM: Artificial Sequence
<220> FEATURE:
<223> OTHER INFORMATION: target sequence

<400> SEQUENCE: 108
aacatatata atccaggagc t                                              21

<210> SEQ ID NO 109
<211> LENGTH: 21
<212> TYPE: DNA
<213> ORGANISM: Artificial Sequence
<220> FEATURE:
<223> OTHER INFORMATION: target sequence

<400> SEQUENCE: 109
aatccaggag ctggaaaagc a                                              21

<210> SEQ ID NO 110
<211> LENGTH: 21
<212> TYPE: DNA
<213> ORGANISM: Artificial Sequence
<220> FEATURE:
<223> OTHER INFORMATION: target sequence

<400> SEQUENCE: 110
aaaagcaatt aaacagagct a                                              21

<210> SEQ ID NO 111
<211> LENGTH: 21
<212> TYPE: DNA
<213> ORGANISM: Artificial Sequence
<220> FEATURE:
<223> OTHER INFORMATION: target sequence

<400> SEQUENCE: 111
aaagcaatta aacagagcta c                                              21

<210> SEQ ID NO 112
<211> LENGTH: 21
<212> TYPE: DNA
<213> ORGANISM: Artificial Sequence
<220> FEATURE:
<223> OTHER INFORMATION: target sequence

<400> SEQUENCE: 112
aagcaattaa acagagctac c                                              21

<210> SEQ ID NO 113
<211> LENGTH: 21
<212> TYPE: DNA
<213> ORGANISM: Artificial Sequence
<220> FEATURE:
<223> OTHER INFORMATION: target sequence

<400> SEQUENCE: 113
```
aattaaacag agctaccacc a                                       21

<210> SEQ ID NO 114
<211> LENGTH: 21
<212> TYPE: DNA
<213> ORGANISM: Artificial Sequence
<220> FEATURE:
<223> OTHER INFORMATION: target sequence

<400> SEQUENCE: 114
aaacagagct accaccaaca a                                       21

<210> SEQ ID NO 115
<211> LENGTH: 21
<212> TYPE: DNA
<213> ORGANISM: Artificial Sequence
<220> FEATURE:
<223> OTHER INFORMATION: target sequence

<400> SEQUENCE: 115
aacagagcta ccaccaacaa c                                       21

<210> SEQ ID NO 116
<211> LENGTH: 21
<212> TYPE: DNA
<213> ORGANISM: Artificial Sequence
<220> FEATURE:
<223> OTHER INFORMATION: target sequence

<400> SEQUENCE: 116
aacaacagtg tccttcagaa g                                       21

<210> SEQ ID NO 117
<211> LENGTH: 21
<212> TYPE: DNA
<213> ORGANISM: Artificial Sequence
<220> FEATURE:
<223> OTHER INFORMATION: target sequence

<400> SEQUENCE: 117
aacagtgtcc ttcagaagca g                                       21

<210> SEQ ID NO 118
<211> LENGTH: 21
<212> TYPE: DNA
<213> ORGANISM: Artificial Sequence
<220> FEATURE:
<223> OTHER INFORMATION: target sequence

<400> SEQUENCE: 118
aagcagcaac tggagctgat g                                       21

<210> SEQ ID NO 119
<211> LENGTH: 21
<212> TYPE: DNA
<213> ORGANISM: Artificial Sequence
<220> FEATURE:
<223> OTHER INFORMATION: target sequence

<400> SEQUENCE: 119
aactggagct gatggacaca g                                       21

<210> SEQ ID NO 120
<211> LENGTH: 21
<212> TYPE: DNA
<213> ORGANISM: Artificial Sequence

```
<220> FEATURE:
<223> OTHER INFORMATION: target sequence

<400> SEQUENCE: 120
aaccttgtca atctttgcac t                                              21

<210> SEQ ID NO 121
<211> LENGTH: 21
<212> TYPE: DNA
<213> ORGANISM: Artificial Sequence
<220> FEATURE:
<223> OTHER INFORMATION: target sequence

<400> SEQUENCE: 121
aatctttgca ctaaagaagg t                                              21

<210> SEQ ID NO 122
<211> LENGTH: 21
<212> TYPE: DNA
<213> ORGANISM: Artificial Sequence
<220> FEATURE:
<223> OTHER INFORMATION: target sequence

<400> SEQUENCE: 122
aaagaaggtg ttttactaaa g                                              21

<210> SEQ ID NO 123
<211> LENGTH: 21
<212> TYPE: DNA
<213> ORGANISM: Artificial Sequence
<220> FEATURE:
<223> OTHER INFORMATION: target sequence

<400> SEQUENCE: 123
aagaaggtgt tttactaaag g                                              21

<210> SEQ ID NO 124
<211> LENGTH: 21
<212> TYPE: DNA
<213> ORGANISM: Artificial Sequence
<220> FEATURE:
<223> OTHER INFORMATION: target sequence

<400> SEQUENCE: 124
aaggtgtttt actaaaggga g                                              21

<210> SEQ ID NO 125
<211> LENGTH: 21
<212> TYPE: DNA
<213> ORGANISM: Artificial Sequence
<220> FEATURE:
<223> OTHER INFORMATION: target sequence

<400> SEQUENCE: 125
aaagggagga aaaagagagg a                                              21

<210> SEQ ID NO 126
<211> LENGTH: 21
<212> TYPE: DNA
<213> ORGANISM: Artificial Sequence
<220> FEATURE:
<223> OTHER INFORMATION: target sequence

<400> SEQUENCE: 126
aagggaggaa aaagagagga a                                              21
```

-continued

<210> SEQ ID NO 127
<211> LENGTH: 21
<212> TYPE: DNA
<213> ORGANISM: Artificial Sequence
<220> FEATURE:
<223> OTHER INFORMATION: target sequence

<400> SEQUENCE: 127
aaaaagagag gaagagaaac c                                    21

<210> SEQ ID NO 128
<211> LENGTH: 21
<212> TYPE: DNA
<213> ORGANISM: Artificial Sequence
<220> FEATURE:
<223> OTHER INFORMATION: target sequence

<400> SEQUENCE: 128
aaaagagagg aagagaaacc a                                    21

<210> SEQ ID NO 129
<211> LENGTH: 21
<212> TYPE: DNA
<213> ORGANISM: Artificial Sequence
<220> FEATURE:
<223> OTHER INFORMATION: target sequence

<400> SEQUENCE: 129
aaagagagga agagaaacca t                                    21

<210> SEQ ID NO 130
<211> LENGTH: 21
<212> TYPE: DNA
<213> ORGANISM: Artificial Sequence
<220> FEATURE:
<223> OTHER INFORMATION: target sequence

<400> SEQUENCE: 130
aagagaggaa gagaaaccat t                                    21

<210> SEQ ID NO 131
<211> LENGTH: 21
<212> TYPE: DNA
<213> ORGANISM: Artificial Sequence
<220> FEATURE:
<223> OTHER INFORMATION: target sequence

<400> SEQUENCE: 131
aagagaaacc atttagagac t                                    21

<210> SEQ ID NO 132
<211> LENGTH: 21
<212> TYPE: DNA
<213> ORGANISM: Artificial Sequence
<220> FEATURE:
<223> OTHER INFORMATION: target sequence

<400> SEQUENCE: 132
aaaccattta gagactgtgc a                                    21

<210> SEQ ID NO 133
<211> LENGTH: 21
<212> TYPE: DNA
<213> ORGANISM: Artificial Sequence
<220> FEATURE:
<223> OTHER INFORMATION: target sequence

<400> SEQUENCE: 133

-continued aaccatttag agactgtgca g                    21

<210> SEQ ID NO 134
<211> LENGTH: 21
<212> TYPE: DNA
<213> ORGANISM: Artificial Sequence
<220> FEATURE:
<223> OTHER INFORMATION: target sequence

<400> SEQUENCE: 134
aagctggttt taataaaagt g                    21

<210> SEQ ID NO 135
<211> LENGTH: 21
<212> TYPE: DNA
<213> ORGANISM: Artificial Sequence
<220> FEATURE:
<223> OTHER INFORMATION: target sequence

<400> SEQUENCE: 135
aataaaagtg gaatctacac t                    21

<210> SEQ ID NO 136
<211> LENGTH: 21
<212> TYPE: DNA
<213> ORGANISM: Artificial Sequence
<220> FEATURE:
<223> OTHER INFORMATION: target sequence

<400> SEQUENCE: 136
aaaagtggaa tctacactat t                    21

<210> SEQ ID NO 137
<211> LENGTH: 21
<212> TYPE: DNA
<213> ORGANISM: Artificial Sequence
<220> FEATURE:
<223> OTHER INFORMATION: target sequence

<400> SEQUENCE: 137
aaagtggaat ctacactatt t                    21

<210> SEQ ID NO 138
<211> LENGTH: 21
<212> TYPE: DNA
<213> ORGANISM: Artificial Sequence
<220> FEATURE:
<223> OTHER INFORMATION: target sequence

<400> SEQUENCE: 138
aagtggaatc tacactattt a                    21

<210> SEQ ID NO 139
<211> LENGTH: 21
<212> TYPE: DNA
<213> ORGANISM: Artificial Sequence
<220> FEATURE:
<223> OTHER INFORMATION: target sequence

<400> SEQUENCE: 139
aatctacact atttatatta a                    21

<210> SEQ ID NO 140
<211> LENGTH: 21
<212> TYPE: DNA
<213> ORGANISM: Artificial Sequence

```
<220> FEATURE:
<223> OTHER INFORMATION: target sequence

<400> SEQUENCE: 140
aataatatgc cagaacccaa a                                              21

<210> SEQ ID NO 141
<211> LENGTH: 21
<212> TYPE: DNA
<213> ORGANISM: Artificial Sequence
<220> FEATURE:
<223> OTHER INFORMATION: target sequence

<400> SEQUENCE: 141
aatatgccag aacccaaaaa g                                              21

<210> SEQ ID NO 142
<211> LENGTH: 21
<212> TYPE: DNA
<213> ORGANISM: Artificial Sequence
<220> FEATURE:
<223> OTHER INFORMATION: target sequence

<400> SEQUENCE: 142
aacccaaaaa ggtgttttgc a                                              21

<210> SEQ ID NO 143
<211> LENGTH: 21
<212> TYPE: DNA
<213> ORGANISM: Artificial Sequence
<220> FEATURE:
<223> OTHER INFORMATION: target sequence

<400> SEQUENCE: 143
aaaaaggtgt tttgcaatat g                                              21

<210> SEQ ID NO 144
<211> LENGTH: 21
<212> TYPE: DNA
<213> ORGANISM: Artificial Sequence
<220> FEATURE:
<223> OTHER INFORMATION: target sequence

<400> SEQUENCE: 144
aaaaggtgtt ttgcaatatg g                                              21

<210> SEQ ID NO 145
<211> LENGTH: 21
<212> TYPE: DNA
<213> ORGANISM: Artificial Sequence
<220> FEATURE:
<223> OTHER INFORMATION: target sequence

<400> SEQUENCE: 145
aaaggtgttt tgcaatatgg a                                              21

<210> SEQ ID NO 146
<211> LENGTH: 21
<212> TYPE: DNA
<213> ORGANISM: Artificial Sequence
<220> FEATURE:
<223> OTHER INFORMATION: target sequence

<400> SEQUENCE: 146
aaggtgtttt gcaatatgga t                                              21
```

```
<210> SEQ ID NO 147
<211> LENGTH: 21
<212> TYPE: DNA
<213> ORGANISM: Artificial Sequence
<220> FEATURE:
<223> OTHER INFORMATION: target sequence

<400> SEQUENCE: 147
aatatggatg tcaatggggg a                                         21

<210> SEQ ID NO 148
<211> LENGTH: 21
<212> TYPE: DNA
<213> ORGANISM: Artificial Sequence
<220> FEATURE:
<223> OTHER INFORMATION: target sequence

<400> SEQUENCE: 148 aatggggag gttggactgt a                                          21

<210> SEQ ID NO 149
<211> LENGTH: 21
<212> TYPE: DNA
<213> ORGANISM: Artificial Sequence
<220> FEATURE:
<223> OTHER INFORMATION: target sequence

<400> SEQUENCE: 149
aatacaacat cgtgaagatg g                                         21

<210> SEQ ID NO 150
<211> LENGTH: 21
<212> TYPE: DNA
<213> ORGANISM: Artificial Sequence
<220> FEATURE:
<223> OTHER INFORMATION: target sequence

<400> SEQUENCE: 150
aacatcgtga agatggaagt c                                         21

<210> SEQ ID NO 151
<211> LENGTH: 21
<212> TYPE: DNA
<213> ORGANISM: Artificial Sequence
<220> FEATURE:
<223> OTHER INFORMATION: target sequence

<400> SEQUENCE: 151
aagatggaag tctagatttc c                                         21

<210> SEQ ID NO 152
<211> LENGTH: 21
<212> TYPE: DNA
<213> ORGANISM: Artificial Sequence
<220> FEATURE:
<223> OTHER INFORMATION: target sequence

<400> SEQUENCE: 152
aagtctagat ttccaaagag g                                         21

<210> SEQ ID NO 153
<211> LENGTH: 21
<212> TYPE: DNA
<213> ORGANISM: Artificial Sequence
<220> FEATURE:
<223> OTHER INFORMATION: target sequence

<400> SEQUENCE: 153
```
aaagaggctg gaaggaatat a                           21

<210> SEQ ID NO 154
<211> LENGTH: 21
<212> TYPE: DNA
<213> ORGANISM: Artificial Sequence
<220> FEATURE:
<223> OTHER INFORMATION: target sequence

<400> SEQUENCE: 154
aagaggctgg aaggaatata a                           21

<210> SEQ ID NO 155
<211> LENGTH: 21
<212> TYPE: DNA
<213> ORGANISM: Artificial Sequence
<220> FEATURE:
<223> OTHER INFORMATION: target sequence

<400> SEQUENCE: 155
aaggaatata aaatgggttt t                           21

<210> SEQ ID NO 156
<211> LENGTH: 21
<212> TYPE: DNA
<213> ORGANISM: Artificial Sequence
<220> FEATURE:
<223> OTHER INFORMATION: target sequence

<400> SEQUENCE: 156
aatataaaat gggttttgga a                           21

<210> SEQ ID NO 157
<211> LENGTH: 20
<212> TYPE: DNA
<213> ORGANISM: Artificial Sequence
<220> FEATURE:
<223> OTHER INFORMATION: target sequence

<400> SEQUENCE: 157
aaaatgggtt ttggaaatcc                             20

<210> SEQ ID NO 158
<211> LENGTH: 21
<212> TYPE: DNA
<213> ORGANISM: Artificial Sequence
<220> FEATURE:
<223> OTHER INFORMATION: target sequence

<400> SEQUENCE: 158
aaatgggttt tggaaatccc t                           21

<210> SEQ ID NO 159
<211> LENGTH: 21
<212> TYPE: DNA
<213> ORGANISM: Artificial Sequence
<220> FEATURE:
<223> OTHER INFORMATION: target sequence

<400> SEQUENCE: 159
aatgggtttt ggaaatccct c                           21

<210> SEQ ID NO 160
<211> LENGTH: 21
<212> TYPE: DNA
<213> ORGANISM: Artificial Sequence

```
<220> FEATURE:
<223> OTHER INFORMATION: target sequence

<400> SEQUENCE: 160
aaatccctcc ggtgaatatt g                                              21

<210> SEQ ID NO 161
<211> LENGTH: 21
<212> TYPE: DNA
<213> ORGANISM: Artificial Sequence
<220> FEATURE:
<223> OTHER INFORMATION: target sequence

<400> SEQUENCE: 161
aatccctccg gtgaatattg g                                              21

<210> SEQ ID NO 162
<211> LENGTH: 21
<212> TYPE: DNA
<213> ORGANISM: Artificial Sequence
<220> FEATURE:
<223> OTHER INFORMATION: target sequence

<400> SEQUENCE: 162
aatattggct ggggaatgag t                                              21

<210> SEQ ID NO 163
<211> LENGTH: 21
<212> TYPE: DNA
<213> ORGANISM: Artificial Sequence
<220> FEATURE:
<223> OTHER INFORMATION: target sequence

<400> SEQUENCE: 163
aatgagttta tttttgccat t                                              21

<210> SEQ ID NO 164
<211> LENGTH: 21
<212> TYPE: DNA
<213> ORGANISM: Artificial Sequence
<220> FEATURE:
<223> OTHER INFORMATION: target sequence

<400> SEQUENCE: 164
aagaattgag ttaatggact g                                              21

<210> SEQ ID NO 165
<211> LENGTH: 21
<212> TYPE: DNA
<213> ORGANISM: Artificial Sequence
<220> FEATURE:
<223> OTHER INFORMATION: target sequence

<400> SEQUENCE: 165
aattgagtta atggactggg a                                              21

<210> SEQ ID NO 166
<211> LENGTH: 21
<212> TYPE: DNA
<213> ORGANISM: Artificial Sequence
<220> FEATURE:
<223> OTHER INFORMATION: target sequence

<400> SEQUENCE: 166
aatggactgg gaagggaacc g                                              21
```

```
<210> SEQ ID NO 167
<211> LENGTH: 21
<212> TYPE: DNA
<213> ORGANISM: Artificial Sequence
<220> FEATURE:
<223> OTHER INFORMATION: target sequence

<400> SEQUENCE: 167
aagggaaccg agcctattca c                                              21

<210> SEQ ID NO 168
<211> LENGTH: 21
<212> TYPE: DNA
<213> ORGANISM: Artificial Sequence
<220> FEATURE:
<223> OTHER INFORMATION: target sequence

<400> SEQUENCE: 168
aaccgagcct attcacagta t                                              21

<210> SEQ ID NO 169
<211> LENGTH: 21
<212> TYPE: DNA
<213> ORGANISM: Artificial Sequence
<220> FEATURE:
<223> OTHER INFORMATION: target sequence

<400> SEQUENCE: 169
aaatgaaaag caaaactata g                                              21

<210> SEQ ID NO 170
<211> LENGTH: 21
<212> TYPE: DNA
<213> ORGANISM: Artificial Sequence
<220> FEATURE:
<223> OTHER INFORMATION: target sequence

<400> SEQUENCE: 170
aatgaaaagc aaaactatag g                                              21

<210> SEQ ID NO 171
<211> LENGTH: 21
<212> TYPE: DNA
<213> ORGANISM: Artificial Sequence
<220> FEATURE:
<223> OTHER INFORMATION: target sequence

<400> SEQUENCE: 171
aaaagcaaaa ctataggttg t                                              21

<210> SEQ ID NO 172
<211> LENGTH: 21
<212> TYPE: DNA
<213> ORGANISM: Artificial Sequence
<220> FEATURE:
<223> OTHER INFORMATION: target sequence

<400> SEQUENCE: 172
aaagcaaaac tataggttgt a                                              21

<210> SEQ ID NO 173
<211> LENGTH: 21
<212> TYPE: DNA
<213> ORGANISM: Artificial Sequence
<220> FEATURE:
<223> OTHER INFORMATION: target sequence

<400> SEQUENCE: 173
```
aagcaaaact ataggttgta t                                            21

<210> SEQ ID NO 174
<211> LENGTH: 21
<212> TYPE: DNA
<213> ORGANISM: Artificial Sequence
<220> FEATURE:
<223> OTHER INFORMATION: target sequence

<400> SEQUENCE: 174
aaaactatag gttgtattta a                                            21

<210> SEQ ID NO 175
<211> LENGTH: 21
<212> TYPE: DNA
<213> ORGANISM: Artificial Sequence
<220> FEATURE:
<223> OTHER INFORMATION: target sequence

<400> SEQUENCE: 175
aaactatagg ttgtatttaa a                                            21

<210> SEQ ID NO 176
<211> LENGTH: 21
<212> TYPE: DNA
<213> ORGANISM: Artificial Sequence
<220> FEATURE:
<223> OTHER INFORMATION: target sequence

<400> SEQUENCE: 176
aactataggt tgtatttaaa a                                            21

<210> SEQ ID NO 177
<211> LENGTH: 21
<212> TYPE: DNA
<213> ORGANISM: Artificial Sequence
<220> FEATURE:
<223> OTHER INFORMATION: target sequence

<400> SEQUENCE: 177
aaaaggtcac actgggacag c                                            21

<210> SEQ ID NO 178
<211> LENGTH: 21
<212> TYPE: DNA
<213> ORGANISM: Artificial Sequence
<220> FEATURE:
<223> OTHER INFORMATION: target sequence

<400> SEQUENCE: 178
aaaggtcaca ctgggacagc a                                            21

<210> SEQ ID NO 179
<211> LENGTH: 21
<212> TYPE: DNA
<213> ORGANISM: Artificial Sequence
<220> FEATURE:
<223> OTHER INFORMATION: target sequence

<400> SEQUENCE: 179
aaggtcacac tgggacagca g                                            21

<210> SEQ ID NO 180
<211> LENGTH: 21
<212> TYPE: DNA
<213> ORGANISM: Artificial Sequence

```
<220> FEATURE:
<223> OTHER INFORMATION: target sequence

<400> SEQUENCE: 180
aaaacagagc agcctgatct t                                              21

<210> SEQ ID NO 181
<211> LENGTH: 21
<212> TYPE: DNA
<213> ORGANISM: Artificial Sequence
<220> FEATURE:
<223> OTHER INFORMATION: target sequence

<400> SEQUENCE: 181
aaacagagca gcctgatctt a                                              21

<210> SEQ ID NO 182
<211> LENGTH: 21
<212> TYPE: DNA
<213> ORGANISM: Artificial Sequence
<220> FEATURE:
<223> OTHER INFORMATION: target sequence

<400> SEQUENCE: 182
aacagagcag cctgatctta c                                              21

<210> SEQ ID NO 183
<211> LENGTH: 21
<212> TYPE: DNA
<213> ORGANISM: Artificial Sequence
<220> FEATURE:
<223> OTHER INFORMATION: target sequence

<400> SEQUENCE: 183
aaagatgctg ataatgacaa c                                              21

<210> SEQ ID NO 184
<211> LENGTH: 21
<212> TYPE: DNA
<213> ORGANISM: Artificial Sequence
<220> FEATURE:
<223> OTHER INFORMATION: target sequence

<400> SEQUENCE: 184
aagatgctga taatgacaac t                                              21

<210> SEQ ID NO 185
<211> LENGTH: 21
<212> TYPE: DNA
<213> ORGANISM: Artificial Sequence
<220> FEATURE:
<223> OTHER INFORMATION: target sequence

<400> SEQUENCE: 185
aatgacaact gtatgtgcaa a                                              21

<210> SEQ ID NO 186
<211> LENGTH: 21
<212> TYPE: DNA
<213> ORGANISM: Artificial Sequence
<220> FEATURE:
<223> OTHER INFORMATION: target sequence

<400> SEQUENCE: 186
aactgtatgt gcaaatgtgc c                                              21
```

```
<210> SEQ ID NO 187
<211> LENGTH: 21
<212> TYPE: DNA
<213> ORGANISM: Artificial Sequence
<220> FEATURE:
<223> OTHER INFORMATION: target sequence

<400> SEQUENCE: 187
aaatgtgccc tcatgttaac a                                      21

<210> SEQ ID NO 188
<211> LENGTH: 21
<212> TYPE: DNA
<213> ORGANISM: Artificial Sequence
<220> FEATURE:
<223> OTHER INFORMATION: target sequence

<400> SEQUENCE: 188
aatgtgccct catgttaaca g                                      21

<210> SEQ ID NO 189
<211> LENGTH: 21
<212> TYPE: DNA
<213> ORGANISM: Artificial Sequence
<220> FEATURE:
<223> OTHER INFORMATION: target sequence

<400> SEQUENCE: 189
aacaggagga tggtggtttg a                                      21

<210> SEQ ID NO 190
<211> LENGTH: 21
<212> TYPE: DNA
<213> ORGANISM: Artificial Sequence
<220> FEATURE:
<223> OTHER INFORMATION: target sequence

<400> SEQUENCE: 190
aatctaaatg gaatgttcta t                                      21

<210> SEQ ID NO 191
<211> LENGTH: 21
<212> TYPE: DNA
<213> ORGANISM: Artificial Sequence
<220> FEATURE:
<223> OTHER INFORMATION: target sequence

<400> SEQUENCE: 191
aaatggaatg ttctatactg c                                      21

<210> SEQ ID NO 192
<211> LENGTH: 21
<212> TYPE: DNA
<213> ORGANISM: Artificial Sequence
<220> FEATURE:
<223> OTHER INFORMATION: target sequence

<400> SEQUENCE: 192
aatggaatgt tctatactgc g                                      21

<210> SEQ ID NO 193
<211> LENGTH: 21
<212> TYPE: DNA
<213> ORGANISM: Artificial Sequence
<220> FEATURE:
<223> OTHER INFORMATION: target sequence

<400> SEQUENCE: 193
```
aatgttctat actgcgggac a                                    21

<210> SEQ ID NO 194
<211> LENGTH: 21
<212> TYPE: DNA
<213> ORGANISM: Artificial Sequence
<220> FEATURE:
<223> OTHER INFORMATION: target sequence

<400> SEQUENCE: 194
aaaaccatgg aaaactgaat g                                    21

<210> SEQ ID NO 195
<211> LENGTH: 21
<212> TYPE: DNA
<213> ORGANISM: Artificial Sequence
<220> FEATURE:
<223> OTHER INFORMATION: target sequence

<400> SEQUENCE: 195
aaaccatgga aaactgaatg g                                    21

<210> SEQ ID NO 196
<211> LENGTH: 21
<212> TYPE: DNA
<213> ORGANISM: Artificial Sequence
<220> FEATURE:
<223> OTHER INFORMATION: target sequence

<400> SEQUENCE: 196
aaccatggaa actgaatgg g                                     21

<210> SEQ ID NO 197
<211> LENGTH: 21
<212> TYPE: DNA
<213> ORGANISM: Artificial Sequence
<220> FEATURE:
<223> OTHER INFORMATION: target sequence

<400> SEQUENCE: 197
aaaactgaat gggataaagt g                                    21

<210> SEQ ID NO 198
<211> LENGTH: 21
<212> TYPE: DNA
<213> ORGANISM: Artificial Sequence
<220> FEATURE:
<223> OTHER INFORMATION: target sequence

<400> SEQUENCE: 198
aaactgaatg ggataaagtg g                                    21

<210> SEQ ID NO 199
<211> LENGTH: 21
<212> TYPE: DNA
<213> ORGANISM: Artificial Sequence
<220> FEATURE:
<223> OTHER INFORMATION: target sequence

<400> SEQUENCE: 199
aactgaatgg gataaagtgg c                                    21

<210> SEQ ID NO 200
<211> LENGTH: 21
<212> TYPE: DNA
<213> ORGANISM: Artificial Sequence

```
<220> FEATURE:
<223> OTHER INFORMATION: target sequence

<400> SEQUENCE: 200
aatgggataa agtggcacta c                                              21

<210> SEQ ID NO 201
<211> LENGTH: 21
<212> TYPE: DNA
<213> ORGANISM: Artificial Sequence
<220> FEATURE:
<223> OTHER INFORMATION: target sequence

<400> SEQUENCE: 201
aaagtggcac tacttcaaag g                                              21

<210> SEQ ID NO 202
<211> LENGTH: 21
<212> TYPE: DNA
<213> ORGANISM: Artificial Sequence
<220> FEATURE:
<223> OTHER INFORMATION: target sequence

<400> SEQUENCE: 202
aagtggcact acttcaaagg g                                              21

<210> SEQ ID NO 203
<211> LENGTH: 21
<212> TYPE: DNA
<213> ORGANISM: Artificial Sequence
<220> FEATURE:
<223> OTHER INFORMATION: target sequence

<400> SEQUENCE: 203
aaagggccca gttactcctt a                                              21

<210> SEQ ID NO 204
<211> LENGTH: 21
<212> TYPE: DNA
<213> ORGANISM: Artificial Sequence
<220> FEATURE:
<223> OTHER INFORMATION: target sequence

<400> SEQUENCE: 204
aagggcccag ttactcctta c                                              21

<210> SEQ ID NO 205
<211> LENGTH: 21
<212> TYPE: DNA
<213> ORGANISM: Artificial Sequence
<220> FEATURE:
<223> OTHER INFORMATION: target sequence

<400> SEQUENCE: 205
gaagtccaga aacagtggg a                                               21

<210> SEQ ID NO 206
<211> LENGTH: 21
<212> TYPE: DNA
<213> ORGANISM: Artificial Sequence
<220> FEATURE:
<223> OTHER INFORMATION: target sequence

<400> SEQUENCE: 206
atggcaactg tcgtgagagt a                                              21
```

```
<210> SEQ ID NO 207
<211> LENGTH: 21
<212> TYPE: DNA
<213> ORGANISM: Artificial Sequence
<220> FEATURE:
<223> OTHER INFORMATION: target sequence

<400> SEQUENCE: 207
cgtggaaccg gatttctctt c                                            21

<210> SEQ ID NO 208
<211> LENGTH: 21
<212> TYPE: DNA
<213> ORGANISM: Artificial Sequence
<220> FEATURE:
<223> OTHER INFORMATION: target sequence

<400> SEQUENCE: 208
cattgtggaa aacatgaagt c                                            21

<210> SEQ ID NO 209
<211> LENGTH: 21
<212> TYPE: DNA
<213> ORGANISM: Artificial Sequence
<220> FEATURE:
<223> OTHER INFORMATION: target sequence

<400> SEQUENCE: 209
ttcagaacca cacggctacc a                                            21

<210> SEQ ID NO 210
<211> LENGTH: 21
<212> TYPE: DNA
<213> ORGANISM: Artificial Sequence
<220> FEATURE:
<223> OTHER INFORMATION: target sequence

<400> SEQUENCE: 210
tactaaatca aacttctcga c                                            21

<210> SEQ ID NO 211
<211> LENGTH: 21
<212> TYPE: DNA
<213> ORGANISM: Artificial Sequence
<220> FEATURE:
<223> OTHER INFORMATION: target sequence

<400> SEQUENCE: 211
cttcaacaga caaatgaaat c                                            21

<210> SEQ ID NO 212
<211> LENGTH: 21
<212> TYPE: DNA
<213> ORGANISM: Artificial Sequence
<220> FEATURE:
<223> OTHER INFORMATION: target sequence

<400> SEQUENCE: 212
gttggacacc ttaaaggaag a                                            21

<210> SEQ ID NO 213
<211> LENGTH: 21
<212> TYPE: DNA
<213> ORGANISM: Artificial Sequence
<220> FEATURE:
<223> OTHER INFORMATION: target sequence

<400> SEQUENCE: 213
```
agctaccacc aacaacagtg t                           21

<210> SEQ ID NO 214
<211> LENGTH: 21
<212> TYPE: DNA
<213> ORGANISM: Artificial Sequence
<220> FEATURE:
<223> OTHER INFORMATION: target sequence

<400> SEQUENCE: 214
ggtgttttac taaagggagg a                           21

<210> SEQ ID NO 215
<211> LENGTH: 21
<212> TYPE: DNA
<213> ORGANISM: Artificial Sequence
<220> FEATURE:
<223> OTHER INFORMATION: target sequence

<400> SEQUENCE: 215
tgtatatcaa gctggtttta a                           21

<210> SEQ ID NO 216
<211> LENGTH: 21
<212> TYPE: DNA
<213> ORGANISM: Artificial Sequence
<220> FEATURE:
<223> OTHER INFORMATION: target sequence

<400> SEQUENCE: 216
ccaaaaaggt gttttgcaat a                           21

<210> SEQ ID NO 217
<211> LENGTH: 21
<212> TYPE: DNA
<213> ORGANISM: Artificial Sequence
<220> FEATURE:
<223> OTHER INFORMATION: target sequence

<400> SEQUENCE: 217
gctggaagga atataaaatg g                           21

<210> SEQ ID NO 218
<211> LENGTH: 21
<212> TYPE: DNA
<213> ORGANISM: Artificial Sequence
<220> FEATURE:
<223> OTHER INFORMATION: target sequence

<400> SEQUENCE: 218
tcagaggcag tacatgctaa g                           21

<210> SEQ ID NO 219
<211> LENGTH: 21
<212> TYPE: DNA
<213> ORGANISM: Artificial Sequence
<220> FEATURE:
<223> OTHER INFORMATION: target sequence

<400> SEQUENCE: 219
acactgggac agcaggaaaa c                           21

<210> SEQ ID NO 220
<211> LENGTH: 20
<212> TYPE: DNA
<213> ORGANISM: Artificial Sequence

```
<220> FEATURE:
<223> OTHER INFORMATION: target sequence

<400> SEQUENCE: 220
atttcagcac taaagatgct                                               20

<210> SEQ ID NO 221
<211> LENGTH: 22
<212> TYPE: DNA
<213> ORGANISM: Artificial Sequence
<220> FEATURE:
<223> OTHER INFORMATION: target sequence

<400> SEQUENCE: 221
gataatgaca actgtatgtg ca                                            22

<210> SEQ ID NO 222
<211> LENGTH: 19
<212> TYPE: DNA
<213> ORGANISM: Artificial Sequence
<220> FEATURE:
<223> OTHER INFORMATION: target sequence

<400> SEQUENCE: 222
tgtgccctca tgttaacag                                                19

<210> SEQ ID NO 223
<211> LENGTH: 18
<212> TYPE: DNA
<213> ORGANISM: Artificial Sequence
<220> FEATURE:
<223> OTHER INFORMATION: target sequence

<400> SEQUENCE: 223
aggatggtgg tttgatgc                                                 18

<210> SEQ ID NO 224
<211> LENGTH: 19
<212> TYPE: DNA
<213> ORGANISM: Artificial Sequence
<220> FEATURE:
<223> OTHER INFORMATION: target sequence

<400> SEQUENCE: 224
tggcccctcc aatctaaat                                                19

<210> SEQ ID NO 225
<211> LENGTH: 22
<212> TYPE: DNA
<213> ORGANISM: Artificial Sequence
<220> FEATURE:
<223> OTHER INFORMATION: target sequence

<400> SEQUENCE: 225
aatgttctat actgcgggac aa                                            22

<210> SEQ ID NO 226
<211> LENGTH: 23
<212> TYPE: DNA
<213> ORGANISM: Artificial Sequence
<220> FEATURE:
<223> OTHER INFORMATION: target sequence

<400> SEQUENCE: 226
atggaaaact gaatgggata aag                                           23
```

```
<210> SEQ ID NO 227
<211> LENGTH: 24
<212> TYPE: DNA
<213> ORGANISM: Artificial Sequence
<220> FEATURE:
<223> OTHER INFORMATION: target sequence

<400> SEQUENCE: 227
aactgaatgg gataaagtgg cact                                          24

<210> SEQ ID NO 228
<211> LENGTH: 21
<212> TYPE: DNA
<213> ORGANISM: Artificial Sequence
<220> FEATURE:
<223> OTHER INFORMATION: target sequence

<400> SEQUENCE: 228
aacaactttc ggaagagcat g                                             21

<210> SEQ ID NO 229
<211> LENGTH: 21
<212> TYPE: DNA
<213> ORGANISM: Artificial Sequence
<220> FEATURE:
<223> OTHER INFORMATION: target sequence

<400> SEQUENCE: 229
aactttcgga agagcatgga c                                             21

<210> SEQ ID NO 230
<211> LENGTH: 21
<212> TYPE: DNA
<213> ORGANISM: Artificial Sequence
<220> FEATURE:
<223> OTHER INFORMATION: target sequence

<400> SEQUENCE: 230
aagagcatgg acagcatagg a                                             21

<210> SEQ ID NO 231
<211> LENGTH: 21
<212> TYPE: DNA
<213> ORGANISM: Artificial Sequence
<220> FEATURE:
<223> OTHER INFORMATION: target sequence

<400> SEQUENCE: 231
aaagaagcaa tatcaggtcc a                                             21

<210> SEQ ID NO 232
<211> LENGTH: 21
<212> TYPE: DNA
<213> ORGANISM: Artificial Sequence
<220> FEATURE:
<223> OTHER INFORMATION: target sequence

<400> SEQUENCE: 232
aagaagcaat atcaggtcca g                                             21

<210> SEQ ID NO 233
<211> LENGTH: 21
<212> TYPE: DNA
<213> ORGANISM: Artificial Sequence
<220> FEATURE:
<223> OTHER INFORMATION: target sequence

<400> SEQUENCE: 233
```
aagcaatatc aggtccagca t         21

<210> SEQ ID NO 234
<211> LENGTH: 21
<212> TYPE: DNA
<213> ORGANISM: Artificial Sequence
<220> FEATURE:
<223> OTHER INFORMATION: target sequence

<400> SEQUENCE: 234
aatatcaggt ccagcatggg t         21

<210> SEQ ID NO 235
<211> LENGTH: 21
<212> TYPE: DNA
<213> ORGANISM: Artificial Sequence
<220> FEATURE:
<223> OTHER INFORMATION: target sequence

<400> SEQUENCE: 235
aactgccgct cttcctccag c         21

<210> SEQ ID NO 236
<211> LENGTH: 21
<212> TYPE: DNA
<213> ORGANISM: Artificial Sequence
<220> FEATURE:
<223> OTHER INFORMATION: target sequence

<400> SEQUENCE: 236
aatgctgtgc agagggacgc g         21

<210> SEQ ID NO 237
<211> LENGTH: 21
<212> TYPE: DNA
<213> ORGANISM: Artificial Sequence
<220> FEATURE:
<223> OTHER INFORMATION: target sequence

<400> SEQUENCE: 237
aatacgatga ctcggtgcag a         21

<210> SEQ ID NO 238
<211> LENGTH: 21
<212> TYPE: DNA
<213> ORGANISM: Artificial Sequence
<220> FEATURE:
<223> OTHER INFORMATION: target sequence

<400> SEQUENCE: 238
aagtgctgga gaacatcatg g         21

<210> SEQ ID NO 239
<211> LENGTH: 21
<212> TYPE: DNA
<213> ORGANISM: Artificial Sequence
<220> FEATURE:
<223> OTHER INFORMATION: target sequence

<400> SEQUENCE: 239
aacatcatgg aaaacaacac t         21

<210> SEQ ID NO 240
<211> LENGTH: 21
<212> TYPE: DNA
<213> ORGANISM: Artificial Sequence

```
<220> FEATURE:
<223> OTHER INFORMATION: target sequence

<400> SEQUENCE: 240
aaaacaacac tcagtggcta a                                              21

<210> SEQ ID NO 241
<211> LENGTH: 21
<212> TYPE: DNA
<213> ORGANISM: Artificial Sequence
<220> FEATURE:
<223> OTHER INFORMATION: target sequence

<400> SEQUENCE: 241
aaacaacact cagtggctaa t                                              21

<210> SEQ ID NO 242
<211> LENGTH: 21
<212> TYPE: DNA
<213> ORGANISM: Artificial Sequence
<220> FEATURE:
<223> OTHER INFORMATION: target sequence

<400> SEQUENCE: 242
aacaacactc agtggctaat g                                              21

<210> SEQ ID NO 243
<211> LENGTH: 21
<212> TYPE: DNA
<213> ORGANISM: Artificial Sequence
<220> FEATURE:
<223> OTHER INFORMATION: target sequence

<400> SEQUENCE: 243
aacactcagt ggctaatgaa g                                              21

<210> SEQ ID NO 244
<211> LENGTH: 21
<212> TYPE: DNA
<213> ORGANISM: Artificial Sequence
<220> FEATURE:
<223> OTHER INFORMATION: target sequence

<400> SEQUENCE: 244
aatgaagctt gagaattata t                                              21

<210> SEQ ID NO 245
<211> LENGTH: 21
<212> TYPE: DNA
<213> ORGANISM: Artificial Sequence
<220> FEATURE:
<223> OTHER INFORMATION: target sequence

<400> SEQUENCE: 245
aagcttgaga attatatcca g                                              21

<210> SEQ ID NO 246
<211> LENGTH: 21
<212> TYPE: DNA
<213> ORGANISM: Artificial Sequence
<220> FEATURE:
<223> OTHER INFORMATION: target sequence

<400> SEQUENCE: 246
aattatatcc aggacaacat g                                              21
```

```
<210> SEQ ID NO 247
<211> LENGTH: 21
<212> TYPE: DNA
<213> ORGANISM: Artificial Sequence
<220> FEATURE:
<223> OTHER INFORMATION: target sequence

<400> SEQUENCE: 247
aacatgaaga aagaaatggt a                                              21

<210> SEQ ID NO 248
<211> LENGTH: 21
<212> TYPE: DNA
<213> ORGANISM: Artificial Sequence
<220> FEATURE:
<223> OTHER INFORMATION: target sequence

<400> SEQUENCE: 248
aagaaagaaa tggtagagat a                                              21

<210> SEQ ID NO 249
<211> LENGTH: 21
<212> TYPE: DNA
<213> ORGANISM: Artificial Sequence
<220> FEATURE:
<223> OTHER INFORMATION: target sequence

<400> SEQUENCE: 249
aaagaaatgg tagagataca g                                              21

<210> SEQ ID NO 250
<211> LENGTH: 21
<212> TYPE: DNA
<213> ORGANISM: Artificial Sequence
<220> FEATURE:
<223> OTHER INFORMATION: target sequence

<400> SEQUENCE: 250
aagaaatggt agagatacag c                                              21

<210> SEQ ID NO 251
<211> LENGTH: 21
<212> TYPE: DNA
<213> ORGANISM: Artificial Sequence
<220> FEATURE:
<223> OTHER INFORMATION: target sequence

<400> SEQUENCE: 251
aaatggtaga gatacagcag a                                              21

<210> SEQ ID NO 252
<211> LENGTH: 21
<212> TYPE: DNA
<213> ORGANISM: Artificial Sequence
<220> FEATURE:
<223> OTHER INFORMATION: target sequence

<400> SEQUENCE: 252
aatggtagag atacagcaga a                                              21

<210> SEQ ID NO 253
<211> LENGTH: 21
<212> TYPE: DNA
<213> ORGANISM: Artificial Sequence
<220> FEATURE:
<223> OTHER INFORMATION: target sequence

<400> SEQUENCE: 253
```

```
aatgcagtac agaaccagac g                                              21

<210> SEQ ID NO 254
<211> LENGTH: 21
<212> TYPE: DNA
<213> ORGANISM: Artificial Sequence
<220> FEATURE:
<223> OTHER INFORMATION: target sequence

<400> SEQUENCE: 254
aaccagacgg ctgtgatgat a                                              21

<210> SEQ ID NO 255
<211> LENGTH: 21
<212> TYPE: DNA
<213> ORGANISM: Artificial Sequence
<220> FEATURE:
<223> OTHER INFORMATION: target sequence

<400> SEQUENCE: 255
aaatagggac aaacctgttg a                                              21

<210> SEQ ID NO 256
<211> LENGTH: 21
<212> TYPE: DNA
<213> ORGANISM: Artificial Sequence
<220> FEATURE:
<223> OTHER INFORMATION: target sequence

<400> SEQUENCE: 256
aatagggaca aacctgttga a                                              21

<210> SEQ ID NO 257
<211> LENGTH: 21
<212> TYPE: DNA
<213> ORGANISM: Artificial Sequence
<220> FEATURE:
<223> OTHER INFORMATION: target sequence

<400> SEQUENCE: 257
aaacctgttg aaccaaacag c                                              21

<210> SEQ ID NO 258
<211> LENGTH: 21
<212> TYPE: DNA
<213> ORGANISM: Artificial Sequence
<220> FEATURE:
<223> OTHER INFORMATION: target sequence

<400> SEQUENCE: 258
aacctgttga accaaacagc t                                              21

<210> SEQ ID NO 259
<211> LENGTH: 21
<212> TYPE: DNA
<213> ORGANISM: Artificial Sequence
<220> FEATURE:
<223> OTHER INFORMATION: target sequence

<400> SEQUENCE: 259
aaccaaacag ctgagcaaac g                                              21

<210> SEQ ID NO 260
<211> LENGTH: 21
<212> TYPE: DNA
<213> ORGANISM: Artificial Sequence
```

```
<220> FEATURE:
<223> OTHER INFORMATION: target sequence

<400> SEQUENCE: 260
aaacagctga gcaaacgcgg a                                              21

<210> SEQ ID NO 261
<211> LENGTH: 21
<212> TYPE: DNA
<213> ORGANISM: Artificial Sequence
<220> FEATURE:
<223> OTHER INFORMATION: target sequence

<400> SEQUENCE: 261
aacagctgag caaacgcgga a                                              21

<210> SEQ ID NO 262
<211> LENGTH: 21
<212> TYPE: DNA
<213> ORGANISM: Artificial Sequence
<220> FEATURE:
<223> OTHER INFORMATION: target sequence

<400> SEQUENCE: 262
aaacgcggaa gttaactgat g                                              21

<210> SEQ ID NO 263
<211> LENGTH: 21
<212> TYPE: DNA
<213> ORGANISM: Artificial Sequence
<220> FEATURE:
<223> OTHER INFORMATION: target sequence

<400> SEQUENCE: 263
aacgcggaag ttaactgatg t                                              21

<210> SEQ ID NO 264
<211> LENGTH: 21
<212> TYPE: DNA
<213> ORGANISM: Artificial Sequence
<220> FEATURE:
<223> OTHER INFORMATION: target sequence

<400> SEQUENCE: 264
aagttaactg atgtggaagc c                                              21

<210> SEQ ID NO 265
<211> LENGTH: 21
<212> TYPE: DNA
<213> ORGANISM: Artificial Sequence
<220> FEATURE:
<223> OTHER INFORMATION: target sequence

<400> SEQUENCE: 265
aactgatgtg gaagcccaag t                                              21

<210> SEQ ID NO 266
<211> LENGTH: 21
<212> TYPE: DNA
<213> ORGANISM: Artificial Sequence
<220> FEATURE:
<223> OTHER INFORMATION: target sequence

<400> SEQUENCE: 266
aagcccaagt attaaatcag a                                              21
```

```
<210> SEQ ID NO 267
<211> LENGTH: 21
<212> TYPE: DNA
<213> ORGANISM: Artificial Sequence
<220> FEATURE:
<223> OTHER INFORMATION: target sequence

<400> SEQUENCE: 267
aagtattaaa tcagaccacg a                                              21

<210> SEQ ID NO 268
<211> LENGTH: 21
<212> TYPE: DNA
<213> ORGANISM: Artificial Sequence
<220> FEATURE:
<223> OTHER INFORMATION: target sequence

<400> SEQUENCE: 268
aaatcagacc acgagacttg a                                              21

<210> SEQ ID NO 269
<211> LENGTH: 21
<212> TYPE: DNA
<213> ORGANISM: Artificial Sequence
<220> FEATURE:
<223> OTHER INFORMATION: target sequence

<400> SEQUENCE: 269
aatcagacca cgagacttga a                                              21

<210> SEQ ID NO 270
<211> LENGTH: 21
<212> TYPE: DNA
<213> ORGANISM: Artificial Sequence
<220> FEATURE:
<223> OTHER INFORMATION: target sequence

<400> SEQUENCE: 270
aacttcagct cttggaacac t                                              21

<210> SEQ ID NO 271
<211> LENGTH: 21
<212> TYPE: DNA
<213> ORGANISM: Artificial Sequence
<220> FEATURE:
<223> OTHER INFORMATION: target sequence

<400> SEQUENCE: 271
aacactccct ctcgacaaac a                                              21

<210> SEQ ID NO 272
<211> LENGTH: 21
<212> TYPE: DNA
<213> ORGANISM: Artificial Sequence
<220> FEATURE:
<223> OTHER INFORMATION: target sequence

<400> SEQUENCE: 272
aaacaaattg gaaaaacaga t                                              21

<210> SEQ ID NO 273
<211> LENGTH: 21
<212> TYPE: DNA
<213> ORGANISM: Artificial Sequence
<220> FEATURE:
<223> OTHER INFORMATION: target sequence

<400> SEQUENCE: 273
```
aacaaattgg aaaaacagat t                                              21

<210> SEQ ID NO 274
<211> LENGTH: 21
<212> TYPE: DNA
<213> ORGANISM: Artificial Sequence
<220> FEATURE:
<223> OTHER INFORMATION: target sequence

<400> SEQUENCE: 274
aaattggaaa aacagatttt g                                              21

<210> SEQ ID NO 275
<211> LENGTH: 21
<212> TYPE: DNA
<213> ORGANISM: Artificial Sequence
<220> FEATURE:
<223> OTHER INFORMATION: target sequence

<400> SEQUENCE: 275
aattggaaaa acagattttg g                                              21

<210> SEQ ID NO 276
<211> LENGTH: 21
<212> TYPE: DNA
<213> ORGANISM: Artificial Sequence
<220> FEATURE:
<223> OTHER INFORMATION: target sequence

<400> SEQUENCE: 276
aaaaacagat tttggaccag a                                              21

<210> SEQ ID NO 277
<211> LENGTH: 21
<212> TYPE: DNA
<213> ORGANISM: Artificial Sequence
<220> FEATURE:
<223> OTHER INFORMATION: target sequence

<400> SEQUENCE: 277
aaaacagatt ttggaccaga c                                              21

<210> SEQ ID NO 278
<211> LENGTH: 21
<212> TYPE: DNA
<213> ORGANISM: Artificial Sequence
<220> FEATURE:
<223> OTHER INFORMATION: target sequence

<400> SEQUENCE: 278
aaacagattt tggaccagac c                                              21

<210> SEQ ID NO 279
<211> LENGTH: 21
<212> TYPE: DNA
<213> ORGANISM: Artificial Sequence
<220> FEATURE:
<223> OTHER INFORMATION: target sequence

<400> SEQUENCE: 279
aacagatttt ggaccagacc a                                              21

<210> SEQ ID NO 280
<211> LENGTH: 21
<212> TYPE: DNA
<213> ORGANISM: Artificial Sequence

```
<220> FEATURE:
<223> OTHER INFORMATION: target sequence

<400> SEQUENCE: 280
aaataaacaa attgcaagat a                                              21

<210> SEQ ID NO 281
<211> LENGTH: 21
<212> TYPE: DNA
<213> ORGANISM: Artificial Sequence
<220> FEATURE:
<223> OTHER INFORMATION: target sequence

<400> SEQUENCE: 281
aataaacaaa ttgcaagata a                                              21

<210> SEQ ID NO 282
<211> LENGTH: 21
<212> TYPE: DNA
<213> ORGANISM: Artificial Sequence
<220> FEATURE:
<223> OTHER INFORMATION: target sequence

<400> SEQUENCE: 282
aaacaaattg caagataaga a                                              21

<210> SEQ ID NO 283
<211> LENGTH: 21
<212> TYPE: DNA
<213> ORGANISM: Artificial Sequence
<220> FEATURE:
<223> OTHER INFORMATION: target sequence

<400> SEQUENCE: 283
aacaaattgc aagataagaa c                                              21

<210> SEQ ID NO 284
<211> LENGTH: 21
<212> TYPE: DNA
<213> ORGANISM: Artificial Sequence
<220> FEATURE:
<223> OTHER INFORMATION: target sequence

<400> SEQUENCE: 284
aaattgcaag ataagaacag t                                              21

<210> SEQ ID NO 285
<211> LENGTH: 21
<212> TYPE: DNA
<213> ORGANISM: Artificial Sequence
<220> FEATURE:
<223> OTHER INFORMATION: target sequence

<400> SEQUENCE: 285
aattgcaaga taagaacagt t                                              21

<210> SEQ ID NO 286
<211> LENGTH: 21
<212> TYPE: DNA
<213> ORGANISM: Artificial Sequence
<220> FEATURE:
<223> OTHER INFORMATION: target sequence

<400> SEQUENCE: 286
aagataagaa cagtttccta g                                              21
```

```
<210> SEQ ID NO 287
<211> LENGTH: 21
<212> TYPE: DNA
<213> ORGANISM: Artificial Sequence
<220> FEATURE:
<223> OTHER INFORMATION: target sequence

<400> SEQUENCE: 287
aagaacagtt tcctagaaaa g                                              21

<210> SEQ ID NO 288
<211> LENGTH: 21
<212> TYPE: DNA
<213> ORGANISM: Artificial Sequence
<220> FEATURE:
<223> OTHER INFORMATION: target sequence

<400> SEQUENCE: 288
aacagtttcc tagaaagaa g                                               21

<210> SEQ ID NO 289
<211> LENGTH: 21
<212> TYPE: DNA
<213> ORGANISM: Artificial Sequence
<220> FEATURE:
<223> OTHER INFORMATION: target sequence

<400> SEQUENCE: 289
aaaagaaggt gctagctatg g                                              21

<210> SEQ ID NO 290
<211> LENGTH: 21
<212> TYPE: DNA
<213> ORGANISM: Artificial Sequence
<220> FEATURE:
<223> OTHER INFORMATION: target sequence

<400> SEQUENCE: 290
aaagaaggtg ctagctatgg a                                              21

<210> SEQ ID NO 291
<211> LENGTH: 21
<212> TYPE: DNA
<213> ORGANISM: Artificial Sequence
<220> FEATURE:
<223> OTHER INFORMATION: target sequence

<400> SEQUENCE: 291
aagaaggtgc tagctatgga a                                              21

<210> SEQ ID NO 292
<211> LENGTH: 21
<212> TYPE: DNA
<213> ORGANISM: Artificial Sequence
<220> FEATURE:
<223> OTHER INFORMATION: target sequence

<400> SEQUENCE: 292
aaggtgctag ctatggaaga c                                              21

<210> SEQ ID NO 293
<211> LENGTH: 21
<212> TYPE: DNA
<213> ORGANISM: Artificial Sequence
<220> FEATURE:
<223> OTHER INFORMATION: target sequence

<400> SEQUENCE: 293
```

```
aagacaagca catcatccaa c                                              21

<210> SEQ ID NO 294
<211> LENGTH: 21
<212> TYPE: DNA
<213> ORGANISM: Artificial Sequence
<220> FEATURE:
<223> OTHER INFORMATION: target sequence

<400> SEQUENCE: 294
aagcacatca tccaactaca g                                              21

<210> SEQ ID NO 295
<211> LENGTH: 21
<212> TYPE: DNA
<213> ORGANISM: Artificial Sequence
<220> FEATURE:
<223> OTHER INFORMATION: target sequence

<400> SEQUENCE: 295
aactacagtc aataaaagaa g                                              21

<210> SEQ ID NO 296
<211> LENGTH: 21
<212> TYPE: DNA
<213> ORGANISM: Artificial Sequence
<220> FEATURE:
<223> OTHER INFORMATION: target sequence

<400> SEQUENCE: 296
aataaaagaa gagaaagatc a                                              21

<210> SEQ ID NO 297
<211> LENGTH: 21
<212> TYPE: DNA
<213> ORGANISM: Artificial Sequence
<220> FEATURE:
<223> OTHER INFORMATION: target sequence

<400> SEQUENCE: 297
aaaagaagag aaagatcagc t                                              21

<210> SEQ ID NO 298
<211> LENGTH: 21
<212> TYPE: DNA
<213> ORGANISM: Artificial Sequence
<220> FEATURE:
<223> OTHER INFORMATION: target sequence

<400> SEQUENCE: 298
aaagaagaga aagatcagct a                                              21

<210> SEQ ID NO 299
<211> LENGTH: 21
<212> TYPE: DNA
<213> ORGANISM: Artificial Sequence
<220> FEATURE:
<223> OTHER INFORMATION: target sequence

<400> SEQUENCE: 299
aagaagagaa agatcagcta c                                              21

<210> SEQ ID NO 300
<211> LENGTH: 21
<212> TYPE: DNA
<213> ORGANISM: Artificial Sequence
```

```
<220> FEATURE:
<223> OTHER INFORMATION: target sequence

<400> SEQUENCE: 300
aagagaaaga tcagctacag g                                              21

<210> SEQ ID NO 301
<211> LENGTH: 21
<212> TYPE: DNA
<213> ORGANISM: Artificial Sequence
<220> FEATURE:
<223> OTHER INFORMATION: target sequence

<400> SEQUENCE: 301
aaagatcagc tacaggtgtt a                                              21

<210> SEQ ID NO 302
<211> LENGTH: 21
<212> TYPE: DNA
<213> ORGANISM: Artificial Sequence
<220> FEATURE:
<223> OTHER INFORMATION: target sequence

<400> SEQUENCE: 302
aagatcagct acaggtgtta g                                              21

<210> SEQ ID NO 303
<211> LENGTH: 21
<212> TYPE: DNA
<213> ORGANISM: Artificial Sequence
<220> FEATURE:
<223> OTHER INFORMATION: target sequence

<400> SEQUENCE: 303
aagcaaaatt ccatcattga a                                              21

<210> SEQ ID NO 304
<211> LENGTH: 21
<212> TYPE: DNA
<213> ORGANISM: Artificial Sequence
<220> FEATURE:
<223> OTHER INFORMATION: target sequence

<400> SEQUENCE: 304
aaaattccat cattgaagaa c                                              21

<210> SEQ ID NO 305
<211> LENGTH: 21
<212> TYPE: DNA
<213> ORGANISM: Artificial Sequence
<220> FEATURE:
<223> OTHER INFORMATION: target sequence

<400> SEQUENCE: 305
aaattccatc attgaagaac t                                              21

<210> SEQ ID NO 306
<211> LENGTH: 21
<212> TYPE: DNA
<213> ORGANISM: Artificial Sequence
<220> FEATURE:
<223> OTHER INFORMATION: target sequence

<400> SEQUENCE: 306
aattccatca ttgaagaact a                                              21
```

```
<210> SEQ ID NO 307
<211> LENGTH: 21
<212> TYPE: DNA
<213> ORGANISM: Artificial Sequence
<220> FEATURE:
<223> OTHER INFORMATION: target sequence

<400> SEQUENCE: 307
aagaactaga aaaaaaata g                                          21

<210> SEQ ID NO 308
<211> LENGTH: 21
<212> TYPE: DNA
<213> ORGANISM: Artificial Sequence
<220> FEATURE:
<223> OTHER INFORMATION: target sequence

<400> SEQUENCE: 308
aactagaaaa aaaaatagtg a                                         21

<210> SEQ ID NO 309
<211> LENGTH: 21
<212> TYPE: DNA
<213> ORGANISM: Artificial Sequence
<220> FEATURE:
<223> OTHER INFORMATION: target sequence

<400> SEQUENCE: 309
aaaaaaaaat agtgactgcc a                                         21

<210> SEQ ID NO 310
<211> LENGTH: 21
<212> TYPE: DNA
<213> ORGANISM: Artificial Sequence
<220> FEATURE:
<223> OTHER INFORMATION: target sequence

<400> SEQUENCE: 310
aaaaaaaata gtgactgcca c                                         21

<210> SEQ ID NO 311
<211> LENGTH: 21
<212> TYPE: DNA
<213> ORGANISM: Artificial Sequence
<220> FEATURE:
<223> OTHER INFORMATION: target sequence

<400> SEQUENCE: 311
aaaaaaatag tgactgccac g                                         21

<210> SEQ ID NO 312
<211> LENGTH: 21
<212> TYPE: DNA
<213> ORGANISM: Artificial Sequence
<220> FEATURE:
<223> OTHER INFORMATION: target sequence

<400> SEQUENCE: 312
aaaaaatagt gactgccacg g                                         21

<210> SEQ ID NO 313
<211> LENGTH: 21
<212> TYPE: DNA
<213> ORGANISM: Artificial Sequence
<220> FEATURE:
<223> OTHER INFORMATION: target sequence

<400> SEQUENCE: 313
```
aaaaatagtg actgccacgg t                                    21

<210> SEQ ID NO 314
<211> LENGTH: 21
<212> TYPE: DNA
<213> ORGANISM: Artificial Sequence
<220> FEATURE:
<223> OTHER INFORMATION: target sequence

<400> SEQUENCE: 314
aaaatagtga ctgccacggt g                                    21

<210> SEQ ID NO 315
<211> LENGTH: 21
<212> TYPE: DNA
<213> ORGANISM: Artificial Sequence
<220> FEATURE:
<223> OTHER INFORMATION: target sequence

<400> SEQUENCE: 315
aaatagtgac tgccacggtg a                                    21

<210> SEQ ID NO 316
<211> LENGTH: 21
<212> TYPE: DNA
<213> ORGANISM: Artificial Sequence
<220> FEATURE:
<223> OTHER INFORMATION: target sequence

<400> SEQUENCE: 316
aatagtgact gccacggtga a                                    21

<210> SEQ ID NO 317
<211> LENGTH: 21
<212> TYPE: DNA
<213> ORGANISM: Artificial Sequence
<220> FEATURE:
<223> OTHER INFORMATION: target sequence

<400> SEQUENCE: 317
aataattcag ttcttcaaaa g                                    21

<210> SEQ ID NO 318
<211> LENGTH: 21
<212> TYPE: DNA
<213> ORGANISM: Artificial Sequence
<220> FEATURE:
<223> OTHER INFORMATION: target sequence

<400> SEQUENCE: 318
aattcagttc ttcaaaagca g                                    21

<210> SEQ ID NO 319
<211> LENGTH: 21
<212> TYPE: DNA
<213> ORGANISM: Artificial Sequence
<220> FEATURE:
<223> OTHER INFORMATION: target sequence

<400> SEQUENCE: 319
aaaagcagca acatgatctc a                                    21

<210> SEQ ID NO 320
<211> LENGTH: 21
<212> TYPE: DNA
<213> ORGANISM: Artificial Sequence

```
<220> FEATURE:
<223> OTHER INFORMATION: target sequence

<400> SEQUENCE: 320
aaagcagcaa catgatctca t                                              21

<210> SEQ ID NO 321
<211> LENGTH: 21
<212> TYPE: DNA
<213> ORGANISM: Artificial Sequence
<220> FEATURE:
<223> OTHER INFORMATION: target sequence

<400> SEQUENCE: 321
aagcagcaac atgatctcat g                                              21

<210> SEQ ID NO 322
<211> LENGTH: 21
<212> TYPE: DNA
<213> ORGANISM: Artificial Sequence
<220> FEATURE:
<223> OTHER INFORMATION: target sequence

<400> SEQUENCE: 322
aacatgatct catggagaca g                                              21

<210> SEQ ID NO 323
<211> LENGTH: 21
<212> TYPE: DNA
<213> ORGANISM: Artificial Sequence
<220> FEATURE:
<223> OTHER INFORMATION: target sequence

<400> SEQUENCE: 323
aataacttac tgactatgat g                                              21

<210> SEQ ID NO 324
<211> LENGTH: 21
<212> TYPE: DNA
<213> ORGANISM: Artificial Sequence
<220> FEATURE:
<223> OTHER INFORMATION: target sequence

<400> SEQUENCE: 324
aacttactga ctatgatgtc c                                              21

<210> SEQ ID NO 325
<211> LENGTH: 21
<212> TYPE: DNA
<213> ORGANISM: Artificial Sequence
<220> FEATURE:
<223> OTHER INFORMATION: target sequence

<400> SEQUENCE: 325
aaactcagct aaggacccca c                                              21

<210> SEQ ID NO 326
<211> LENGTH: 21
<212> TYPE: DNA
<213> ORGANISM: Artificial Sequence
<220> FEATURE:
<223> OTHER INFORMATION: target sequence

<400> SEQUENCE: 326
aactcagcta aggaccccac t                                              21
```

-continued

```
<210> SEQ ID NO 327
<211> LENGTH: 21
<212> TYPE: DNA
<213> ORGANISM: Artificial Sequence
<220> FEATURE:
<223> OTHER INFORMATION: target sequence

<400> SEQUENCE: 327
aaggacccca ctgttgctaa a                                              21

<210> SEQ ID NO 328
<211> LENGTH: 21
<212> TYPE: DNA
<213> ORGANISM: Artificial Sequence
<220> FEATURE:
<223> OTHER INFORMATION: target sequence

<400> SEQUENCE: 328
aaagaagaac aaatcagctt c                                              21

<210> SEQ ID NO 329
<211> LENGTH: 21
<212> TYPE: DNA
<213> ORGANISM: Artificial Sequence
<220> FEATURE:
<223> OTHER INFORMATION: target sequence

<400> SEQUENCE: 329
aagaagaaca aatcagcttc a                                              21

<210> SEQ ID NO 330
<211> LENGTH: 21
<212> TYPE: DNA
<213> ORGANISM: Artificial Sequence
<220> FEATURE:
<223> OTHER INFORMATION: target sequence

<400> SEQUENCE: 330
aagaacaaat cagcttcaga g                                              21

<210> SEQ ID NO 331
<211> LENGTH: 21
<212> TYPE: DNA
<213> ORGANISM: Artificial Sequence
<220> FEATURE:
<223> OTHER INFORMATION: target sequence

<400> SEQUENCE: 331
aacaaatcag cttcagagac t                                              21

<210> SEQ ID NO 332
<211> LENGTH: 21
<212> TYPE: DNA
<213> ORGANISM: Artificial Sequence
<220> FEATURE:
<223> OTHER INFORMATION: target sequence

<400> SEQUENCE: 332
aaatcagctt cagagactgt g                                              21

<210> SEQ ID NO 333
<211> LENGTH: 21
<212> TYPE: DNA
<213> ORGANISM: Artificial Sequence
<220> FEATURE:
<223> OTHER INFORMATION: target sequence

<400> SEQUENCE: 333
```
aatcagcttc agagactgtg c                                              21

<210> SEQ ID NO 334
<211> LENGTH: 21
<212> TYPE: DNA
<213> ORGANISM: Artificial Sequence
<220> FEATURE:
<223> OTHER INFORMATION: target sequence

<400> SEQUENCE: 334
aagtattcaa atcaggacac a                                              21

<210> SEQ ID NO 335
<211> LENGTH: 21
<212> TYPE: DNA
<213> ORGANISM: Artificial Sequence
<220> FEATURE:
<223> OTHER INFORMATION: target sequence

<400> SEQUENCE: 335
aaatcaggac acaccacaaa t                                              21

<210> SEQ ID NO 336
<211> LENGTH: 21
<212> TYPE: DNA
<213> ORGANISM: Artificial Sequence
<220> FEATURE:
<223> OTHER INFORMATION: target sequence

<400> SEQUENCE: 336
aatcaggaca caccacaaat g                                              21

<210> SEQ ID NO 337
<211> LENGTH: 21
<212> TYPE: DNA
<213> ORGANISM: Artificial Sequence
<220> FEATURE:
<223> OTHER INFORMATION: target sequence

<400> SEQUENCE: 337
aaatggcatc tacacgttaa c                                              21

<210> SEQ ID NO 338
<211> LENGTH: 21
<212> TYPE: DNA
<213> ORGANISM: Artificial Sequence
<220> FEATURE:
<223> OTHER INFORMATION: target sequence

<400> SEQUENCE: 338
aatggcatct acacgttaac a                                              21

<210> SEQ ID NO 339
<211> LENGTH: 21
<212> TYPE: DNA
<213> ORGANISM: Artificial Sequence
<220> FEATURE:
<223> OTHER INFORMATION: target sequence

<400> SEQUENCE: 339
aacattccct aattctacag a                                              21

<210> SEQ ID NO 340
<211> LENGTH: 21
<212> TYPE: DNA
<213> ORGANISM: Artificial Sequence

```
<220> FEATURE:
<223> OTHER INFORMATION: target sequence

<400> SEQUENCE: 340
aattctacag aagagatcaa g                                              21

<210> SEQ ID NO 341
<211> LENGTH: 21
<212> TYPE: DNA
<213> ORGANISM: Artificial Sequence
<220> FEATURE:
<223> OTHER INFORMATION: target sequence

<400> SEQUENCE: 341
aagagatcaa ggcctactgt g                                              21

<210> SEQ ID NO 342
<211> LENGTH: 21
<212> TYPE: DNA
<213> ORGANISM: Artificial Sequence
<220> FEATURE:
<223> OTHER INFORMATION: target sequence

<400> SEQUENCE: 342
aaggcctact gtgacatgga a                                              21

<210> SEQ ID NO 343
<211> LENGTH: 21
<212> TYPE: DNA
<213> ORGANISM: Artificial Sequence
<220> FEATURE:
<223> OTHER INFORMATION: target sequence

<400> SEQUENCE: 343
aagctggagg aggcgggtgg a                                              21

<210> SEQ ID NO 344
<211> LENGTH: 21
<212> TYPE: DNA
<213> ORGANISM: Artificial Sequence
<220> FEATURE:
<223> OTHER INFORMATION: target sequence

<400> SEQUENCE: 344
aattattcag cgacgtgagg a                                              21

<210> SEQ ID NO 345
<211> LENGTH: 21
<212> TYPE: DNA
<213> ORGANISM: Artificial Sequence
<220> FEATURE:
<223> OTHER INFORMATION: target sequence

<400> SEQUENCE: 345
aaagaatata agtgggattt t                                              21

<210> SEQ ID NO 346
<211> LENGTH: 21
<212> TYPE: DNA
<213> ORGANISM: Artificial Sequence
<220> FEATURE:
<223> OTHER INFORMATION: target sequence

<400> SEQUENCE: 346
aagaatataa agtgggattt g                                              21
```

```
<210> SEQ ID NO 347
<211> LENGTH: 21
<212> TYPE: DNA
<213> ORGANISM: Artificial Sequence
<220> FEATURE:
<223> OTHER INFORMATION: target sequence

<400> SEQUENCE: 347
aatataaagt gggatttggt a                                            21

<210> SEQ ID NO 348
<211> LENGTH: 21
<212> TYPE: DNA
<213> ORGANISM: Artificial Sequence
<220> FEATURE:
<223> OTHER INFORMATION: target sequence

<400> SEQUENCE: 348
aaagtgggat ttggtaaccc t                                            21

<210> SEQ ID NO 349
<211> LENGTH: 21
<212> TYPE: DNA
<213> ORGANISM: Artificial Sequence
<220> FEATURE:
<223> OTHER INFORMATION: target sequence

<400> SEQUENCE: 349
aagtgggatt tggtaaccct t                                            21

<210> SEQ ID NO 350
<211> LENGTH: 21
<212> TYPE: DNA
<213> ORGANISM: Artificial Sequence
<220> FEATURE:
<223> OTHER INFORMATION: target sequence

<400> SEQUENCE: 350
aaccCttcag gagaatattg g                                            21

<210> SEQ ID NO 351
<211> LENGTH: 21
<212> TYPE: DNA
<213> ORGANISM: Artificial Sequence
<220> FEATURE:
<223> OTHER INFORMATION: target sequence

<400> SEQUENCE: 351
aatattggct gggaaatgag t                                            21

<210> SEQ ID NO 352
<211> LENGTH: 21
<212> TYPE: DNA
<213> ORGANISM: Artificial Sequence
<220> FEATURE:
<223> OTHER INFORMATION: target sequence

<400> SEQUENCE: 352
aaatgagttt gtttcgcaac t                                            21

<210> SEQ ID NO 353
<211> LENGTH: 21
<212> TYPE: DNA
<213> ORGANISM: Artificial Sequence
<220> FEATURE:
<223> OTHER INFORMATION: target sequence

<400> SEQUENCE: 353
```
aatgagtttg tttcgcaact g        21

<210> SEQ ID NO 354
<211> LENGTH: 21
<212> TYPE: DNA
<213> ORGANISM: Artificial Sequence
<220> FEATURE:
<223> OTHER INFORMATION: target sequence

<400> SEQUENCE: 354
aactgactaa tcagcaacgc t        21

<210> SEQ ID NO 355
<211> LENGTH: 21
<212> TYPE: DNA
<213> ORGANISM: Artificial Sequence
<220> FEATURE:
<223> OTHER INFORMATION: target sequence

<400> SEQUENCE: 355
aatcagcaac gctatgtgct t        21

<210> SEQ ID NO 356
<211> LENGTH: 21
<212> TYPE: DNA
<213> ORGANISM: Artificial Sequence
<220> FEATURE:
<223> OTHER INFORMATION: target sequence

<400> SEQUENCE: 356
aacgctatgt gcttaaaata c        21

<210> SEQ ID NO 357
<211> LENGTH: 21
<212> TYPE: DNA
<213> ORGANISM: Artificial Sequence
<220> FEATURE:
<223> OTHER INFORMATION: target sequence

<400> SEQUENCE: 357
aaaatacacc ttaaagactg g        21

<210> SEQ ID NO 358
<211> LENGTH: 21
<212> TYPE: DNA
<213> ORGANISM: Artificial Sequence
<220> FEATURE:
<223> OTHER INFORMATION: target sequence

<400> SEQUENCE: 358
aaatacacct taaagactgg g        21

<210> SEQ ID NO 359
<211> LENGTH: 21
<212> TYPE: DNA
<213> ORGANISM: Artificial Sequence
<220> FEATURE:
<223> OTHER INFORMATION: target sequence

<400> SEQUENCE: 359
aatacacctt aaagactggg a        21

<210> SEQ ID NO 360
<211> LENGTH: 21
<212> TYPE: DNA
<213> ORGANISM: Artificial Sequence

```
<220> FEATURE:
<223> OTHER INFORMATION: target sequence

<400> SEQUENCE: 360
aaagactggg aagggaatga g                                              21

<210> SEQ ID NO 361
<211> LENGTH: 21
<212> TYPE: DNA
<213> ORGANISM: Artificial Sequence
<220> FEATURE:
<223> OTHER INFORMATION: target sequence

<400> SEQUENCE: 361
aagactggga agggaatgag g                                              21

<210> SEQ ID NO 362
<211> LENGTH: 21
<212> TYPE: DNA
<213> ORGANISM: Artificial Sequence
<220> FEATURE:
<223> OTHER INFORMATION: target sequence

<400> SEQUENCE: 362
aagggaatga ggcttactca t                                              21

<210> SEQ ID NO 363
<211> LENGTH: 21
<212> TYPE: DNA
<213> ORGANISM: Artificial Sequence
<220> FEATURE:
<223> OTHER INFORMATION: target sequence

<400> SEQUENCE: 363
aatgaggctt actcattgta t                                              21

<210> SEQ ID NO 364
<211> LENGTH: 21
<212> TYPE: DNA
<213> ORGANISM: Artificial Sequence
<220> FEATURE:
<223> OTHER INFORMATION: target sequence

<400> SEQUENCE: 364
aacatttcta tctctcaagt g                                              21

<210> SEQ ID NO 365
<211> LENGTH: 21
<212> TYPE: DNA
<213> ORGANISM: Artificial Sequence
<220> FEATURE:
<223> OTHER INFORMATION: target sequence

<400> SEQUENCE: 365
aagtgaagaa ctcaattata g                                              21

<210> SEQ ID NO 366
<211> LENGTH: 21
<212> TYPE: DNA
<213> ORGANISM: Artificial Sequence
<220> FEATURE:
<223> OTHER INFORMATION: target sequence

<400> SEQUENCE: 366
aagaactcaa ttataggatt c                                              21
```

```
<210> SEQ ID NO 367
<211> LENGTH: 21
<212> TYPE: DNA
<213> ORGANISM: Artificial Sequence
<220> FEATURE:
<223> OTHER INFORMATION: target sequence

<400> SEQUENCE: 367
aactcaatta taggattcac c                                              21

<210> SEQ ID NO 368
<211> LENGTH: 21
<212> TYPE: DNA
<213> ORGANISM: Artificial Sequence
<220> FEATURE:
<223> OTHER INFORMATION: target sequence

<400> SEQUENCE: 368
aattatagga ttcaccttaa a                                              21

<210> SEQ ID NO 369
<211> LENGTH: 21
<212> TYPE: DNA
<213> ORGANISM: Artificial Sequence
<220> FEATURE:
<223> OTHER INFORMATION: target sequence

<400> SEQUENCE: 369
aaaggactta cagggacagc c                                              21

<210> SEQ ID NO 370
<211> LENGTH: 21
<212> TYPE: DNA
<213> ORGANISM: Artificial Sequence
<220> FEATURE:
<223> OTHER INFORMATION: target sequence

<400> SEQUENCE: 370
aaggacttac agggacagcc g                                              21

<210> SEQ ID NO 371
<211> LENGTH: 21
<212> TYPE: DNA
<213> ORGANISM: Artificial Sequence
<220> FEATURE:
<223> OTHER INFORMATION: target sequence

<400> SEQUENCE: 371
aaaataagca gcatcagcca a                                              21

<210> SEQ ID NO 372
<211> LENGTH: 21
<212> TYPE: DNA
<213> ORGANISM: Artificial Sequence
<220> FEATURE:
<223> OTHER INFORMATION: target sequence

<400> SEQUENCE: 372
aaataagcag catcagccaa c                                              21

<210> SEQ ID NO 373
<211> LENGTH: 21
<212> TYPE: DNA
<213> ORGANISM: Artificial Sequence
<220> FEATURE:
<223> OTHER INFORMATION: target sequence

<400> SEQUENCE: 373
```
aataagcagc atcagccaac c								21

<210> SEQ ID NO 374
<211> LENGTH: 21
<212> TYPE: DNA
<213> ORGANISM: Artificial Sequence
<220> FEATURE:
<223> OTHER INFORMATION: target sequence

<400> SEQUENCE: 374
aagcagcatc agccaaccag g								21

<210> SEQ ID NO 375
<211> LENGTH: 21
<212> TYPE: DNA
<213> ORGANISM: Artificial Sequence
<220> FEATURE:
<223> OTHER INFORMATION: target sequence

<400> SEQUENCE: 375
aaccaggaaa tgattttagc a								21

<210> SEQ ID NO 376
<211> LENGTH: 21
<212> TYPE: DNA
<213> ORGANISM: Artificial Sequence
<220> FEATURE:
<223> OTHER INFORMATION: target sequence

<400> SEQUENCE: 376
aaatgatttt agcacaaagg a								21

<210> SEQ ID NO 377
<211> LENGTH: 21
<212> TYPE: DNA
<213> ORGANISM: Artificial Sequence
<220> FEATURE:
<223> OTHER INFORMATION: target sequence

<400> SEQUENCE: 377
aatgatttta gcacaaagga t								21

<210> SEQ ID NO 378
<211> LENGTH: 21
<212> TYPE: DNA
<213> ORGANISM: Artificial Sequence
<220> FEATURE:
<223> OTHER INFORMATION: target sequence

<400> SEQUENCE: 378
aaaggatgga gacaacgaca a								21

<210> SEQ ID NO 379
<211> LENGTH: 21
<212> TYPE: DNA
<213> ORGANISM: Artificial Sequence
<220> FEATURE:
<223> OTHER INFORMATION: target sequence

<400> SEQUENCE: 379
aaggatggag acaacgacaa a								21

<210> SEQ ID NO 380
<211> LENGTH: 21
<212> TYPE: DNA
<213> ORGANISM: Artificial Sequence

```
<220> FEATURE:
<223> OTHER INFORMATION: target sequence

<400> SEQUENCE: 380
aacgacaaat gtatttgcaa a                                              21

<210> SEQ ID NO 381
<211> LENGTH: 21
<212> TYPE: DNA
<213> ORGANISM: Artificial Sequence
<220> FEATURE:
<223> OTHER INFORMATION: target sequence

<400> SEQUENCE: 381
aaatgtattt gcaaatgttc a                                              21

<210> SEQ ID NO 382
<211> LENGTH: 21
<212> TYPE: DNA
<213> ORGANISM: Artificial Sequence
<220> FEATURE:
<223> OTHER INFORMATION: target sequence

<400> SEQUENCE: 382
aatgtatttg caaatgttca c                                              21

<210> SEQ ID NO 383
<211> LENGTH: 21
<212> TYPE: DNA
<213> ORGANISM: Artificial Sequence
<220> FEATURE:
<223> OTHER INFORMATION: target sequence

<400> SEQUENCE: 383
aaatgttcac aaatgctaac a                                              21

<210> SEQ ID NO 384
<211> LENGTH: 21
<212> TYPE: DNA
<213> ORGANISM: Artificial Sequence
<220> FEATURE:
<223> OTHER INFORMATION: target sequence

<400> SEQUENCE: 384
aatgttcaca aatgctaaca g                                              21

<210> SEQ ID NO 385
<211> LENGTH: 21
<212> TYPE: DNA
<213> ORGANISM: Artificial Sequence
<220> FEATURE:
<223> OTHER INFORMATION: target sequence

<400> SEQUENCE: 385
aaatgctaac aggaggctgg t                                              21

<210> SEQ ID NO 386
<211> LENGTH: 21
<212> TYPE: DNA
<213> ORGANISM: Artificial Sequence
<220> FEATURE:
<223> OTHER INFORMATION: target sequence

<400> SEQUENCE: 386
aatgctaaca ggaggctggt g                                              21
```

```
<210> SEQ ID NO 387
<211> LENGTH: 21
<212> TYPE: DNA
<213> ORGANISM: Artificial Sequence
<220> FEATURE:
<223> OTHER INFORMATION: target sequence

<400> SEQUENCE: 387
aacaggaggc tggtggtttg a                                              21

<210> SEQ ID NO 388
<211> LENGTH: 21
<212> TYPE: DNA
<213> ORGANISM: Artificial Sequence
<220> FEATURE:
<223> OTHER INFORMATION: target sequence

<400> SEQUENCE: 388
aacttgaacg gaatgtacta t                                              21

<210> SEQ ID NO 389
<211> LENGTH: 21
<212> TYPE: DNA
<213> ORGANISM: Artificial Sequence
<220> FEATURE:
<223> OTHER INFORMATION: target sequence

<400> SEQUENCE: 389
aacggaatgt actatccaca g                                              21

<210> SEQ ID NO 390
<211> LENGTH: 21
<212> TYPE: DNA
<213> ORGANISM: Artificial Sequence
<220> FEATURE:
<223> OTHER INFORMATION: target sequence

<400> SEQUENCE: 390
aatgtactat ccacagaggc a                                              21

<210> SEQ ID NO 391
<211> LENGTH: 21
<212> TYPE: DNA
<213> ORGANISM: Artificial Sequence
<220> FEATURE:
<223> OTHER INFORMATION: target sequence

<400> SEQUENCE: 391
aacacaaata agttcaacgg c                                              21

<210> SEQ ID NO 392
<211> LENGTH: 21
<212> TYPE: DNA
<213> ORGANISM: Artificial Sequence
<220> FEATURE:
<223> OTHER INFORMATION: target sequence

<400> SEQUENCE: 392
aaataagttc aacggcatta a                                              21

<210> SEQ ID NO 393
<211> LENGTH: 21
<212> TYPE: DNA
<213> ORGANISM: Artificial Sequence
<220> FEATURE:
<223> OTHER INFORMATION: target sequence

<400> SEQUENCE: 393
```
aataagttca acggcattaa a					21

<210> SEQ ID NO 394
<211> LENGTH: 21
<212> TYPE: DNA
<213> ORGANISM: Artificial Sequence
<220> FEATURE:
<223> OTHER INFORMATION: target sequence

<400> SEQUENCE: 394
aagttcaacg gcattaaatg g					21

<210> SEQ ID NO 395
<211> LENGTH: 21
<212> TYPE: DNA
<213> ORGANISM: Artificial Sequence
<220> FEATURE:
<223> OTHER INFORMATION: target sequence

<400> SEQUENCE: 395
aacggcatta aatggtacta c					21

<210> SEQ ID NO 396
<211> LENGTH: 21
<212> TYPE: DNA
<213> ORGANISM: Artificial Sequence
<220> FEATURE:
<223> OTHER INFORMATION: target sequence

<400> SEQUENCE: 396
aaatggtact actggaaagg c					21

<210> SEQ ID NO 397
<211> LENGTH: 21
<212> TYPE: DNA
<213> ORGANISM: Artificial Sequence
<220> FEATURE:
<223> OTHER INFORMATION: target sequence

<400> SEQUENCE: 397
aatggtacta ctggaaaggc t					21

<210> SEQ ID NO 398
<211> LENGTH: 21
<212> TYPE: DNA
<213> ORGANISM: Artificial Sequence
<220> FEATURE:
<223> OTHER INFORMATION: target sequence

<400> SEQUENCE: 398
aaaggctcag gctattcgct c					21

<210> SEQ ID NO 399
<211> LENGTH: 21
<212> TYPE: DNA
<213> ORGANISM: Artificial Sequence
<220> FEATURE:
<223> OTHER INFORMATION: target sequence

<400> SEQUENCE: 399
aaggctcagg ctattcgctc a					21

<210> SEQ ID NO 400
<211> LENGTH: 21
<212> TYPE: DNA
<213> ORGANISM: Artificial Sequence

```
<220> FEATURE:
<223> OTHER INFORMATION: target sequence

<400> SEQUENCE: 400
agcctataac aactttcgga a                                              21

<210> SEQ ID NO 401
<211> LENGTH: 21
<212> TYPE: DNA
<213> ORGANISM: Artificial Sequence
<220> FEATURE:
<223> OTHER INFORMATION: target sequence

<400> SEQUENCE: 401
atcaggtcca gcatgggtcc t                                              21

<210> SEQ ID NO 402
<211> LENGTH: 21
<212> TYPE: DNA
<213> ORGANISM: Artificial Sequence
<220> FEATURE:
<223> OTHER INFORMATION: target sequence

<400> SEQUENCE: 402
gacaactgcc gctcttcctc c                                              21

<210> SEQ ID NO 403
<211> LENGTH: 21
<212> TYPE: DNA
<213> ORGANISM: Artificial Sequence
<220> FEATURE:
<223> OTHER INFORMATION: target sequence

<400> SEQUENCE: 403
ctcgaatacg atgactcggt g                                              21

<210> SEQ ID NO 404
<211> LENGTH: 21
<212> TYPE: DNA
<213> ORGANISM: Artificial Sequence
<220> FEATURE:
<223> OTHER INFORMATION: target sequence

<400> SEQUENCE: 404
tggctaatga agcttgagaa t                                              21

<210> SEQ ID NO 405
<211> LENGTH: 21
<212> TYPE: DNA
<213> ORGANISM: Artificial Sequence
<220> FEATURE:
<223> OTHER INFORMATION: target sequence

<400> SEQUENCE: 405
tccaggacaa catgaagaaa g                                              21

<210> SEQ ID NO 406
<211> LENGTH: 21
<212> TYPE: DNA
<213> ORGANISM: Artificial Sequence
<220> FEATURE:
<223> OTHER INFORMATION: target sequence

<400> SEQUENCE: 406
acggctgtga tgatagaaat a                                              21
```

```
<210> SEQ ID NO 407
<211> LENGTH: 21
<212> TYPE: DNA
<213> ORGANISM: Artificial Sequence
<220> FEATURE:
<223> OTHER INFORMATION: target sequence

<400> SEQUENCE: 407
gcaaacgcgg aagttaactg a                                              21

<210> SEQ ID NO 408
<211> LENGTH: 21
<212> TYPE: DNA
<213> ORGANISM: Artificial Sequence
<220> FEATURE:
<223> OTHER INFORMATION: target sequence

<400> SEQUENCE: 408
cagaccacga gacttgaact t                                              21

<210> SEQ ID NO 409
<211> LENGTH: 21
<212> TYPE: DNA
<213> ORGANISM: Artificial Sequence
<220> FEATURE:
<223> OTHER INFORMATION: target sequence

<400> SEQUENCE: 409
ccagaccagt gaaataaaca a                                              21

<210> SEQ ID NO 410
<211> LENGTH: 21
<212> TYPE: DNA
<213> ORGANISM: Artificial Sequence
<220> FEATURE:
<223> OTHER INFORMATION: target sequence

<400> SEQUENCE: 410
tgcaagataa gaacagtttc c                                              21

<210> SEQ ID NO 411
<211> LENGTH: 21
<212> TYPE: DNA
<213> ORGANISM: Artificial Sequence
<220> FEATURE:
<223> OTHER INFORMATION: target sequence

<400> SEQUENCE: 411
tacagtcaat aaaagaagag a                                              21

<210> SEQ ID NO 412
<211> LENGTH: 21
<212> TYPE: DNA
<213> ORGANISM: Artificial Sequence
<220> FEATURE:
<223> OTHER INFORMATION: target sequence

<400> SEQUENCE: 412
ttagtatcca agcaaaattc c                                              21

<210> SEQ ID NO 413
<211> LENGTH: 21
<212> TYPE: DNA
<213> ORGANISM: Artificial Sequence
<220> FEATURE:
<223> OTHER INFORMATION: target sequence

<400> SEQUENCE: 413
```
actgccacgg tgaataattc a                                      21

<210> SEQ ID NO 414
<211> LENGTH: 21
<212> TYPE: DNA
<213> ORGANISM: Artificial Sequence
<220> FEATURE:
<223> OTHER INFORMATION: target sequence

<400> SEQUENCE: 414
atgatgtcca catcaaactc a                                      21

<210> SEQ ID NO 415
<211> LENGTH: 21
<212> TYPE: DNA
<213> ORGANISM: Artificial Sequence
<220> FEATURE:
<223> OTHER INFORMATION: target sequence

<400> SEQUENCE: 415
gtgctgaagt attcaaatca g                                      21

<210> SEQ ID NO 416
<211> LENGTH: 21
<212> TYPE: DNA
<213> ORGANISM: Artificial Sequence
<220> FEATURE:
<223> OTHER INFORMATION: target sequence

<400> SEQUENCE: 416
gatcaaggcc tactgtgaca t                                      21

<210> SEQ ID NO 417
<211> LENGTH: 21
<212> TYPE: DNA
<213> ORGANISM: Artificial Sequence
<220> FEATURE:
<223> OTHER INFORMATION: target sequence

<400> SEQUENCE: 417
attcagcgac gtgaggatgg c                                      21

<210> SEQ ID NO 418
<211> LENGTH: 21
<212> TYPE: DNA
<213> ORGANISM: Artificial Sequence
<220> FEATURE:
<223> OTHER INFORMATION: target sequence

<400> SEQUENCE: 418
ttcagaggac ttggaaagaa t                                      21

<210> SEQ ID NO 419
<211> LENGTH: 21
<212> TYPE: DNA
<213> ORGANISM: Artificial Sequence
<220> FEATURE:
<223> OTHER INFORMATION: target sequence

<400> SEQUENCE: 419
tcgcaactga ctaatcagca a                                      21

<210> SEQ ID NO 420
<211> LENGTH: 21
<212> TYPE: DNA
<213> ORGANISM: Artificial Sequence

```
<220> FEATURE:
<223> OTHER INFORMATION: target sequence

<400> SEQUENCE: 420
agactgggaa gggaatgagg c                                              21

<210> SEQ ID NO 421
<211> LENGTH: 21
<212> TYPE: DNA
<213> ORGANISM: Artificial Sequence
<220> FEATURE:
<223> OTHER INFORMATION: target sequence

<400> SEQUENCE: 421
actcattgta tgaacatttc t                                              21

<210> SEQ ID NO 422
<211> LENGTH: 21
<212> TYPE: DNA
<213> ORGANISM: Artificial Sequence
<220> FEATURE:
<223> OTHER INFORMATION: target sequence

<400> SEQUENCE: 422
cagccggcaa aataagcagc a                                              21

<210> SEQ ID NO 423
<211> LENGTH: 21
<212> TYPE: DNA
<213> ORGANISM: Artificial Sequence
<220> FEATURE:
<223> OTHER INFORMATION: target sequence

<400> SEQUENCE: 423
tagcacaaag gatggagaca a                                              21

<210> SEQ ID NO 424
<211> LENGTH: 21
<212> TYPE: DNA
<213> ORGANISM: Artificial Sequence
<220> FEATURE:
<223> OTHER INFORMATION: target sequence

<400> SEQUENCE: 424
gttcacaaat gctaacagga g                                              21

<210> SEQ ID NO 425
<211> LENGTH: 21
<212> TYPE: DNA
<213> ORGANISM: Artificial Sequence
<220> FEATURE:
<223> OTHER INFORMATION: target sequence

<400> SEQUENCE: 425
tgtactatcc acagaggcag a                                              21

<210> SEQ ID NO 426
<211> LENGTH: 21
<212> TYPE: DNA
<213> ORGANISM: Artificial Sequence
<220> FEATURE:
<223> OTHER INFORMATION: target sequence

<400> SEQUENCE: 426
cggcattaaa tggtactact g                                              21
```

```
<210> SEQ ID NO 427
<211> LENGTH: 21
<212> TYPE: DNA
<213> ORGANISM: Artificial Sequence
<220> FEATURE:
<223> OTHER INFORMATION: target sequence

<400> SEQUENCE: 427
caaggccaca accatgatga t                                              21

<210> SEQ ID NO 428
<211> LENGTH: 21
<212> TYPE: DNA
<213> ORGANISM: Artificial Sequence
<220> FEATURE:
<223> OTHER INFORMATION: target sequence

<400> SEQUENCE: 428
aactgtggaa ggtgccatgg a                                              21

<210> SEQ ID NO 429
<211> LENGTH: 21
<212> TYPE: DNA
<213> ORGANISM: Artificial Sequence
<220> FEATURE:
<223> OTHER INFORMATION: target sequence

<400> SEQUENCE: 429
aaggtgccat ggacttgatc t                                              21

<210> SEQ ID NO 430
<211> LENGTH: 21
<212> TYPE: DNA
<213> ORGANISM: Artificial Sequence
<220> FEATURE:
<223> OTHER INFORMATION: target sequence

<400> SEQUENCE: 430
aattccctac ctcttgtatc t                                              21

<210> SEQ ID NO 431
<211> LENGTH: 21
<212> TYPE: DNA
<213> ORGANISM: Artificial Sequence
<220> FEATURE:
<223> OTHER INFORMATION: target sequence

<400> SEQUENCE: 431
aaacatctct cacctgcatt g                                              21

<210> SEQ ID NO 432
<211> LENGTH: 21
<212> TYPE: DNA
<213> ORGANISM: Artificial Sequence
<220> FEATURE:
<223> OTHER INFORMATION: target sequence

<400> SEQUENCE: 432
aacatctctc acctgcattg c                                              21

<210> SEQ ID NO 433
<211> LENGTH: 21
<212> TYPE: DNA
<213> ORGANISM: Artificial Sequence
<220> FEATURE:
<223> OTHER INFORMATION: target sequence

<400> SEQUENCE: 433
``` aagggactttgaagccttaat    21

<210> SEQ ID NO 434
<211> LENGTH: 21
<212> TYPE: DNA
<213> ORGANISM: Artificial Sequence
<220> FEATURE:
<223> OTHER INFORMATION: target sequence

<400> SEQUENCE: 434 aagccttaatgaaccagcacc    21

<210> SEQ ID NO 435
<211> LENGTH: 21
<212> TYPE: DNA
<213> ORGANISM: Artificial Sequence
<220> FEATURE:
<223> OTHER INFORMATION: target sequence

<400> SEQUENCE: 435 aatgaaccagcaccaggatcc    21

<210> SEQ ID NO 436
<211> LENGTH: 21
<212> TYPE: DNA
<213> ORGANISM: Artificial Sequence
<220> FEATURE:
<223> OTHER INFORMATION: target sequence

<400> SEQUENCE: 436 aaccagcaccaggatccgctg    21

<210> SEQ ID NO 437
<211> LENGTH: 21
<212> TYPE: DNA
<213> ORGANISM: Artificial Sequence
<220> FEATURE:
<223> OTHER INFORMATION: target sequence

<400> SEQUENCE: 437 aagttactcaagatgtgacca    21

<210> SEQ ID NO 438
<211> LENGTH: 21
<212> TYPE: DNA
<213> ORGANISM: Artificial Sequence
<220> FEATURE:
<223> OTHER INFORMATION: target sequence

<400> SEQUENCE: 438 aagatgtgaccagagaatggg    21

<210> SEQ ID NO 439
<211> LENGTH: 21
<212> TYPE: DNA
<213> ORGANISM: Artificial Sequence
<220> FEATURE:
<223> OTHER INFORMATION: target sequence

<400> SEQUENCE: 439 aatgggctaaaaagttgttt    21

<210> SEQ ID NO 440
<211> LENGTH: 21
<212> TYPE: DNA
<213> ORGANISM: Artificial Sequence

```
<220> FEATURE:
<223> OTHER INFORMATION: target sequence

<400> SEQUENCE: 440
aaaaaagttg tttggaagag a                                              21

<210> SEQ ID NO 441
<211> LENGTH: 21
<212> TYPE: DNA
<213> ORGANISM: Artificial Sequence
<220> FEATURE:
<223> OTHER INFORMATION: target sequence

<400> SEQUENCE: 441
aaaaagttgt ttggaagaga g                                              21

<210> SEQ ID NO 442
<211> LENGTH: 21
<212> TYPE: DNA
<213> ORGANISM: Artificial Sequence
<220> FEATURE:
<223> OTHER INFORMATION: target sequence

<400> SEQUENCE: 442
aaaagttgtt tggaagagag a                                              21

<210> SEQ ID NO 443
<211> LENGTH: 21
<212> TYPE: DNA
<213> ORGANISM: Artificial Sequence
<220> FEATURE:
<223> OTHER INFORMATION: target sequence

<400> SEQUENCE: 443
aaagttgttt ggaagagaga a                                              21

<210> SEQ ID NO 444
<211> LENGTH: 21
<212> TYPE: DNA
<213> ORGANISM: Artificial Sequence
<220> FEATURE:
<223> OTHER INFORMATION: target sequence

<400> SEQUENCE: 444
aagttgtttg gaagagagaa a                                              21

<210> SEQ ID NO 445
<211> LENGTH: 21
<212> TYPE: DNA
<213> ORGANISM: Artificial Sequence
<220> FEATURE:
<223> OTHER INFORMATION: target sequence

<400> SEQUENCE: 445
aagagagaaa aggctagtaa g                                              21

<210> SEQ ID NO 446
<211> LENGTH: 21
<212> TYPE: DNA
<213> ORGANISM: Artificial Sequence
<220> FEATURE:
<223> OTHER INFORMATION: target sequence

<400> SEQUENCE: 446
aaaaggctag taagatcaat g                                              21
```

```
<210> SEQ ID NO 447
<211> LENGTH: 21
<212> TYPE: DNA
<213> ORGANISM: Artificial Sequence
<220> FEATURE:
<223> OTHER INFORMATION: target sequence

<400> SEQUENCE: 447
aaaggctagt aagatcaatg g                                              21

<210> SEQ ID NO 448
<211> LENGTH: 21
<212> TYPE: DNA
<213> ORGANISM: Artificial Sequence
<220> FEATURE:
<223> OTHER INFORMATION: target sequence

<400> SEQUENCE: 448
aaggctagta agatcaatgg t                                              21

<210> SEQ ID NO 449
<211> LENGTH: 21
<212> TYPE: DNA
<213> ORGANISM: Artificial Sequence
<220> FEATURE:
<223> OTHER INFORMATION: target sequence

<400> SEQUENCE: 449
aagatcaatg gtgcttattt c                                              21

<210> SEQ ID NO 450
<211> LENGTH: 21
<212> TYPE: DNA
<213> ORGANISM: Artificial Sequence
<220> FEATURE:
<223> OTHER INFORMATION: target sequence

<400> SEQUENCE: 450
aatggtgctt atttctgtga a                                              21

<210> SEQ ID NO 451
<211> LENGTH: 21
<212> TYPE: DNA
<213> ORGANISM: Artificial Sequence
<220> FEATURE:
<223> OTHER INFORMATION: target sequence

<400> SEQUENCE: 451
aagggcgagt tcgaggagag g                                              21

<210> SEQ ID NO 452
<211> LENGTH: 21
<212> TYPE: DNA
<213> ORGANISM: Artificial Sequence
<220> FEATURE:
<223> OTHER INFORMATION: target sequence

<400> SEQUENCE: 452
aatcaggata cgaaccatga a                                              21

<210> SEQ ID NO 453
<211> LENGTH: 21
<212> TYPE: DNA
<213> ORGANISM: Artificial Sequence
<220> FEATURE:
<223> OTHER INFORMATION: target sequence

<400> SEQUENCE: 453
```
aaccatgaag atgcgtcaac a                                              21

<210> SEQ ID NO 454
<211> LENGTH: 21
<212> TYPE: DNA
<213> ORGANISM: Artificial Sequence
<220> FEATURE:
<223> OTHER INFORMATION: target sequence

<400> SEQUENCE: 454
aagatgcgtc aacaagcttc c                                              21

<210> SEQ ID NO 455
<211> LENGTH: 21
<212> TYPE: DNA
<213> ORGANISM: Artificial Sequence
<220> FEATURE:
<223> OTHER INFORMATION: target sequence

<400> SEQUENCE: 455
aacaagcttc cttcctacca g                                              21

<210> SEQ ID NO 456
<211> LENGTH: 21
<212> TYPE: DNA
<213> ORGANISM: Artificial Sequence
<220> FEATURE:
<223> OTHER INFORMATION: target sequence

<400> SEQUENCE: 456
aagcttcctt cctaccagct a                                              21

<210> SEQ ID NO 457
<211> LENGTH: 21
<212> TYPE: DNA
<213> ORGANISM: Artificial Sequence
<220> FEATURE:
<223> OTHER INFORMATION: target sequence

<400> SEQUENCE: 457
aactatgact gtggacaagg g                                              21

<210> SEQ ID NO 458
<211> LENGTH: 21
<212> TYPE: DNA
<213> ORGANISM: Artificial Sequence
<220> FEATURE:
<223> OTHER INFORMATION: target sequence

<400> SEQUENCE: 458
aagggagata acgtgaacat a                                              21

<210> SEQ ID NO 459
<211> LENGTH: 21
<212> TYPE: DNA
<213> ORGANISM: Artificial Sequence
<220> FEATURE:
<223> OTHER INFORMATION: target sequence

<400> SEQUENCE: 459
aacgtgaaca tatctttcaa a                                              21

<210> SEQ ID NO 460
<211> LENGTH: 21
<212> TYPE: DNA
<213> ORGANISM: Artificial Sequence

```
<220> FEATURE:
<223> OTHER INFORMATION: target sequence

<400> SEQUENCE: 460
aacatatctt tcaaaaggt a                                               21

<210> SEQ ID NO 461
<211> LENGTH: 21
<212> TYPE: DNA
<213> ORGANISM: Artificial Sequence
<220> FEATURE:
<223> OTHER INFORMATION: target sequence

<400> SEQUENCE: 461
aaaaaggtat tgattaaaga a                                              21

<210> SEQ ID NO 462
<211> LENGTH: 21
<212> TYPE: DNA
<213> ORGANISM: Artificial Sequence
<220> FEATURE:
<223> OTHER INFORMATION: target sequence

<400> SEQUENCE: 462
aaaaaggtat tgattaaaga a                                              21

<210> SEQ ID NO 463
<211> LENGTH: 21
<212> TYPE: DNA
<213> ORGANISM: Artificial Sequence
<220> FEATURE:
<223> OTHER INFORMATION: target sequence

<400> SEQUENCE: 463
aaaaggtatt gattaaagaa g                                              21

<210> SEQ ID NO 464
<211> LENGTH: 21
<212> TYPE: DNA
<213> ORGANISM: Artificial Sequence
<220> FEATURE:
<223> OTHER INFORMATION: target sequence

<400> SEQUENCE: 464
aaaggtattg attaaagaag a                                              21

<210> SEQ ID NO 465
<211> LENGTH: 21
<212> TYPE: DNA
<213> ORGANISM: Artificial Sequence
<220> FEATURE:
<223> OTHER INFORMATION: target sequence

<400> SEQUENCE: 465
aaggtattga ttaaagaaga a                                              21

<210> SEQ ID NO 466
<211> LENGTH: 21
<212> TYPE: DNA
<213> ORGANISM: Artificial Sequence
<220> FEATURE:
<223> OTHER INFORMATION: target sequence

<400> SEQUENCE: 466
aaagaagaag atgcagtgat t                                              21
```

```
<210> SEQ ID NO 467
<211> LENGTH: 21
<212> TYPE: DNA
<213> ORGANISM: Artificial Sequence
<220> FEATURE:
<223> OTHER INFORMATION: target sequence

<400> SEQUENCE: 467
aagaagaaga tgcagtgatt t                                          21

<210> SEQ ID NO 468
<211> LENGTH: 21
<212> TYPE: DNA
<213> ORGANISM: Artificial Sequence
<220> FEATURE:
<223> OTHER INFORMATION: target sequence

<400> SEQUENCE: 468
aagaagatgc agtgatttac a                                          21

<210> SEQ ID NO 469
<211> LENGTH: 21
<212> TYPE: DNA
<213> ORGANISM: Artificial Sequence
<220> FEATURE:
<223> OTHER INFORMATION: target sequence

<400> SEQUENCE: 469
aagatgcagt gatttacaaa a                                          21

<210> SEQ ID NO 470
<211> LENGTH: 21
<212> TYPE: DNA
<213> ORGANISM: Artificial Sequence
<220> FEATURE:
<223> OTHER INFORMATION: target sequence

<400> SEQUENCE: 470
aaaaatggtt ccttcatcca t                                          21

<210> SEQ ID NO 471
<211> LENGTH: 21
<212> TYPE: DNA
<213> ORGANISM: Artificial Sequence
<220> FEATURE:
<223> OTHER INFORMATION: target sequence

<400> SEQUENCE: 471
aaaatggttc cttcatccat t                                          21

<210> SEQ ID NO 472
<211> LENGTH: 21
<212> TYPE: DNA
<213> ORGANISM: Artificial Sequence
<220> FEATURE:
<223> OTHER INFORMATION: target sequence

<400> SEQUENCE: 472
aaatggttcc ttcatccatt c                                          21

<210> SEQ ID NO 473
<211> LENGTH: 21
<212> TYPE: DNA
<213> ORGANISM: Artificial Sequence
<220> FEATURE:
<223> OTHER INFORMATION: target sequence

<400> SEQUENCE: 473
```
aatggttcct tcatccattc a         21

<210> SEQ ID NO 474
<211> LENGTH: 21
<212> TYPE: DNA
<213> ORGANISM: Artificial Sequence
<220> FEATURE:
<223> OTHER INFORMATION: target sequence

<400> SEQUENCE: 474
aagtacctga tattctagaa g         21

<210> SEQ ID NO 475
<211> LENGTH: 21
<212> TYPE: DNA
<213> ORGANISM: Artificial Sequence
<220> FEATURE:
<223> OTHER INFORMATION: target sequence

<400> SEQUENCE: 475
aagtacacct gcctcatgct c         21

<210> SEQ ID NO 476
<211> LENGTH: 21
<212> TYPE: DNA
<213> ORGANISM: Artificial Sequence
<220> FEATURE:
<223> OTHER INFORMATION: target sequence

<400> SEQUENCE: 476
aaacctcttc acctcggcct t         21

<210> SEQ ID NO 477
<211> LENGTH: 21
<212> TYPE: DNA
<213> ORGANISM: Artificial Sequence
<220> FEATURE:
<223> OTHER INFORMATION: target sequence

<400> SEQUENCE: 477
aacctcttca cctcggcctt c         21

<210> SEQ ID NO 478
<211> LENGTH: 21
<212> TYPE: DNA
<213> ORGANISM: Artificial Sequence
<220> FEATURE:
<223> OTHER INFORMATION: target sequence

<400> SEQUENCE: 478
aagcccagaa gtggggacct g         21

<210> SEQ ID NO 479
<211> LENGTH: 21
<212> TYPE: DNA
<213> ORGANISM: Artificial Sequence
<220> FEATURE:
<223> OTHER INFORMATION: target sequence

<400> SEQUENCE: 479
aagtggggac ctgaatgcaa c         21

<210> SEQ ID NO 480
<211> LENGTH: 21
<212> TYPE: DNA
<213> ORGANISM: Artificial Sequence

```
<220> FEATURE:
<223> OTHER INFORMATION: target sequence

<400> SEQUENCE: 480
aatgcaacca tctctgtact g                                               21

<210> SEQ ID NO 481
<211> LENGTH: 21
<212> TYPE: DNA
<213> ORGANISM: Artificial Sequence
<220> FEATURE:
<223> OTHER INFORMATION: target sequence

<400> SEQUENCE: 481
aaccatctct gtactgcttg t                                               21

<210> SEQ ID NO 482
<211> LENGTH: 21
<212> TYPE: DNA
<213> ORGANISM: Artificial Sequence
<220> FEATURE:
<223> OTHER INFORMATION: target sequence

<400> SEQUENCE: 482
aacaatggtg tctgccatga a                                               21

<210> SEQ ID NO 483
<211> LENGTH: 21
<212> TYPE: DNA
<213> ORGANISM: Artificial Sequence
<220> FEATURE:
<223> OTHER INFORMATION: target sequence

<400> SEQUENCE: 483
aatggtgtct gccatgaaga t                                               21

<210> SEQ ID NO 484
<211> LENGTH: 21
<212> TYPE: DNA
<213> ORGANISM: Artificial Sequence
<220> FEATURE:
<223> OTHER INFORMATION: target sequence

<400> SEQUENCE: 484
aagatactgg agaatgcatt t                                               21

<210> SEQ ID NO 485
<211> LENGTH: 21
<212> TYPE: DNA
<213> ORGANISM: Artificial Sequence
<220> FEATURE:
<223> OTHER INFORMATION: target sequence

<400> SEQUENCE: 485
aatgcatttg ccctcctggg t                                               21

<210> SEQ ID NO 486
<211> LENGTH: 21
<212> TYPE: DNA
<213> ORGANISM: Artificial Sequence
<220> FEATURE:
<223> OTHER INFORMATION: target sequence

<400> SEQUENCE: 486
aaggacgtgt gagaaggctt g                                               21
```

```
<210> SEQ ID NO 487
<211> LENGTH: 21
<212> TYPE: DNA
<213> ORGANISM: Artificial Sequence
<220> FEATURE:
<223> OTHER INFORMATION: target sequence

<400> SEQUENCE: 487
aaggcttgtg aactgcacac g                                           21

<210> SEQ ID NO 488
<211> LENGTH: 21
<212> TYPE: DNA
<213> ORGANISM: Artificial Sequence
<220> FEATURE:
<223> OTHER INFORMATION: target sequence

<400> SEQUENCE: 488
aactgcacac gtttggcaga a                                           21

<210> SEQ ID NO 489
<211> LENGTH: 21
<212> TYPE: DNA
<213> ORGANISM: Artificial Sequence
<220> FEATURE:
<223> OTHER INFORMATION: target sequence

<400> SEQUENCE: 489
aacttgtaaa gaaaggtgca g                                           21

<210> SEQ ID NO 490
<211> LENGTH: 21
<212> TYPE: DNA
<213> ORGANISM: Artificial Sequence
<220> FEATURE:
<223> OTHER INFORMATION: target sequence

<400> SEQUENCE: 490
aaagaaaggt gcagtggaca a                                           21

<210> SEQ ID NO 491
<211> LENGTH: 21
<212> TYPE: DNA
<213> ORGANISM: Artificial Sequence
<220> FEATURE:
<223> OTHER INFORMATION: target sequence

<400> SEQUENCE: 491
aagaaaggtg cagtggacaa g                                           21

<210> SEQ ID NO 492
<211> LENGTH: 21
<212> TYPE: DNA
<213> ORGANISM: Artificial Sequence
<220> FEATURE:
<223> OTHER INFORMATION: target sequence

<400> SEQUENCE: 492
aaaggtgcag tggacaagag g                                           21

<210> SEQ ID NO 493
<211> LENGTH: 21
<212> TYPE: DNA
<213> ORGANISM: Artificial Sequence
<220> FEATURE:
<223> OTHER INFORMATION: target sequence

<400> SEQUENCE: 493
```
aaggtgcagt ggacaagagg g                                              21

<210> SEQ ID NO 494
<211> LENGTH: 21
<212> TYPE: DNA
<213> ORGANISM: Artificial Sequence
<220> FEATURE:
<223> OTHER INFORMATION: target sequence

<400> SEQUENCE: 494
aagagggatg caagtcttat g                                              21

<210> SEQ ID NO 495
<211> LENGTH: 21
<212> TYPE: DNA
<213> ORGANISM: Artificial Sequence
<220> FEATURE:
<223> OTHER INFORMATION: target sequence

<400> SEQUENCE: 495
aagtcttatg tgttctgtct c                                              21

<210> SEQ ID NO 496
<211> LENGTH: 21
<212> TYPE: DNA
<213> ORGANISM: Artificial Sequence
<220> FEATURE:
<223> OTHER INFORMATION: target sequence

<400> SEQUENCE: 496
aagggtctgc agtgcaatga a                                              21

<210> SEQ ID NO 497
<211> LENGTH: 21
<212> TYPE: DNA
<213> ORGANISM: Artificial Sequence
<220> FEATURE:
<223> OTHER INFORMATION: target sequence

<400> SEQUENCE: 497
aatgaagcat gccaccctgg t                                              21

<210> SEQ ID NO 498
<211> LENGTH: 21
<212> TYPE: DNA
<213> ORGANISM: Artificial Sequence
<220> FEATURE:
<223> OTHER INFORMATION: target sequence

<400> SEQUENCE: 498
aagcatgcca ccctggtttt t                                              21

<210> SEQ ID NO 499
<211> LENGTH: 21
<212> TYPE: DNA
<213> ORGANISM: Artificial Sequence
<220> FEATURE:
<223> OTHER INFORMATION: target sequence

<400> SEQUENCE: 499
aagcttaggt gcagctgcaa c                                              21

<210> SEQ ID NO 500
<211> LENGTH: 21
<212> TYPE: DNA
<213> ORGANISM: Artificial Sequence

```
<220> FEATURE:
<223> OTHER INFORMATION: target sequence

<400> SEQUENCE: 500
aacaatgggg agatgtgtga t                                              21

<210> SEQ ID NO 501
<211> LENGTH: 21
<212> TYPE: DNA
<213> ORGANISM: Artificial Sequence
<220> FEATURE:
<223> OTHER INFORMATION: target sequence

<400> SEQUENCE: 501
aatggggaga tgtgtgatcg c                                              21

<210> SEQ ID NO 502
<211> LENGTH: 21
<212> TYPE: DNA
<213> ORGANISM: Artificial Sequence
<220> FEATURE:
<223> OTHER INFORMATION: target sequence

<400> SEQUENCE: 502
aaggatgtct ctgctctcca g                                              21

<210> SEQ ID NO 503
<211> LENGTH: 21
<212> TYPE: DNA
<213> ORGANISM: Artificial Sequence
<220> FEATURE:
<223> OTHER INFORMATION: target sequence

<400> SEQUENCE: 503
aaggcatacc gaggatgacc c                                              21

<210> SEQ ID NO 504
<211> LENGTH: 21
<212> TYPE: DNA
<213> ORGANISM: Artificial Sequence
<220> FEATURE:
<223> OTHER INFORMATION: target sequence

<400> SEQUENCE: 504
aaagatagtg gatttgccag a                                              21

<210> SEQ ID NO 505
<211> LENGTH: 21
<212> TYPE: DNA
<213> ORGANISM: Artificial Sequence
<220> FEATURE:
<223> OTHER INFORMATION: target sequence

<400> SEQUENCE: 505
aagatagtgg atttgccaga t                                              21

<210> SEQ ID NO 506
<211> LENGTH: 21
<212> TYPE: DNA
<213> ORGANISM: Artificial Sequence
<220> FEATURE:
<223> OTHER INFORMATION: target sequence

<400> SEQUENCE: 506
aagtaaacag tggtaaattt a                                              21
```

```
<210> SEQ ID NO 507
<211> LENGTH: 21
<212> TYPE: DNA
<213> ORGANISM: Artificial Sequence
<220> FEATURE:
<223> OTHER INFORMATION: target sequence

<400> SEQUENCE: 507
aaacagtggt aaatttaatc c                                              21

<210> SEQ ID NO 508
<211> LENGTH: 21
<212> TYPE: DNA
<213> ORGANISM: Artificial Sequence
<220> FEATURE:
<223> OTHER INFORMATION: target sequence

<400> SEQUENCE: 508
aacagtggta aatttaatcc c                                              21

<210> SEQ ID NO 509
<211> LENGTH: 21
<212> TYPE: DNA
<213> ORGANISM: Artificial Sequence
<220> FEATURE:
<223> OTHER INFORMATION: target sequence

<400> SEQUENCE: 509
aaatttaatc ccatttgcaa a                                              21

<210> SEQ ID NO 510
<211> LENGTH: 21
<212> TYPE: DNA
<213> ORGANISM: Artificial Sequence
<220> FEATURE:
<223> OTHER INFORMATION: target sequence

<400> SEQUENCE: 510
aatttaatcc catttgcaaa g                                              21

<210> SEQ ID NO 511
<211> LENGTH: 21
<212> TYPE: DNA
<213> ORGANISM: Artificial Sequence
<220> FEATURE:
<223> OTHER INFORMATION: target sequence

<400> SEQUENCE: 511
aatcccattt gcaaagcttc t                                              21

<210> SEQ ID NO 512
<211> LENGTH: 21
<212> TYPE: DNA
<213> ORGANISM: Artificial Sequence
<220> FEATURE:
<223> OTHER INFORMATION: target sequence

<400> SEQUENCE: 512
aaagcttctg gctggccgct a                                              21

<210> SEQ ID NO 513
<211> LENGTH: 21
<212> TYPE: DNA
<213> ORGANISM: Artificial Sequence
<220> FEATURE:
<223> OTHER INFORMATION: target sequence

<400> SEQUENCE: 513
```

```
aagcttctgg ctggccgcta c                                              21

<210> SEQ ID NO 514
<211> LENGTH: 21
<212> TYPE: DNA
<213> ORGANISM: Artificial Sequence
<220> FEATURE:
<223> OTHER INFORMATION: target sequence

<400> SEQUENCE: 514
aatgaagaaa tgaccctggt g                                              21

<210> SEQ ID NO 515
<211> LENGTH: 21
<212> TYPE: DNA
<213> ORGANISM: Artificial Sequence
<220> FEATURE:
<223> OTHER INFORMATION: target sequence

<400> SEQUENCE: 515
aagaaatgac cctggtgaag c                                              21

<210> SEQ ID NO 516
<211> LENGTH: 21
<212> TYPE: DNA
<213> ORGANISM: Artificial Sequence
<220> FEATURE:
<223> OTHER INFORMATION: target sequence

<400> SEQUENCE: 516
aaatgaccct ggtgaagccg g                                              21

<210> SEQ ID NO 517
<211> LENGTH: 21
<212> TYPE: DNA
<213> ORGANISM: Artificial Sequence
<220> FEATURE:
<223> OTHER INFORMATION: target sequence

<400> SEQUENCE: 517
aatgaccctg gtgaagccgg a                                              21

<210> SEQ ID NO 518
<211> LENGTH: 21
<212> TYPE: DNA
<213> ORGANISM: Artificial Sequence
<220> FEATURE:
<223> OTHER INFORMATION: target sequence

<400> SEQUENCE: 518
aagccggatg ggacagtgct c                                              21

<210> SEQ ID NO 519
<211> LENGTH: 21
<212> TYPE: DNA
<213> ORGANISM: Artificial Sequence
<220> FEATURE:
<223> OTHER INFORMATION: target sequence

<400> SEQUENCE: 519
aaaagacttt aaccatacgg a                                              21

<210> SEQ ID NO 520
<211> LENGTH: 21
<212> TYPE: DNA
<213> ORGANISM: Artificial Sequence
```

```
<220> FEATURE:
<223> OTHER INFORMATION: target sequence

<400> SEQUENCE: 520
aaagacttta accatacgga t                                              21

<210> SEQ ID NO 521
<211> LENGTH: 21
<212> TYPE: DNA
<213> ORGANISM: Artificial Sequence
<220> FEATURE:
<223> OTHER INFORMATION: target sequence

<400> SEQUENCE: 521
aagactttaa ccatacggat c                                              21

<210> SEQ ID NO 522
<211> LENGTH: 21
<212> TYPE: DNA
<213> ORGANISM: Artificial Sequence
<220> FEATURE:
<223> OTHER INFORMATION: target sequence

<400> SEQUENCE: 522
aaccatacgg atcatttctc a                                              21

<210> SEQ ID NO 523
<211> LENGTH: 21
<212> TYPE: DNA
<213> ORGANISM: Artificial Sequence
<220> FEATURE:
<223> OTHER INFORMATION: target sequence

<400> SEQUENCE: 523
aacacagtgg ctgggatggt g                                              21

<210> SEQ ID NO 524
<211> LENGTH: 21
<212> TYPE: DNA
<213> ORGANISM: Artificial Sequence
<220> FEATURE:
<223> OTHER INFORMATION: target sequence

<400> SEQUENCE: 524
aaaagccctt caacatttct g                                              21

<210> SEQ ID NO 525
<211> LENGTH: 21
<212> TYPE: DNA
<213> ORGANISM: Artificial Sequence
<220> FEATURE:
<223> OTHER INFORMATION: target sequence

<400> SEQUENCE: 525
aaagcccttc aacatttctg t                                              21

<210> SEQ ID NO 526
<211> LENGTH: 21
<212> TYPE: DNA
<213> ORGANISM: Artificial Sequence
<220> FEATURE:
<223> OTHER INFORMATION: target sequence

<400> SEQUENCE: 526
aagcccttca acatttctgt t                                              21
```

<210> SEQ ID NO 527
<211> LENGTH: 21
<212> TYPE: DNA
<213> ORGANISM: Artificial Sequence
<220> FEATURE:
<223> OTHER INFORMATION: target sequence

<400> SEQUENCE: 527
aacatttctg ttaaagttct t                                              21

<210> SEQ ID NO 528
<211> LENGTH: 21
<212> TYPE: DNA
<213> ORGANISM: Artificial Sequence
<220> FEATURE:
<223> OTHER INFORMATION: target sequence

<400> SEQUENCE: 528
aaagttcttc caaagcccct g                                              21

<210> SEQ ID NO 529
<211> LENGTH: 21
<212> TYPE: DNA
<213> ORGANISM: Artificial Sequence
<220> FEATURE:
<223> OTHER INFORMATION: target sequence

<400> SEQUENCE: 529
aagttcttcc aaagccctg a                                               21

<210> SEQ ID NO 530
<211> LENGTH: 21
<212> TYPE: DNA
<213> ORGANISM: Artificial Sequence
<220> FEATURE:
<223> OTHER INFORMATION: target sequence

<400> SEQUENCE: 530
aaagcccctg aatgccccaa a                                              21

<210> SEQ ID NO 531
<211> LENGTH: 21
<212> TYPE: DNA
<213> ORGANISM: Artificial Sequence
<220> FEATURE:
<223> OTHER INFORMATION: target sequence

<400> SEQUENCE: 531
aagcccctga atgccccaaa c                                              21

<210> SEQ ID NO 532
<211> LENGTH: 21
<212> TYPE: DNA
<213> ORGANISM: Artificial Sequence
<220> FEATURE:
<223> OTHER INFORMATION: target sequence

<400> SEQUENCE: 532
aatgccccaa acgtgattga c                                              21

<210> SEQ ID NO 533
<211> LENGTH: 21
<212> TYPE: DNA
<213> ORGANISM: Artificial Sequence
<220> FEATURE:
<223> OTHER INFORMATION: target sequence

<400> SEQUENCE: 533

```
aaacgtgatt gacactggac a                                              21

<210> SEQ ID NO 534
<211> LENGTH: 21
<212> TYPE: DNA
<213> ORGANISM: Artificial Sequence
<220> FEATURE:
<223> OTHER INFORMATION: target sequence

<400> SEQUENCE: 534
aacgtgattg acactggaca t                                              21

<210> SEQ ID NO 535
<211> LENGTH: 21
<212> TYPE: DNA
<213> ORGANISM: Artificial Sequence
<220> FEATURE:
<223> OTHER INFORMATION: target sequence

<400> SEQUENCE: 535
aactttgctg tcatcaacat c                                              21

<210> SEQ ID NO 536
<211> LENGTH: 21
<212> TYPE: DNA
<213> ORGANISM: Artificial Sequence
<220> FEATURE:
<223> OTHER INFORMATION: target sequence

<400> SEQUENCE: 536
aatcaaatcc aagaagcttc t                                              21

<210> SEQ ID NO 537
<211> LENGTH: 21
<212> TYPE: DNA
<213> ORGANISM: Artificial Sequence
<220> FEATURE:
<223> OTHER INFORMATION: target sequence

<400> SEQUENCE: 537
aaatccaaga agcttctata c                                              21

<210> SEQ ID NO 538
<211> LENGTH: 21
<212> TYPE: DNA
<213> ORGANISM: Artificial Sequence
<220> FEATURE:
<223> OTHER INFORMATION: target sequence

<400> SEQUENCE: 538
aatccaagaa gcttctatac a                                              21

<210> SEQ ID NO 539
<211> LENGTH: 21
<212> TYPE: DNA
<213> ORGANISM: Artificial Sequence
<220> FEATURE:
<223> OTHER INFORMATION: target sequence

<400> SEQUENCE: 539
aagaagcttc tatacaaacc c                                              21

<210> SEQ ID NO 540
<211> LENGTH: 21
<212> TYPE: DNA
<213> ORGANISM: Artificial Sequence
```

```
<220> FEATURE:
<223> OTHER INFORMATION: target sequence

<400> SEQUENCE: 540
aagcttctat acaaacccgt t                                              21

<210> SEQ ID NO 541
<211> LENGTH: 21
<212> TYPE: DNA
<213> ORGANISM: Artificial Sequence
<220> FEATURE:
<223> OTHER INFORMATION: target sequence

<400> SEQUENCE: 541
aaacccgtta atcactatga g                                              21

<210> SEQ ID NO 542
<211> LENGTH: 21
<212> TYPE: DNA
<213> ORGANISM: Artificial Sequence
<220> FEATURE:
<223> OTHER INFORMATION: target sequence

<400> SEQUENCE: 542
aacccgttaa tcactatgag g                                              21

<210> SEQ ID NO 543
<211> LENGTH: 21
<212> TYPE: DNA
<213> ORGANISM: Artificial Sequence
<220> FEATURE:
<223> OTHER INFORMATION: target sequence

<400> SEQUENCE: 543
aatcactatg aggcttggca a                                              21

<210> SEQ ID NO 544
<211> LENGTH: 21
<212> TYPE: DNA
<213> ORGANISM: Artificial Sequence
<220> FEATURE:
<223> OTHER INFORMATION: target sequence

<400> SEQUENCE: 544
aacatattca agtgacaaat g                                              21

<210> SEQ ID NO 545
<211> LENGTH: 21
<212> TYPE: DNA
<213> ORGANISM: Artificial Sequence
<220> FEATURE:
<223> OTHER INFORMATION: target sequence

<400> SEQUENCE: 545
aagtgacaaa tgagattgtt a                                              21

<210> SEQ ID NO 546
<211> LENGTH: 21
<212> TYPE: DNA
<213> ORGANISM: Artificial Sequence
<220> FEATURE:
<223> OTHER INFORMATION: target sequence

<400> SEQUENCE: 546
aaatgagatt gttacactca a                                              21
```

```
<210> SEQ ID NO 547
<211> LENGTH: 21
<212> TYPE: DNA
<213> ORGANISM: Artificial Sequence
<220> FEATURE:
<223> OTHER INFORMATION: target sequence

<400> SEQUENCE: 547
aatgagattg ttacactcaa c                                              21

<210> SEQ ID NO 548
<211> LENGTH: 21
<212> TYPE: DNA
<213> ORGANISM: Artificial Sequence
<220> FEATURE:
<223> OTHER INFORMATION: target sequence

<400> SEQUENCE: 548
aactatttgg aacctcggac a                                              21

<210> SEQ ID NO 549
<211> LENGTH: 21
<212> TYPE: DNA
<213> ORGANISM: Artificial Sequence
<220> FEATURE:
<223> OTHER INFORMATION: target sequence

<400> SEQUENCE: 549
aacctcggac agaatatgaa c                                              21

<210> SEQ ID NO 550
<211> LENGTH: 21
<212> TYPE: DNA
<213> ORGANISM: Artificial Sequence
<220> FEATURE:
<223> OTHER INFORMATION: target sequence

<400> SEQUENCE: 550
aatatgaact ctgtgtgcaa c                                              21

<210> SEQ ID NO 551
<211> LENGTH: 21
<212> TYPE: DNA
<213> ORGANISM: Artificial Sequence
<220> FEATURE:
<223> OTHER INFORMATION: target sequence

<400> SEQUENCE: 551
aactctgtgt gcaactggtc c                                              21

<210> SEQ ID NO 552
<211> LENGTH: 21
<212> TYPE: DNA
<213> ORGANISM: Artificial Sequence
<220> FEATURE:
<223> OTHER INFORMATION: target sequence

<400> SEQUENCE: 552
aactggtccg tcgtggagag g                                              21

<210> SEQ ID NO 553
<211> LENGTH: 21
<212> TYPE: DNA
<213> ORGANISM: Artificial Sequence
<220> FEATURE:
<223> OTHER INFORMATION: target sequence

<400> SEQUENCE: 553
```
aagggcatcc tggacctgtg a                                              21

<210> SEQ ID NO 554
<211> LENGTH: 21
<212> TYPE: DNA
<213> ORGANISM: Artificial Sequence
<220> FEATURE:
<223> OTHER INFORMATION: target sequence

<400> SEQUENCE: 554
aacagcttct atcggactcc c                                              21

<210> SEQ ID NO 555
<211> LENGTH: 21
<212> TYPE: DNA
<213> ORGANISM: Artificial Sequence
<220> FEATURE:
<223> OTHER INFORMATION: target sequence

<400> SEQUENCE: 555
aagaggtcta aatctcctgc c                                              21

<210> SEQ ID NO 556
<211> LENGTH: 21
<212> TYPE: DNA
<213> ORGANISM: Artificial Sequence
<220> FEATURE:
<223> OTHER INFORMATION: target sequence

<400> SEQUENCE: 556
aaatctcctg cctaaaagtc a                                              21

<210> SEQ ID NO 557
<211> LENGTH: 21
<212> TYPE: DNA
<213> ORGANISM: Artificial Sequence
<220> FEATURE:
<223> OTHER INFORMATION: target sequence

<400> SEQUENCE: 557
aatctcctgc ctaaaagtca g                                              21

<210> SEQ ID NO 558
<211> LENGTH: 21
<212> TYPE: DNA
<213> ORGANISM: Artificial Sequence
<220> FEATURE:
<223> OTHER INFORMATION: target sequence

<400> SEQUENCE: 558
aaaagtcaga ccactctaaa t                                              21

<210> SEQ ID NO 559
<211> LENGTH: 21
<212> TYPE: DNA
<213> ORGANISM: Artificial Sequence
<220> FEATURE:
<223> OTHER INFORMATION: target sequence

<400> SEQUENCE: 559
aaagtcagac cactctaaat t                                              21

<210> SEQ ID NO 560
<211> LENGTH: 21
<212> TYPE: DNA
<213> ORGANISM: Artificial Sequence

```
<220> FEATURE:
<223> OTHER INFORMATION: target sequence

<400> SEQUENCE: 560
aagtcagacc actctaaatt t                                              21

<210> SEQ ID NO 561
<211> LENGTH: 21
<212> TYPE: DNA
<213> ORGANISM: Artificial Sequence
<220> FEATURE:
<223> OTHER INFORMATION: target sequence

<400> SEQUENCE: 561
aaatttgacc tggcaaccaa t                                              21

<210> SEQ ID NO 562
<211> LENGTH: 21
<212> TYPE: DNA
<213> ORGANISM: Artificial Sequence
<220> FEATURE:
<223> OTHER INFORMATION: target sequence

<400> SEQUENCE: 562
aatttgacct ggcaaccaat a                                              21

<210> SEQ ID NO 563
<211> LENGTH: 21
<212> TYPE: DNA
<213> ORGANISM: Artificial Sequence
<220> FEATURE:
<223> OTHER INFORMATION: target sequence

<400> SEQUENCE: 563
aaccaatatt tccaagctcg g                                              21

<210> SEQ ID NO 564
<211> LENGTH: 21
<212> TYPE: DNA
<213> ORGANISM: Artificial Sequence
<220> FEATURE:
<223> OTHER INFORMATION: target sequence

<400> SEQUENCE: 564
aatatttcca agctcggaag a                                              21

<210> SEQ ID NO 565
<211> LENGTH: 21
<212> TYPE: DNA
<213> ORGANISM: Artificial Sequence
<220> FEATURE:
<223> OTHER INFORMATION: target sequence

<400> SEQUENCE: 565
aagctcggaa gatgactttt a                                              21

<210> SEQ ID NO 566
<211> LENGTH: 21
<212> TYPE: DNA
<213> ORGANISM: Artificial Sequence
<220> FEATURE:
<223> OTHER INFORMATION: target sequence

<400> SEQUENCE: 566
aagatgactt ttatgttgaa g                                              21
```

<210> SEQ ID NO 567
<211> LENGTH: 21
<212> TYPE: DNA
<213> ORGANISM: Artificial Sequence
<220> FEATURE:
<223> OTHER INFORMATION: target sequence

<400> SEQUENCE: 567
aagtggagag aaggtctgtg c                                      21

<210> SEQ ID NO 568
<211> LENGTH: 21
<212> TYPE: DNA
<213> ORGANISM: Artificial Sequence
<220> FEATURE:
<223> OTHER INFORMATION: target sequence

<400> SEQUENCE: 568
aaggtctgtg caaaaaagtg a                                      21

<210> SEQ ID NO 569
<211> LENGTH: 21
<212> TYPE: DNA
<213> ORGANISM: Artificial Sequence
<220> FEATURE:
<223> OTHER INFORMATION: target sequence

<400> SEQUENCE: 569
aaaaaagtga tcagcagaat a                                      21

<210> SEQ ID NO 570
<211> LENGTH: 21
<212> TYPE: DNA
<213> ORGANISM: Artificial Sequence
<220> FEATURE:
<223> OTHER INFORMATION: target sequence

<400> SEQUENCE: 570
aaaaagtgat cagcagaata t                                      21

<210> SEQ ID NO 571
<211> LENGTH: 21
<212> TYPE: DNA
<213> ORGANISM: Artificial Sequence
<220> FEATURE:
<223> OTHER INFORMATION: target sequence

<400> SEQUENCE: 571
aaaagtgatc agcagaatat t                                      21

<210> SEQ ID NO 572
<211> LENGTH: 21
<212> TYPE: DNA
<213> ORGANISM: Artificial Sequence
<220> FEATURE:
<223> OTHER INFORMATION: target sequence

<400> SEQUENCE: 572
aaagtgatca gcagaatatt a                                      21

<210> SEQ ID NO 573
<211> LENGTH: 21
<212> TYPE: DNA
<213> ORGANISM: Artificial Sequence
<220> FEATURE:
<223> OTHER INFORMATION: target sequence

<400> SEQUENCE: 573
aagtgatcag cagaatatta a                                              21

<210> SEQ ID NO 574
<211> LENGTH: 21
<212> TYPE: DNA
<213> ORGANISM: Artificial Sequence
<220> FEATURE:
<223> OTHER INFORMATION: target sequence

<400> SEQUENCE: 574
aatattaaag ttccaggcaa c                                              21

<210> SEQ ID NO 575
<211> LENGTH: 21
<212> TYPE: DNA
<213> ORGANISM: Artificial Sequence
<220> FEATURE:
<223> OTHER INFORMATION: target sequence

<400> SEQUENCE: 575
aaagttccag gcaacttgac t                                              21

<210> SEQ ID NO 576
<211> LENGTH: 21
<212> TYPE: DNA
<213> ORGANISM: Artificial Sequence
<220> FEATURE:
<223> OTHER INFORMATION: target sequence

<400> SEQUENCE: 576
aagttccagg caacttgact t                                              21

<210> SEQ ID NO 577
<211> LENGTH: 21
<212> TYPE: DNA
<213> ORGANISM: Artificial Sequence
<220> FEATURE:
<223> OTHER INFORMATION: target sequence

<400> SEQUENCE: 577
aacttgactt cggtgctact t                                              21

<210> SEQ ID NO 578
<211> LENGTH: 21
<212> TYPE: DNA
<213> ORGANISM: Artificial Sequence
<220> FEATURE:
<223> OTHER INFORMATION: target sequence

<400> SEQUENCE: 578
aacaacttac atcccaggga g                                              21

<210> SEQ ID NO 579
<211> LENGTH: 21
<212> TYPE: DNA
<213> ORGANISM: Artificial Sequence
<220> FEATURE:
<223> OTHER INFORMATION: target sequence

<400> SEQUENCE: 579
aacttacatc ccagggagca g                                              21

<210> SEQ ID NO 580
<211> LENGTH: 21
<212> TYPE: DNA
<213> ORGANISM: Artificial Sequence

```
<220> FEATURE:
<223> OTHER INFORMATION: target sequence

<400> SEQUENCE: 580
aacaccaagg cccaggggga a                                              21

<210> SEQ ID NO 581
<211> LENGTH: 21
<212> TYPE: DNA
<213> ORGANISM: Artificial Sequence
<220> FEATURE:
<223> OTHER INFORMATION: target sequence

<400> SEQUENCE: 581
aaggcccagg gggaatggag t                                              21

<210> SEQ ID NO 582
<211> LENGTH: 21
<212> TYPE: DNA
<213> ORGANISM: Artificial Sequence
<220> FEATURE:
<223> OTHER INFORMATION: target sequence

<400> SEQUENCE: 582
aatggagtga agatctcact g                                              21

<210> SEQ ID NO 583
<211> LENGTH: 21
<212> TYPE: DNA
<213> ORGANISM: Artificial Sequence
<220> FEATURE:
<223> OTHER INFORMATION: target sequence

<400> SEQUENCE: 583
aagatctcac tgcttggacc c                                              21

<210> SEQ ID NO 584
<211> LENGTH: 21
<212> TYPE: DNA
<213> ORGANISM: Artificial Sequence
<220> FEATURE:
<223> OTHER INFORMATION: target sequence

<400> SEQUENCE: 584
aaccagaaaa catcaagatt t                                              21

<210> SEQ ID NO 585
<211> LENGTH: 21
<212> TYPE: DNA
<213> ORGANISM: Artificial Sequence
<220> FEATURE:
<223> OTHER INFORMATION: target sequence

<400> SEQUENCE: 585
aaaacatcaa gatttccaac a                                              21

<210> SEQ ID NO 586
<211> LENGTH: 21
<212> TYPE: DNA
<213> ORGANISM: Artificial Sequence
<220> FEATURE:
<223> OTHER INFORMATION: target sequence

<400> SEQUENCE: 586
aaacatcaag atttccaaca t                                              21
```

```
<210> SEQ ID NO 587
<211> LENGTH: 21
<212> TYPE: DNA
<213> ORGANISM: Artificial Sequence
<220> FEATURE:
<223> OTHER INFORMATION: target sequence

<400> SEQUENCE: 587
aacatcaaga tttccaacat t                                              21

<210> SEQ ID NO 588
<211> LENGTH: 21
<212> TYPE: DNA
<213> ORGANISM: Artificial Sequence
<220> FEATURE:
<223> OTHER INFORMATION: target sequence

<400> SEQUENCE: 588
aagatttcca acattacaca c                                              21

<210> SEQ ID NO 589
<211> LENGTH: 21
<212> TYPE: DNA
<213> ORGANISM: Artificial Sequence
<220> FEATURE:
<223> OTHER INFORMATION: target sequence

<400> SEQUENCE: 589
aacattacac actcctcggc t                                              21

<210> SEQ ID NO 590
<211> LENGTH: 21
<212> TYPE: DNA
<213> ORGANISM: Artificial Sequence
<220> FEATURE:
<223> OTHER INFORMATION: target sequence

<400> SEQUENCE: 590
aatattggat ggctattcta t                                              21

<210> SEQ ID NO 591
<211> LENGTH: 21
<212> TYPE: DNA
<213> ORGANISM: Artificial Sequence
<220> FEATURE:
<223> OTHER INFORMATION: target sequence

<400> SEQUENCE: 591
aaggttcaag gcaagaatga a                                              21

<210> SEQ ID NO 592
<211> LENGTH: 21
<212> TYPE: DNA
<213> ORGANISM: Artificial Sequence
<220> FEATURE:
<223> OTHER INFORMATION: target sequence

<400> SEQUENCE: 592
aaggcaagaa tgaagaccag c                                              21

<210> SEQ ID NO 593
<211> LENGTH: 21
<212> TYPE: DNA
<213> ORGANISM: Artificial Sequence
<220> FEATURE:
<223> OTHER INFORMATION: target sequence

<400> SEQUENCE: 593
```
aagaatgaag accagcacgt t                                              21

<210> SEQ ID NO 594
<211> LENGTH: 21
<212> TYPE: DNA
<213> ORGANISM: Artificial Sequence
<220> FEATURE:
<223> OTHER INFORMATION: target sequence

<400> SEQUENCE: 594
aatgaagacc agcacgttga t                                              21

<210> SEQ ID NO 595
<211> LENGTH: 21
<212> TYPE: DNA
<213> ORGANISM: Artificial Sequence
<220> FEATURE:
<223> OTHER INFORMATION: target sequence

<400> SEQUENCE: 595
aagaccagca cgttgatgtg a                                              21

<210> SEQ ID NO 596
<211> LENGTH: 21
<212> TYPE: DNA
<213> ORGANISM: Artificial Sequence
<220> FEATURE:
<223> OTHER INFORMATION: target sequence

<400> SEQUENCE: 596
aagataaaga atgccaccat c                                              21

<210> SEQ ID NO 597
<211> LENGTH: 21
<212> TYPE: DNA
<213> ORGANISM: Artificial Sequence
<220> FEATURE:
<223> OTHER INFORMATION: target sequence

<400> SEQUENCE: 597
aaagaatgcc accatcattc a                                              21

<210> SEQ ID NO 598
<211> LENGTH: 21
<212> TYPE: DNA
<213> ORGANISM: Artificial Sequence
<220> FEATURE:
<223> OTHER INFORMATION: target sequence

<400> SEQUENCE: 598
aagaatgcca ccatcattca g                                              21

<210> SEQ ID NO 599
<211> LENGTH: 21
<212> TYPE: DNA
<213> ORGANISM: Artificial Sequence
<220> FEATURE:
<223> OTHER INFORMATION: target sequence

<400> SEQUENCE: 599
aatgccacca tcattcagta t                                              21

<210> SEQ ID NO 600
<211> LENGTH: 21
<212> TYPE: DNA
<213> ORGANISM: Artificial Sequence

```
<220> FEATURE:
<223> OTHER INFORMATION: target sequence

<400> SEQUENCE: 600
aagggcctag agcctgaaac a                                              21

<210> SEQ ID NO 601
<211> LENGTH: 21
<212> TYPE: DNA
<213> ORGANISM: Artificial Sequence
<220> FEATURE:
<223> OTHER INFORMATION: target sequence

<400> SEQUENCE: 601
aaacagcata ccaggtggac a                                              21

<210> SEQ ID NO 602
<211> LENGTH: 21
<212> TYPE: DNA
<213> ORGANISM: Artificial Sequence
<220> FEATURE:
<223> OTHER INFORMATION: target sequence

<400> SEQUENCE: 602
aacagcatac caggtggaca t                                              21

<210> SEQ ID NO 603
<211> LENGTH: 21
<212> TYPE: DNA
<213> ORGANISM: Artificial Sequence
<220> FEATURE:
<223> OTHER INFORMATION: target sequence

<400> SEQUENCE: 603
aacaacatag ggtcaagcaa c                                              21

<210> SEQ ID NO 604
<211> LENGTH: 21
<212> TYPE: DNA
<213> ORGANISM: Artificial Sequence
<220> FEATURE:
<223> OTHER INFORMATION: target sequence

<400> SEQUENCE: 604
aacatagggt caagcaaccc a                                              21

<210> SEQ ID NO 605
<211> LENGTH: 21
<212> TYPE: DNA
<213> ORGANISM: Artificial Sequence
<220> FEATURE:
<223> OTHER INFORMATION: target sequence

<400> SEQUENCE: 605
aagcaaccca gcctttctc a                                               21

<210> SEQ ID NO 606
<211> LENGTH: 21
<212> TYPE: DNA
<213> ORGANISM: Artificial Sequence
<220> FEATURE:
<223> OTHER INFORMATION: target sequence

<400> SEQUENCE: 606
aacccagcct tttctcatga a                                              21
```

```
<210> SEQ ID NO 607
<211> LENGTH: 21
<212> TYPE: DNA
<213> ORGANISM: Artificial Sequence
<220> FEATURE:
<223> OTHER INFORMATION: target sequence

<400> SEQUENCE: 607
aactggtgac cctcccagaa t                                              21

<210> SEQ ID NO 608
<211> LENGTH: 21
<212> TYPE: DNA
<213> ORGANISM: Artificial Sequence
<220> FEATURE:
<223> OTHER INFORMATION: target sequence

<400> SEQUENCE: 608
aatctcaagc accagcggac c                                              21

<210> SEQ ID NO 609
<211> LENGTH: 21
<212> TYPE: DNA
<213> ORGANISM: Artificial Sequence
<220> FEATURE:
<223> OTHER INFORMATION: target sequence

<400> SEQUENCE: 609
aagcaccagc ggacctcgga g                                              21

<210> SEQ ID NO 610
<211> LENGTH: 21
<212> TYPE: DNA
<213> ORGANISM: Artificial Sequence
<220> FEATURE:
<223> OTHER INFORMATION: target sequence

<400> SEQUENCE: 610
aagatgctgc ttatagccat c                                              21

<210> SEQ ID NO 611
<211> LENGTH: 21
<212> TYPE: DNA
<213> ORGANISM: Artificial Sequence
<220> FEATURE:
<223> OTHER INFORMATION: target sequence

<400> SEQUENCE: 611
aatgacctgc ctgactgtgc t                                              21

<210> SEQ ID NO 612
<211> LENGTH: 21
<212> TYPE: DNA
<213> ORGANISM: Artificial Sequence
<220> FEATURE:
<223> OTHER INFORMATION: target sequence

<400> SEQUENCE: 612
aattgaagag ggcaaatgtg c                                              21

<210> SEQ ID NO 613
<211> LENGTH: 21
<212> TYPE: DNA
<213> ORGANISM: Artificial Sequence
<220> FEATURE:
<223> OTHER INFORMATION: target sequence

<400> SEQUENCE: 613
```
aagagggcaa atgtgcaaag g                                              21

<210> SEQ ID NO 614
<211> LENGTH: 21
<212> TYPE: DNA
<213> ORGANISM: Artificial Sequence
<220> FEATURE:
<223> OTHER INFORMATION: target sequence

<400> SEQUENCE: 614
aaatgtgcaa aggagaatgg c                                              21

<210> SEQ ID NO 615
<211> LENGTH: 21
<212> TYPE: DNA
<213> ORGANISM: Artificial Sequence
<220> FEATURE:
<223> OTHER INFORMATION: target sequence

<400> SEQUENCE: 615
aatgtgcaaa ggagaatggc c                                              21

<210> SEQ ID NO 616
<211> LENGTH: 21
<212> TYPE: DNA
<213> ORGANISM: Artificial Sequence
<220> FEATURE:
<223> OTHER INFORMATION: target sequence

<400> SEQUENCE: 616
aaaggagaat ggcccaagcc t                                              21

<210> SEQ ID NO 617
<211> LENGTH: 21
<212> TYPE: DNA
<213> ORGANISM: Artificial Sequence
<220> FEATURE:
<223> OTHER INFORMATION: target sequence

<400> SEQUENCE: 617
aaggagaatg gcccaagcct t                                              21

<210> SEQ ID NO 618
<211> LENGTH: 21
<212> TYPE: DNA
<213> ORGANISM: Artificial Sequence
<220> FEATURE:
<223> OTHER INFORMATION: target sequence

<400> SEQUENCE: 618
aatggcccaa gccttccaaa a                                              21

<210> SEQ ID NO 619
<211> LENGTH: 21
<212> TYPE: DNA
<213> ORGANISM: Artificial Sequence
<220> FEATURE:
<223> OTHER INFORMATION: target sequence

<400> SEQUENCE: 619
aagccttcca aaacgtgagg g                                              21

<210> SEQ ID NO 620
<211> LENGTH: 21
<212> TYPE: DNA
<213> ORGANISM: Artificial Sequence

```
<220> FEATURE:
<223> OTHER INFORMATION: target sequence

<400> SEQUENCE: 620
aaaacgtgag ggaagaacca g                                              21

<210> SEQ ID NO 621
<211> LENGTH: 21
<212> TYPE: DNA
<213> ORGANISM: Artificial Sequence
<220> FEATURE:
<223> OTHER INFORMATION: target sequence

<400> SEQUENCE: 621
aaacgtgagg gaagaaccag c                                              21

<210> SEQ ID NO 622
<211> LENGTH: 21
<212> TYPE: DNA
<213> ORGANISM: Artificial Sequence
<220> FEATURE:
<223> OTHER INFORMATION: target sequence

<400> SEQUENCE: 622
aacgtgaggg aagaaccagc t                                              21

<210> SEQ ID NO 623
<211> LENGTH: 21
<212> TYPE: DNA
<213> ORGANISM: Artificial Sequence
<220> FEATURE:
<223> OTHER INFORMATION: target sequence

<400> SEQUENCE: 623
aagaaccagc tgtgcagttc a                                              21

<210> SEQ ID NO 624
<211> LENGTH: 21
<212> TYPE: DNA
<213> ORGANISM: Artificial Sequence
<220> FEATURE:
<223> OTHER INFORMATION: target sequence

<400> SEQUENCE: 624
aaccagctgt gcagttcaac t                                              21

<210> SEQ ID NO 625
<211> LENGTH: 21
<212> TYPE: DNA
<213> ORGANISM: Artificial Sequence
<220> FEATURE:
<223> OTHER INFORMATION: target sequence

<400> SEQUENCE: 625
aactcaggga ctctggccct a                                              21

<210> SEQ ID NO 626
<211> LENGTH: 21
<212> TYPE: DNA
<213> ORGANISM: Artificial Sequence
<220> FEATURE:
<223> OTHER INFORMATION: target sequence

<400> SEQUENCE: 626
aaacaggaag gtcaaaaaca a                                              21
```

```
<210> SEQ ID NO 627
<211> LENGTH: 21
<212> TYPE: DNA
<213> ORGANISM: Artificial Sequence
<220> FEATURE:
<223> OTHER INFORMATION: target sequence

<400> SEQUENCE: 627
aacaggaagg tcaaaaacaa c                                              21

<210> SEQ ID NO 628
<211> LENGTH: 21
<212> TYPE: DNA
<213> ORGANISM: Artificial Sequence
<220> FEATURE:
<223> OTHER INFORMATION: target sequence

<400> SEQUENCE: 628
aaggtcaaaa acaacccaga t                                              21

<210> SEQ ID NO 629
<211> LENGTH: 21
<212> TYPE: DNA
<213> ORGANISM: Artificial Sequence
<220> FEATURE:
<223> OTHER INFORMATION: target sequence

<400> SEQUENCE: 629
aaaaacaacc cagatcctac a                                              21

<210> SEQ ID NO 630
<211> LENGTH: 21
<212> TYPE: DNA
<213> ORGANISM: Artificial Sequence
<220> FEATURE:
<223> OTHER INFORMATION: target sequence

<400> SEQUENCE: 630
aaaacaaccc agatcctaca a                                              21

<210> SEQ ID NO 631
<211> LENGTH: 21
<212> TYPE: DNA
<213> ORGANISM: Artificial Sequence
<220> FEATURE:
<223> OTHER INFORMATION: target sequence

<400> SEQUENCE: 631
aaacaaccca gatcctacaa t                                              21

<210> SEQ ID NO 632
<211> LENGTH: 21
<212> TYPE: DNA
<213> ORGANISM: Artificial Sequence
<220> FEATURE:
<223> OTHER INFORMATION: target sequence

<400> SEQUENCE: 632
aacaacccag atcctacaat t                                              21

<210> SEQ ID NO 633
<211> LENGTH: 21
<212> TYPE: DNA
<213> ORGANISM: Artificial Sequence
<220> FEATURE:
<223> OTHER INFORMATION: target sequence

<400> SEQUENCE: 633
```
aacccagatc ctacaattta t                                              21

<210> SEQ ID NO 634
<211> LENGTH: 21
<212> TYPE: DNA
<213> ORGANISM: Artificial Sequence
<220> FEATURE:
<223> OTHER INFORMATION: target sequence

<400> SEQUENCE: 634
aatttatcca gtgcttgact g                                              21

<210> SEQ ID NO 635
<211> LENGTH: 21
<212> TYPE: DNA
<213> ORGANISM: Artificial Sequence
<220> FEATURE:
<223> OTHER INFORMATION: target sequence

<400> SEQUENCE: 635
aatgacatca aatttcaaga t                                              21

<210> SEQ ID NO 636
<211> LENGTH: 21
<212> TYPE: DNA
<213> ORGANISM: Artificial Sequence
<220> FEATURE:
<223> OTHER INFORMATION: target sequence

<400> SEQUENCE: 636
aaatttcaag atgtgattgg g                                              21

<210> SEQ ID NO 637
<211> LENGTH: 21
<212> TYPE: DNA
<213> ORGANISM: Artificial Sequence
<220> FEATURE:
<223> OTHER INFORMATION: target sequence

<400> SEQUENCE: 637
aatttcaaga tgtgattggg g                                              21

<210> SEQ ID NO 638
<211> LENGTH: 21
<212> TYPE: DNA
<213> ORGANISM: Artificial Sequence
<220> FEATURE:
<223> OTHER INFORMATION: target sequence

<400> SEQUENCE: 638
aagatgtgat tggggagggc a                                              21

<210> SEQ ID NO 639
<211> LENGTH: 21
<212> TYPE: DNA
<213> ORGANISM: Artificial Sequence
<220> FEATURE:
<223> OTHER INFORMATION: target sequence

<400> SEQUENCE: 639
aattttggcc aagttcttaa g                                              21

<210> SEQ ID NO 640
<211> LENGTH: 21
<212> TYPE: DNA
<213> ORGANISM: Artificial Sequence

```
<220> FEATURE:
<223> OTHER INFORMATION: target sequence

<400> SEQUENCE: 640
aagttcttaa ggcgcgcatc a                                              21

<210> SEQ ID NO 641
<211> LENGTH: 21
<212> TYPE: DNA
<213> ORGANISM: Artificial Sequence
<220> FEATURE:
<223> OTHER INFORMATION: target sequence

<400> SEQUENCE: 641
aaggcgcgca tcaagaagga t                                              21

<210> SEQ ID NO 642
<211> LENGTH: 21
<212> TYPE: DNA
<213> ORGANISM: Artificial Sequence
<220> FEATURE:
<223> OTHER INFORMATION: target sequence

<400> SEQUENCE: 642
aagaaggatg ggttacggat g                                              21

<210> SEQ ID NO 643
<211> LENGTH: 21
<212> TYPE: DNA
<213> ORGANISM: Artificial Sequence
<220> FEATURE:
<223> OTHER INFORMATION: target sequence

<400> SEQUENCE: 643
aaggatgggt tacggatgga t                                              21

<210> SEQ ID NO 644
<211> LENGTH: 21
<212> TYPE: DNA
<213> ORGANISM: Artificial Sequence
<220> FEATURE:
<223> OTHER INFORMATION: target sequence

<400> SEQUENCE: 644
aaaagaatga agaatatgc c                                               21

<210> SEQ ID NO 645
<211> LENGTH: 21
<212> TYPE: DNA
<213> ORGANISM: Artificial Sequence
<220> FEATURE:
<223> OTHER INFORMATION: target sequence

<400> SEQUENCE: 645
aaagaatgaa agaatatgcc t                                              21

<210> SEQ ID NO 646
<211> LENGTH: 21
<212> TYPE: DNA
<213> ORGANISM: Artificial Sequence
<220> FEATURE:
<223> OTHER INFORMATION: target sequence

<400> SEQUENCE: 646
aagaatgaaa gaatatgcct c                                              21
```

```
<210> SEQ ID NO 647
<211> LENGTH: 21
<212> TYPE: DNA
<213> ORGANISM: Artificial Sequence
<220> FEATURE:
<223> OTHER INFORMATION: target sequence

<400> SEQUENCE: 647
aatgaaagaa tatgcctcca a                                         21

<210> SEQ ID NO 648
<211> LENGTH: 21
<212> TYPE: DNA
<213> ORGANISM: Artificial Sequence
<220> FEATURE:
<223> OTHER INFORMATION: target sequence

<400> SEQUENCE: 648
aaagaatatg cctccaaaga t                                         21

<210> SEQ ID NO 649
<211> LENGTH: 21
<212> TYPE: DNA
<213> ORGANISM: Artificial Sequence
<220> FEATURE:
<223> OTHER INFORMATION: target sequence

<400> SEQUENCE: 649
aagaatatgc ctccaaagat g                                         21

<210> SEQ ID NO 650
<211> LENGTH: 21
<212> TYPE: DNA
<213> ORGANISM: Artificial Sequence
<220> FEATURE:
<223> OTHER INFORMATION: target sequence

<400> SEQUENCE: 650
aatatgcctc caaagatgat c                                         21

<210> SEQ ID NO 651
<211> LENGTH: 21
<212> TYPE: DNA
<213> ORGANISM: Artificial Sequence
<220> FEATURE:
<223> OTHER INFORMATION: target sequence

<400> SEQUENCE: 651
aaagatgatc acagggactt t                                         21

<210> SEQ ID NO 652
<211> LENGTH: 21
<212> TYPE: DNA
<213> ORGANISM: Artificial Sequence
<220> FEATURE:
<223> OTHER INFORMATION: target sequence

<400> SEQUENCE: 652
aagatgatca cagggacttt g                                         21

<210> SEQ ID NO 653
<211> LENGTH: 21
<212> TYPE: DNA
<213> ORGANISM: Artificial Sequence
<220> FEATURE:
<223> OTHER INFORMATION: target sequence

<400> SEQUENCE: 653
```

-continued aactggaagt tctttgtaaa c                                              21

<210> SEQ ID NO 654
<211> LENGTH: 21
<212> TYPE: DNA
<213> ORGANISM: Artificial Sequence
<220> FEATURE:
<223> OTHER INFORMATION: target sequence

<400> SEQUENCE: 654
aagttctttg taaacttgga c                                              21

<210> SEQ ID NO 655
<211> LENGTH: 21
<212> TYPE: DNA
<213> ORGANISM: Artificial Sequence
<220> FEATURE:
<223> OTHER INFORMATION: target sequence

<400> SEQUENCE: 655
aaacttggac accatccaaa c                                              21

<210> SEQ ID NO 656
<211> LENGTH: 21
<212> TYPE: DNA
<213> ORGANISM: Artificial Sequence
<220> FEATURE:
<223> OTHER INFORMATION: target sequence

<400> SEQUENCE: 656
aacttggaca ccatccaaac a                                              21

<210> SEQ ID NO 657
<211> LENGTH: 21
<212> TYPE: DNA
<213> ORGANISM: Artificial Sequence
<220> FEATURE:
<223> OTHER INFORMATION: target sequence

<400> SEQUENCE: 657
aaacatcatc aatctcttag g                                              21

<210> SEQ ID NO 658
<211> LENGTH: 21
<212> TYPE: DNA
<213> ORGANISM: Artificial Sequence
<220> FEATURE:
<223> OTHER INFORMATION: target sequence

<400> SEQUENCE: 658
aacatcatca atctcttagg a                                              21

<210> SEQ ID NO 659
<211> LENGTH: 21
<212> TYPE: DNA
<213> ORGANISM: Artificial Sequence
<220> FEATURE:
<223> OTHER INFORMATION: target sequence

<400> SEQUENCE: 659
aatctcttag gagcatgtga a                                              21

<210> SEQ ID NO 660
<211> LENGTH: 21
<212> TYPE: DNA
<213> ORGANISM: Artificial Sequence

```
<220> FEATURE:
<223> OTHER INFORMATION: target sequence

<400> SEQUENCE: 660
aacatcgagg ctacttgtac c                                              21

<210> SEQ ID NO 661
<211> LENGTH: 21
<212> TYPE: DNA
<213> ORGANISM: Artificial Sequence
<220> FEATURE:
<223> OTHER INFORMATION: target sequence

<400> SEQUENCE: 661
aaaccttctg gacttccttc g                                              21

<210> SEQ ID NO 662
<211> LENGTH: 21
<212> TYPE: DNA
<213> ORGANISM: Artificial Sequence
<220> FEATURE:
<223> OTHER INFORMATION: target sequence

<400> SEQUENCE: 662
aaccttctgg acttccttcg c                                              21

<210> SEQ ID NO 663
<211> LENGTH: 21
<212> TYPE: DNA
<213> ORGANISM: Artificial Sequence
<220> FEATURE:
<223> OTHER INFORMATION: target sequence

<400> SEQUENCE: 663
aagagccgtg tgctggagac g                                              21

<210> SEQ ID NO 664
<211> LENGTH: 21
<212> TYPE: DNA
<213> ORGANISM: Artificial Sequence
<220> FEATURE:
<223> OTHER INFORMATION: target sequence

<400> SEQUENCE: 664
aatagcaccg cgtccacact g                                              21

<210> SEQ ID NO 665
<211> LENGTH: 21
<212> TYPE: DNA
<213> ORGANISM: Artificial Sequence
<220> FEATURE:
<223> OTHER INFORMATION: target sequence

<400> SEQUENCE: 665
aaaaacagtt tatccacagg g                                              21

<210> SEQ ID NO 666
<211> LENGTH: 21
<212> TYPE: DNA
<213> ORGANISM: Artificial Sequence
<220> FEATURE:
<223> OTHER INFORMATION: target sequence

<400> SEQUENCE: 666
aaaacagttt atccacaggg a                                              21
```

```
<210> SEQ ID NO 667
<211> LENGTH: 21
<212> TYPE: DNA
<213> ORGANISM: Artificial Sequence
<220> FEATURE:
<223> OTHER INFORMATION: target sequence

<400> SEQUENCE: 667
aaacagttta tccacaggga t                                              21

<210> SEQ ID NO 668
<211> LENGTH: 21
<212> TYPE: DNA
<213> ORGANISM: Artificial Sequence
<220> FEATURE:
<223> OTHER INFORMATION: target sequence

<400> SEQUENCE: 668
aacagtttat ccacagggat c                                              21

<210> SEQ ID NO 669
<211> LENGTH: 21
<212> TYPE: DNA
<213> ORGANISM: Artificial Sequence
<220> FEATURE:
<223> OTHER INFORMATION: target sequence

<400> SEQUENCE: 669
aaacatttta gttggtgaaa a                                              21

<210> SEQ ID NO 670
<211> LENGTH: 21
<212> TYPE: DNA
<213> ORGANISM: Artificial Sequence
<220> FEATURE:
<223> OTHER INFORMATION: target sequence

<400> SEQUENCE: 670 aacatttag ttggtgaaaa c                                               21

<210> SEQ ID NO 671
<211> LENGTH: 21
<212> TYPE: DNA
<213> ORGANISM: Artificial Sequence
<220> FEATURE:
<223> OTHER INFORMATION: target sequence

<400> SEQUENCE: 671
aaaactatgt ggcaaaaata g                                              21

<210> SEQ ID NO 672
<211> LENGTH: 21
<212> TYPE: DNA
<213> ORGANISM: Artificial Sequence
<220> FEATURE:
<223> OTHER INFORMATION: target sequence

<400> SEQUENCE: 672
aaactatgtg gcaaaaatag c                                              21

<210> SEQ ID NO 673
<211> LENGTH: 21
<212> TYPE: DNA
<213> ORGANISM: Artificial Sequence
<220> FEATURE:
<223> OTHER INFORMATION: target sequence

<400> SEQUENCE: 673
```
aactatgtgg caaaaatagc a                                                    21

<210> SEQ ID NO 674
<211> LENGTH: 21
<212> TYPE: DNA
<213> ORGANISM: Artificial Sequence
<220> FEATURE:
<223> OTHER INFORMATION: target sequence

<400> SEQUENCE: 674
aaaaatagca gattttggat t                                                    21

<210> SEQ ID NO 675
<211> LENGTH: 21
<212> TYPE: DNA
<213> ORGANISM: Artificial Sequence
<220> FEATURE:
<223> OTHER INFORMATION: target sequence

<400> SEQUENCE: 675
aaaatagcag attttggatt g                                                    21

<210> SEQ ID NO 676
<211> LENGTH: 21
<212> TYPE: DNA
<213> ORGANISM: Artificial Sequence
<220> FEATURE:
<223> OTHER INFORMATION: target sequence

<400> SEQUENCE: 676
aaatagcaga ttttggattg t                                                    21

<210> SEQ ID NO 677
<211> LENGTH: 21
<212> TYPE: DNA
<213> ORGANISM: Artificial Sequence
<220> FEATURE:
<223> OTHER INFORMATION: target sequence

<400> SEQUENCE: 677
aatagcagat tttggattgt c                                                    21

<210> SEQ ID NO 678
<211> LENGTH: 21
<212> TYPE: DNA
<213> ORGANISM: Artificial Sequence
<220> FEATURE:
<223> OTHER INFORMATION: target sequence

<400> SEQUENCE: 678
aagaggtgta cgtgaaaaag a                                                    21

<210> SEQ ID NO 679
<211> LENGTH: 21
<212> TYPE: DNA
<213> ORGANISM: Artificial Sequence
<220> FEATURE:
<223> OTHER INFORMATION: target sequence

<400> SEQUENCE: 679
aaaaagacaa tgggaaggct c                                                    21

<210> SEQ ID NO 680
<211> LENGTH: 21
<212> TYPE: DNA
<213> ORGANISM: Artificial Sequence

```
<220> FEATURE:
<223> OTHER INFORMATION: target sequence

<400> SEQUENCE: 680
aaaagacaat gggaaggctc c                                              21

<210> SEQ ID NO 681
<211> LENGTH: 21
<212> TYPE: DNA
<213> ORGANISM: Artificial Sequence
<220> FEATURE:
<223> OTHER INFORMATION: target sequence

<400> SEQUENCE: 681
aaagacaatg ggaaggctcc c                                              21

<210> SEQ ID NO 682
<211> LENGTH: 21
<212> TYPE: DNA
<213> ORGANISM: Artificial Sequence
<220> FEATURE:
<223> OTHER INFORMATION: target sequence

<400> SEQUENCE: 682
aagacaatgg gaaggctccc a                                              21

<210> SEQ ID NO 683
<211> LENGTH: 21
<212> TYPE: DNA
<213> ORGANISM: Artificial Sequence
<220> FEATURE:
<223> OTHER INFORMATION: target sequence

<400> SEQUENCE: 683
aatgggaagg ctcccagtgc g                                              21

<210> SEQ ID NO 684
<211> LENGTH: 21
<212> TYPE: DNA
<213> ORGANISM: Artificial Sequence
<220> FEATURE:
<223> OTHER INFORMATION: target sequence

<400> SEQUENCE: 684
aaggctccca gtgcgctgga t                                              21

<210> SEQ ID NO 685
<211> LENGTH: 21
<212> TYPE: DNA
<213> ORGANISM: Artificial Sequence
<220> FEATURE:
<223> OTHER INFORMATION: target sequence

<400> SEQUENCE: 685
aattacagtg tgtacacaac c                                              21

<210> SEQ ID NO 686
<211> LENGTH: 21
<212> TYPE: DNA
<213> ORGANISM: Artificial Sequence
<220> FEATURE:
<223> OTHER INFORMATION: target sequence

<400> SEQUENCE: 686
aaccaacagt gatgtatggt c                                              21
```

```
<210> SEQ ID NO 687
<211> LENGTH: 21
<212> TYPE: DNA
<213> ORGANISM: Artificial Sequence
<220> FEATURE:
<223> OTHER INFORMATION: target sequence

<400> SEQUENCE: 687
aacagtgatg tatggtccta t                                              21

<210> SEQ ID NO 688
<211> LENGTH: 21
<212> TYPE: DNA
<213> ORGANISM: Artificial Sequence
<220> FEATURE:
<223> OTHER INFORMATION: target sequence

<400> SEQUENCE: 688
aactctacga gaagctgccc c                                              21

<210> SEQ ID NO 689
<211> LENGTH: 21
<212> TYPE: DNA
<213> ORGANISM: Artificial Sequence
<220> FEATURE:
<223> OTHER INFORMATION: target sequence

<400> SEQUENCE: 689
aagctgcccc agggctacag a                                              21

<210> SEQ ID NO 690
<211> LENGTH: 21
<212> TYPE: DNA
<213> ORGANISM: Artificial Sequence
<220> FEATURE:
<223> OTHER INFORMATION: target sequence

<400> SEQUENCE: 690
aagcccctga actgtgatga t                                              21

<210> SEQ ID NO 691
<211> LENGTH: 21
<212> TYPE: DNA
<213> ORGANISM: Artificial Sequence
<220> FEATURE:
<223> OTHER INFORMATION: target sequence

<400> SEQUENCE: 691
aactgtgatg atgaggtgta t                                              21

<210> SEQ ID NO 692
<211> LENGTH: 21
<212> TYPE: DNA
<213> ORGANISM: Artificial Sequence
<220> FEATURE:
<223> OTHER INFORMATION: target sequence

<400> SEQUENCE: 692
aatgagacaa tgctggcggg a                                              21

<210> SEQ ID NO 693
<211> LENGTH: 21
<212> TYPE: DNA
<213> ORGANISM: Artificial Sequence
<220> FEATURE:
<223> OTHER INFORMATION: target sequence

<400> SEQUENCE: 693
```
aatgctggcg ggagaagcct t     21

<210> SEQ ID NO 694
<211> LENGTH: 21
<212> TYPE: DNA
<213> ORGANISM: Artificial Sequence
<220> FEATURE:
<223> OTHER INFORMATION: target sequence

<400> SEQUENCE: 694
aagccttatg agaggccatc a     21

<210> SEQ ID NO 695
<211> LENGTH: 21
<212> TYPE: DNA
<213> ORGANISM: Artificial Sequence
<220> FEATURE:
<223> OTHER INFORMATION: target sequence

<400> SEQUENCE: 695
aaacagaatg ttagaggagc g     21

<210> SEQ ID NO 696
<211> LENGTH: 21
<212> TYPE: DNA
<213> ORGANISM: Artificial Sequence
<220> FEATURE:
<223> OTHER INFORMATION: target sequence

<400> SEQUENCE: 696
aacagaatgt tagaggagcg a     21

<210> SEQ ID NO 697
<211> LENGTH: 21
<212> TYPE: DNA
<213> ORGANISM: Artificial Sequence
<220> FEATURE:
<223> OTHER INFORMATION: target sequence

<400> SEQUENCE: 697
aatgttagag gagcgaaaga c     21

<210> SEQ ID NO 698
<211> LENGTH: 21
<212> TYPE: DNA
<213> ORGANISM: Artificial Sequence
<220> FEATURE:
<223> OTHER INFORMATION: target sequence

<400> SEQUENCE: 698
aaagacctac gtgaatacca c     21

<210> SEQ ID NO 699
<211> LENGTH: 21
<212> TYPE: DNA
<213> ORGANISM: Artificial Sequence
<220> FEATURE:
<223> OTHER INFORMATION: target sequence

<400> SEQUENCE: 699
aagacctacg tgaataccac g     21

<210> SEQ ID NO 700
<211> LENGTH: 21
<212> TYPE: DNA
<213> ORGANISM: Artificial Sequence

```
<220> FEATURE:
<223> OTHER INFORMATION: target sequence

<400> SEQUENCE: 700
aataccacgc tttatgagaa g                                              21

<210> SEQ ID NO 701
<211> LENGTH: 21
<212> TYPE: DNA
<213> ORGANISM: Artificial Sequence
<220> FEATURE:
<223> OTHER INFORMATION: target sequence

<400> SEQUENCE: 701
aagtttactt atgcaggaat t                                              21

<210> SEQ ID NO 702
<211> LENGTH: 21
<212> TYPE: DNA
<213> ORGANISM: Artificial Sequence
<220> FEATURE:
<223> OTHER INFORMATION: target sequence

<400> SEQUENCE: 702
aattgactgt tctgctgaag a                                              21

<210> SEQ ID NO 703
<211> LENGTH: 21
<212> TYPE: DNA
<213> ORGANISM: Artificial Sequence
<220> FEATURE:
<223> OTHER INFORMATION: target sequence

<400> SEQUENCE: 703
ttgtatctga tgctgaaaca t                                              21

<210> SEQ ID NO 704
<211> LENGTH: 21
<212> TYPE: DNA
<213> ORGANISM: Artificial Sequence
<220> FEATURE:
<223> OTHER INFORMATION: target sequence

<400> SEQUENCE: 704
tactcaagat gtgaccagag a                                              21

<210> SEQ ID NO 705
<211> LENGTH: 21
<212> TYPE: DNA
<213> ORGANISM: Artificial Sequence
<220> FEATURE:
<223> OTHER INFORMATION: target sequence

<400> SEQUENCE: 705
tgtgaagggc gagttcgagg a                                              21

<210> SEQ ID NO 706
<211> LENGTH: 21
<212> TYPE: DNA
<213> ORGANISM: Artificial Sequence
<220> FEATURE:
<223> OTHER INFORMATION: target sequence

<400> SEQUENCE: 706
tcaaaaaggt attgattaaa g                                              21
```

```
<210> SEQ ID NO 707
<211> LENGTH: 21
<212> TYPE: DNA
<213> ORGANISM: Artificial Sequence
<220> FEATURE:
<223> OTHER INFORMATION: target sequence

<400> SEQUENCE: 707
acctgatatt ctagaagtac a                                              21

<210> SEQ ID NO 708
<211> LENGTH: 21
<212> TYPE: DNA
<213> ORGANISM: Artificial Sequence
<220> FEATURE:
<223> OTHER INFORMATION: target sequence

<400> SEQUENCE: 708
aggctgatag tccggagatg t                                              21

<210> SEQ ID NO 709
<211> LENGTH: 21
<212> TYPE: DNA
<213> ORGANISM: Artificial Sequence
<220> FEATURE:
<223> OTHER INFORMATION: target sequence

<400> SEQUENCE: 709
actggagaat gcatttgccc t                                              21

<210> SEQ ID NO 710
<211> LENGTH: 21
<212> TYPE: DNA
<213> ORGANISM: Artificial Sequence
<220> FEATURE:
<223> OTHER INFORMATION: target sequence

<400> SEQUENCE: 710
atgtgttctg tctccctgac c                                              21

<210> SEQ ID NO 711
<211> LENGTH: 21
<212> TYPE: DNA
<213> ORGANISM: Artificial Sequence
<220> FEATURE:
<223> OTHER INFORMATION: target sequence

<400> SEQUENCE: 711
cgggccagat tgtaagctta g                                              21

<210> SEQ ID NO 712
<211> LENGTH: 21
<212> TYPE: DNA
<213> ORGANISM: Artificial Sequence
<220> FEATURE:
<223> OTHER INFORMATION: target sequence

<400> SEQUENCE: 712
ctccagtgtg agagagaagg c                                              21

<210> SEQ ID NO 713
<211> LENGTH: 21
<212> TYPE: DNA
<213> ORGANISM: Artificial Sequence
<220> FEATURE:
<223> OTHER INFORMATION: target sequence

<400> SEQUENCE: 713
```

```
catttgcaaa gcttctggct g                                              21

<210> SEQ ID NO 714
<211> LENGTH: 21
<212> TYPE: DNA
<213> ORGANISM: Artificial Sequence
<220> FEATURE:
<223> OTHER INFORMATION: target sequence

<400> SEQUENCE: 714
ccatccaccg gatcctcccc c                                              21

<210> SEQ ID NO 715
<211> LENGTH: 21
<212> TYPE: DNA
<213> ORGANISM: Artificial Sequence
<220> FEATURE:
<223> OTHER INFORMATION: target sequence

<400> SEQUENCE: 715
gttaaagttc ttccaaagcc c                                              21

<210> SEQ ID NO 716
<211> LENGTH: 21
<212> TYPE: DNA
<213> ORGANISM: Artificial Sequence
<220> FEATURE:
<223> OTHER INFORMATION: target sequence

<400> SEQUENCE: 716
ggatggacca atcaaatcca a                                              21

<210> SEQ ID NO 717
<211> LENGTH: 21
<212> TYPE: DNA
<213> ORGANISM: Artificial Sequence
<220> FEATURE:
<223> OTHER INFORMATION: target sequence

<400> SEQUENCE: 717
gaacctcgga cagaatatga a                                              21

<210> SEQ ID NO 718
<211> LENGTH: 21
<212> TYPE: DNA
<213> ORGANISM: Artificial Sequence
<220> FEATURE:
<223> OTHER INFORMATION: target sequence

<400> SEQUENCE: 718
gcttctatcg gactccctcc t                                              21

<210> SEQ ID NO 719
<211> LENGTH: 17
<212> TYPE: DNA
<213> ORGANISM: Artificial Sequence
<220> FEATURE:
<223> OTHER INFORMATION: target sequence

<400> SEQUENCE: 719
aagatgactt ttatgtt                                                   17

<210> SEQ ID NO 720
<211> LENGTH: 17
<212> TYPE: DNA
<213> ORGANISM: Artificial Sequence
```

```
<220> FEATURE:
<223> OTHER INFORMATION: target sequence

<400> SEQUENCE: 720
agaatattaa agttcca                                                      17

<210> SEQ ID NO 721
<211> LENGTH: 18
<212> TYPE: DNA
<213> ORGANISM: Artificial Sequence
<220> FEATURE:
<223> OTHER INFORMATION: target sequence

<400> SEQUENCE: 721 caggggaat ggagtgaa                                                      18

<210> SEQ ID NO 722
<211> LENGTH: 18
<212> TYPE: DNA
<213> ORGANISM: Artificial Sequence
<220> FEATURE:
<223> OTHER INFORMATION: target sequence

<400> SEQUENCE: 722
atattggatg gctattct                                                     18

<210> SEQ ID NO 723
<211> LENGTH: 19
<212> TYPE: DNA
<213> ORGANISM: Artificial Sequence
<220> FEATURE:
<223> OTHER INFORMATION: target sequence

<400> SEQUENCE: 723
actatccgtt acaaggttc                                                    19

<210> SEQ ID NO 724
<211> LENGTH: 19
<212> TYPE: DNA
<213> ORGANISM: Artificial Sequence
<220> FEATURE:
<223> OTHER INFORMATION: target sequence

<400> SEQUENCE: 724
gtatcagctc aagggccta                                                    19

<210> SEQ ID NO 725
<211> LENGTH: 20
<212> TYPE: DNA
<213> ORGANISM: Artificial Sequence
<220> FEATURE:
<223> OTHER INFORMATION: target sequence

<400> SEQUENCE: 725
gcaacccagc cttttctcat                                                   20

<210> SEQ ID NO 726
<211> LENGTH: 20
<212> TYPE: DNA
<213> ORGANISM: Artificial Sequence
<220> FEATURE:
<223> OTHER INFORMATION: target sequence

<400> SEQUENCE: 726
tgacctgcct gactgtgctg                                                   20
```

```
<210> SEQ ID NO 727
<211> LENGTH: 22
<212> TYPE: DNA
<213> ORGANISM: Artificial Sequence
<220> FEATURE:
<223> OTHER INFORMATION: target sequence

<400> SEQUENCE: 727
aaccagctgt gcagttcaac tc                                              22

<210> SEQ ID NO 728
<211> LENGTH: 22
<212> TYPE: DNA
<213> ORGANISM: Artificial Sequence
<220> FEATURE:
<223> OTHER INFORMATION: target sequence

<400> SEQUENCE: 728
actggaatga catcaaattt ca                                              22

<210> SEQ ID NO 729
<211> LENGTH: 23
<212> TYPE: DNA
<213> ORGANISM: Artificial Sequence
<220> FEATURE:
<223> OTHER INFORMATION: target sequence

<400> SEQUENCE: 729
aatgaaagaa tatgcctcca aag                                             23

<210> SEQ ID NO 730
<211> LENGTH: 23
<212> TYPE: DNA
<213> ORGANISM: Artificial Sequence
<220> FEATURE:
<223> OTHER INFORMATION: target sequence

<400> SEQUENCE: 730
ctcttaggag catgtgaaca tcg                                             23

<210> SEQ ID NO 731
<211> LENGTH: 24
<212> TYPE: DNA
<213> ORGANISM: Artificial Sequence
<220> FEATURE:
<223> OTHER INFORMATION: target sequence

<400> SEQUENCE: 731
acggacccag catttgccat tgcc                                            24

<210> SEQ ID NO 732
<211> LENGTH: 24
<212> TYPE: DNA
<213> ORGANISM: Artificial Sequence
<220> FEATURE:
<223> OTHER INFORMATION: target sequence

<400> SEQUENCE: 732
tgaaaactat gtggcaaaaa tagc                                            24

<210> SEQ ID NO 733
<211> LENGTH: 25
<212> TYPE: DNA
<213> ORGANISM: Artificial Sequence
<220> FEATURE:
<223> OTHER INFORMATION: target sequence

<400> SEQUENCE: 733
```

```
ctggatggcc atcgagtcac tgaat                                            25

<210> SEQ ID NO 734
<211> LENGTH: 25
<212> TYPE: DNA
<213> ORGANISM: Artificial Sequence
<220> FEATURE:
<223> OTHER INFORMATION: target sequence

<400> SEQUENCE: 734
agactggaga agccccctgaa ctgtg                                           25

<210> SEQ ID NO 735
<211> LENGTH: 26
<212> TYPE: DNA
<213> ORGANISM: Artificial Sequence
<220> FEATURE:
<223> OTHER INFORMATION: target sequence

<400> SEQUENCE: 735
ttgcccagat attggtgtcc ttaaac                                           26

<210> SEQ ID NO 736
<211> LENGTH: 26
<212> TYPE: DNA
<213> ORGANISM: Artificial Sequence
<220> FEATURE:
<223> OTHER INFORMATION: target sequence

<400> SEQUENCE: 736
atgagaagtt tacttatgca ggaatt                                           26
```

COMPOSITIONS AND METHODS FOR SIRNA INHIBITION OF ANGIOPOIETIN 1 AND 2 AND THEIR RECEPTOR TIE2

CROSS REFERENCE TO RELATED APPLICATION

This application claims the benefit of U.S. provisional patent application Ser. No. 60/463,981, filed on Apr. 18, 2003.

FIELD OF THE INVENTION

This invention relates to the regulation of angiopoietin 1, angiopoietin 2 and Tie2 gene expression by small interfering RNA, in particular for treating diseases or conditions involving angiogenesis.

BACKGROUND OF THE INVENTION

Angiogenesis or "neovascularization" is the formation of new blood vessels from the endothelial cells (EC) of preexisting blood vessels. This process involves EC migration, proliferation, and differentiation, which begins with localized breakdown of the basement membrane in the parent vessel. The EC then migrate away from the parent vessel into the interstitial extracellular matrix (ECM) to form a capillary sprout, which elongates due to continued migration and proliferation of the cells.

Angiogenesis is typically held under strict control, and under normal conditions occurs only under certain defined physiological processes. For example, angiogenesis occurs during embryogenesis, post-natal growth, wound repair, and menstruation. Uncontrolled angiogenesis, however, can result in pathogenic conditions where the developing blood vessels destroy the surrounding tissue or sustain malignancies. Such pathogenic conditions include diabetic retinopathy, psoriasis, exudative or "wet" age-related macular degeneration ("AMD"), inflammatory disorders, and most cancers. AMD in particular is a clinically important angiogenic disease. This condition is characterized by choroidal neovascularization in one or both eyes in aging individuals, and is the major cause of blindness in industrialized countries.

Two key regulators of angiogenesis are angiopoietin-1 ("Ang1") and angiopoietin-2 ("Ang2"). These regulators can act in concert with vascular endothelial growth factor ("VEGF") to regulate angiogenesis, although inhibition of Ang1 or Ang2 alone appears to block neovascularization. Ang1, Ang2 and VEGF exert their effect on EC through the two VEGF receptors and another tyrosine kinase receptor called "tyrosine kinase with immunoglobulin and epidermal growth factor homology domains 2" or "Tie2." Hackett et al. (2002), *J. Cell. Phys.* 192: 182-187. Whereas VEGF binding to its receptors is crucial for initiating the angiogenic process, Ang1 and Ang2 bind to Tie2 and modulate maturation of the new blood vessels. Ang1 and Ang2 are also involved in maintaining endothelial cell integrity. Lobov et al. (2002), *Proc. Nat. Acad. Sci. USA* 99: 11205-11210. As discussed below, agents which bind to and block the Tie2 receptor can also inhibit angiogenesis.

Ang1 and Ang2 are differentially expressed, and early studies indicated that Ang1 promoted neovascularization and Ang2 was an angiogenesis antagonist. However, evidence now shows that Ang2 can increase blood vessel diameter and promote remodeling of the basal lamina. Ang2 also appears to induce EC proliferation, migration and sprouting of blood vessels in the presence of VEGF. Lobov et al., 2002, supra.

Ang1 reportedly promotes angiogenesis during embryonic development, in particular through the modulation of endothelial-stromal cell communication and by regulating the maturation and stability of blood vessels. Lin P et al., *Proc. Nat. Acad. Sci. USA* 95: 8829-8834 (1998). However, the widespread expression of Ang1 and Tie2 in vascular endothelium, and phosphorylation of Tie2 in quiescent adult vasculature also suggest that Ang1 is involved in postnatal angiogenesis. Takagi et al. (2003), *Inv. Ophthalm. Vis. Sci.* 44: 393-402.

In contrast to the more extensive expression patterns of Ang1 and Tie2, Ang2 appears to be expressed only at sites of vascular remodeling. Takagi et al. (2003), supra. For example, Ang2 expression is markedly increased in ovary, uterus and placenta during menstruation. Ang2 expression levels also follow a cyclical pattern of expression in the corpus luteum, which parallels the cycle of quiescence, angiogenesis and vascular regression of this structure (i.e., Ang2 levels are low during quiescence and high during angiogenesis and regression). Hackett et al., 2002, supra. Ang2 is also induced by hypoxic cytokines, including VEGF, and is expressed in tissues undergoing pathologic angiogenesis associated with tumors, AMD and in an animal model of retinal ischemia. Takagi et al., 2003, supra. Moreover, Ang2 is upregulated in the epiretinal membranes of patients with ischemic retinal disorders, but not in membranes from patients with non-ischemic retinal disorders. The expression of Ang1, however, remains similar in epiretinal membranes from patients with ischemic or non-ischemic disorders. Takagi et al., 2003, supra.

Ang2 and Tie2 are co-localized in the EC of highly vascularized regions, and Tie2 is overexpressed in areas of vascular remodeling. Asahara T. et al., *Circ. Res.* 83: 223-240 report that Ang1 and Ang2 have similar synergistic effects with VEGF to promote angiogenesis in a mouse corneal neovascularization assay. Thus, Ang1, Ang2 and Tie2 play an important role in both normal and pathogenic neovascularization in developing and adult organisms.

Ang1, Ang2 or Tie2 are therefore attractive therapeutic targets for treatment of pathogenic angiogenesis. For example, Lin P et al. (1998), supra, inhibited tumor growth and metastasis in a mouse model by expressing a soluble recombinant Tie2 receptor. The recombinant Tie2 protein blocked ligand binding to endogenous Tie2 receptors, but likely produced only a stoichiometric reduction in Ang2/Tie2 binding. Takagi et al., 2003, supra inhibited of Tie2 signaling with a soluble fusion protein containing the ectoplasmic domain of Tie2, which suppressed hypoxia-induced retinal angiogenesis both in vitro and in vivo. Asahara et al. (1998), supra showed that administration of a soluble Tie2 receptor abolished the effects of Ang1 or Ang2 on VEGF-induced neovascularization in the mouse cornea. However, therapeutic strategies based on agents such as soluble Tie2 receptors are not preferred, however, because such agents would likely be overwhelmed by the high production of Ang2 or Tie2 in the EC of highly vascularized areas.

RNA interference (hereinafter "RNAi") is a method of post-transcriptional gene regulation that is conserved throughout many eukaryotic organisms. RNAi is induced by short (i.e., <30 nucleotide) double stranded RNA ("dsRNA") molecules which are present in the cell (Fire A et al. (1998), *Nature* 391: 806-811). These short dsRNA molecules, called "short interfering RNA" or "siRNA," cause the destruction of messenger RNAs ("mRNAs") which share sequence homology with the siRNA to within one nucleotide resolution (Elbashir S M et al. (2001), *Genes Dev,* 15: 188-200). It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

Elbashir S M et al. (2001), supra, has shown that synthetic siRNA of 21 and 22 nucleotides in length, and which have short 3' overhangs, are able to induce RNAi of target mRNA in a Drosophila cell lysate. Cultured mammalian cells also exhibit RNAi degradation with synthetic siRNA (Elbashir S M et al. (2001) Nature, 411: 494-498), and RNAi degradation induced by synthetic siRNA has recently been shown in living mice (McCaffrey A P et al. (2002), Nature, 418: 38-39; Xia H et al. (2002), Nat. Biotech. 20: 1006-1010). The therapeutic potential of siRNA-induced RNAi degradation has been demonstrated in several recent in vitro studies, including the siRNA-directed inhibition of HIV-1 infection (Novina C D et al. (2002), Nat. Med. 8: 681-686) and reduction of neurotoxic polyglutamine disease protein expression (Xia H et al. (2002), supra).

What is needed, therefore, are agents and methods which selectively inhibit expression of Ang1, Ang2 or Tie2 in catalytic or sub-stoichiometric amounts, in order to effectively decrease or block angiogenesis.

SUMMARY OF THE INVENTION

The present invention is directed to siRNA which specifically target and cause RNAi-induced degradation of mRNA from Ang1, Ang2 or Tie2 genes. These siRNA degrade Ang1, Ang2 or Tie2 mRNA in substoichiometric amounts. The siRNA compounds and compositions of the invention are thus used to inhibit angiogenesis. In particular, the siRNA of the invention are useful for treating cancerous tumors and disorders related to ocular neovascularization, such as age-related macular degeneration and diabetic retinopathy.

Thus, the invention provides an isolated siRNA which targets human Ang1, Ang2 or Tie2 mRNA, or an alternative splice form, mutant or cognate thereof. The siRNA comprises a sense RNA strand and an antisense RNA strand which form an RNA duplex. The sense RNA strand comprises a nucleotide sequence substantially identical to a target sequence of about 19 to about 25 contiguous nucleotides in the target mRNA.

The invention also provides recombinant plasmids and viral vectors which express the siRNA of the invention, as well as pharmaceutical compositions comprising the siRNA of the invention and a pharmaceutically acceptable carrier.

The invention further provides a method of inhibiting expression of human Ang1, Ang2 or Tie2 mRNA, or an alternative splice form, mutant or cognate thereof, comprising administering to a subject an effective amount of the siRNA of the invention such that the target mRNA is degraded.

The invention further provides a method of inhibiting angiogenesis in a subject, comprising administering to a subject an effective amount of an siRNA targeted to human Ang1, Ang2 or Tie2 mRNA, or an alternative splice form, mutant or cognate thereof.

The invention further provides a method of treating an angiogenic disease, comprising administering to a subject in need of such treatment an effective amount of an siRNA targeted to human Ang1, Ang2 or Tie2 mRNA, or an alternative splice form, mutant or cognate thereof, such that angiogenesis associated with the angiogenic disease is inhibited.

DETAILED DESCRIPTION OF THE INVENTION

Figure 1:
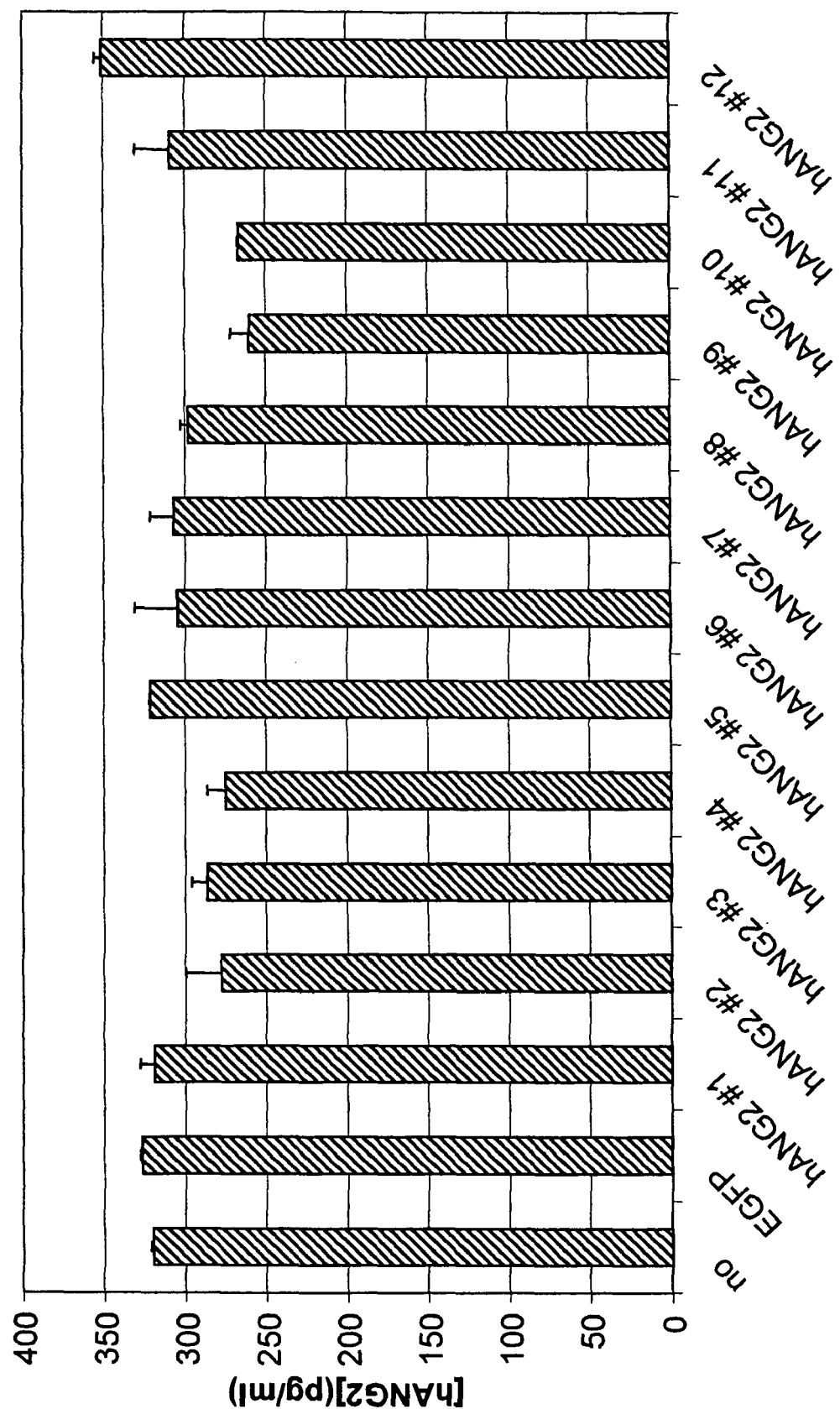
FIG. 1 is a histogram showing the silencing effect of siRNA candidates, as measured by the levels of human angiopoietin 2 ("hANG2") protein in growth medium removed from tissue culture wells containing HEK-293 cells transfected with: twelve different siRNA targeted to hANG2 mRNA (hANG2#1-hANG2#12); with control nonspecific siRNA targeted to enhanced green fluorescent protein ("EGFP"); or with transfection reagent containing no siRNA ("no"). hANG2 protein level is given in picograms of protein per milliliter of growth medium (pg/ml), as measured by hANG2 ELISA at 48 hours post-transfection.

Unless otherwise indicated, all nucleic acid sequences herein are given in the 5' to 3' direction. Also, all deoxyribonucleotides in a nucleic acid sequence are represented by capital letters (e.g., deoxythymidine is "T"), and ribonucleotides in a nucleic acid sequence are represented by lower case letters (e.g., uridine is "u").

Compositions and methods comprising siRNA targeted to Ang1, Ang2 and Tie2 mRNA are advantageously used to inhibit angiogenesis, in particular for the treatment of angiogenic disease. The siRNA of the invention are believed to cause the RNAi-mediated degradation of these mRNAs, so that the protein products of the Ang1, Ang2 or Tie2 genes are not produced or are produced in reduced amounts. Because Ang1, Ang2 and Tie2 are involved in angiogenesis, the siRNA-mediated degradation of Ang1, Ang2 or Tie2 mRNA inhibits the angiogenic process.

As used herein, siRNA which is "targeted to the Ang1, Ang2 or Tie2 mRNA" means siRNA in which a first strand of the duplex is substantially identical to the nucleotide sequence of a portion of the Ang1, Ang2 or Tie2 mRNA sequence. It is understood that the second strand of the siRNA duplex is complementary to both the first strand of the siRNA duplex and to the same portion of the Ang1, Ang2 or Tie2 mRNA.

The invention therefore provides isolated siRNA comprising short double-stranded RNA from about 17 nucleotides to about 29 nucleotides in length, preferably from about 19 to about 25 nucleotides in length, that are targeted to the target mRNA. The siRNA's comprise a sense RNA strand and a complementary antisense RNA strand annealed together by standard Watson-Crick base-pairing interactions (hereinafter "base-paired"). As is described in more detail below, the sense strand comprises a nucleic acid sequence which is substantially identical to a target sequence contained within the target mRNA.

As used herein, a nucleic acid sequence "substantially identical" to a target sequence contained within the target mRNA is a nucleic acid sequence which is identical to the target sequence, or which differs from the target sequence by one or more nucleotides. Sense strands of the invention which comprise nucleic acid sequences substantially identical to a target sequence are characterized in that siRNA comprising such sense strands induce RNAi-mediated degradation of mRNA containing the target sequence. For example, an siRNA of the invention can comprise a sense strand comprise nucleic acid sequences which differ from a target sequence by one, two or three or more nucleotides, as long as RNAi-mediated degradation of the target mRNA is induced by the siRNA.

The sense and antisense strands of the present siRNA can comprise two complementary, single-stranded RNA molecules or can comprise a single molecule in which two complementary portions are base-paired and are covalently linked by a single-stranded "hairpin" area. Without wishing to be bound by any theory, it is believed that the hairpin area of the latter type of siRNA molecule is cleaved intracellularly by the "Dicer" protein (or its equivalent) to form a siRNA of two individual base-paired RNA molecules (see Tuschl, T. (2002), supra). As described below, the siRNA can also contain alterations, substitutions or modifications of one or more ribonucleotide bases. For example, the present siRNA can be altered, substituted or modified to contain one or more deoxyribonucleotide bases.

As used herein, "isolated" means synthetic, or altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered. By way of example, siRNA which are produced inside a cell by natural processes, but which are produced from an "isolated" precursor molecule, are themselves "isolated" molecules. Thus, an isolated dsRNA can be introduced into a target cell, where it is processed by the Dicer protein (or its equivalent) into isolated siRNA.

As used herein, "target mRNA" means human Ang1, Ang2 or Tie2 mRNA, mutant or alternative splice forms of human Ang1, Ang2 or Tie2 mRNA, or mRNA from cognate Ang1, Ang2 or Tie2 genes. The human Ang1, Ang2 and Tie2 mRNA sequences are described in GenBank Record Accession Nos. AY124380, NM_00147 and L06139, respectively, as the cDNA equivalents. The human Ang1, Ang2 and Tie2 mRNA sequences are given herein as SEQ ID NO: 1, SEQ ID NO: 2 and SEQ ID NO: 3, respectively, as the cDNA equivalents. One skilled in the art would understand that the cDNA sequence is equivalent to the mRNA sequence, and can be used for the same purpose herein; i.e., the generation of siRNA for inhibiting expression of Ang1, Ang2, or Tie2.

As used herein, a gene or mRNA which is "cognate" to human Ang1, Ang2 or Tie2 is a gene or mRNA from another mammalian species which is homologous to human Ang1, Ang2 or Tie2. For example, the partial sequence of Ang1 mRNA for the domesticated dog (*Canis familiaris*) is described as the cDNA equivalent in GenBank Record Accession No. AF345932, which is given herein as SEQ ID NO: 4. The *Mus musculus* (mouse) Ang2 mRNA is described as the cDNA equivalent in GenBank Record Accession No. NM_007426, which is given herein as SEQ ID NO. 5. The *Mus musculus* (mouse) and *Rattus norvegicus* (rat) Tie2 mRNA sequences are described as the cDNA equivalents in GenBank Record Accession Nos. NM_013690 and NW_043856, respectively. The mouse and rat Tie2 mRNA sequences are given herein as SEQ ID NO. 6 and SEQ ID NO. 7, respectively.

Alternative splice forms of human Ang1, Ang2 and Tie2 are also known. See, e.g., GenBank Record Accession No. AY121504, which describes a splice variant of human Ang1 as the cDNA equivalent (SEQ ID NO: 8). Kim I et al., *J. Biol. Chem.* 275 (24), 18550-18556 (2000) and GenBank Record Accession No. AF187858 describe an Ang2 splice variant encoding an Ang2 protein lacking amino acids 96-148, given as the cDNA equivalent (SEQ ID NO: 9). See also GenBank Record Accession No. AB086825, which describes a splice variant of Tie2 encoding a Tie2 protein lacking the epidermal growth factor-like domain, given as the cDNA equivalent (SEQ ID NO: 10).

The mRNA transcribed from the human Ang1, Ang2 or Tie2 genes can also be analyzed for alternative splice forms using techniques well-known in the art. Such techniques include reverse transcription-polymerase chain reaction (RT-PCR), northern blotting and in-situ hybridization. Techniques for analyzing mRNA sequences are described, for example, in Busting S A (2000), *J. Mol. Endocrinol.* 25: 169-193, the entire disclosure of which is herein incorporated by reference. Representative techniques for identifying alternatively spliced mRNAs are also described below.

For example, databases that contain nucleotide sequences related to a given disease gene can be used to identify alternatively spliced mRNA. Such databases include GenBank, Embase, and the Cancer Genome Anatomy Project (CGAP) database. The CGAP database, for example, contains expressed sequence tags (ESTs) from various types of human cancers. An mRNA or gene sequence from the Ang1, Ang2 or Tie2 genes can be used to query such a database to determine whether ESTs representing alternatively spliced mRNAs have been found.

A technique called "RNAse protection" can also be used to identify alternatively spliced Ang1, Ang2 or Tie2 mRNAs. RNAse protection involves translation of a gene sequence into synthetic RNA, which is hybridized to RNA derived from other cells; for example, cells which are induced to express Ang1, Ang2 or Tie2. The hybridized RNA is then incubated with enzymes that recognize RNA:RNA hybrid mismatches. Smaller than expected fragments indicate the presence of alternatively spliced mRNAs. The putative alternatively spliced mRNAs can be cloned and sequenced by methods well known to those skilled in the art.

RT-PCR can also be used to identify alternatively spliced Ang1, Ang2 or Tie2 mRNAs. In RT-PCR, mRNA from vascular endothelial cells or cells from other tissue known to express Ang1, Ang2 or Tie2 is converted into cDNA by the enzyme reverse transcriptase, using methods within the skill in the art. The entire coding sequence of the cDNA is then amplified via PCR using a forward primer located in the 3' untranslated region, and a reverse primer located in the 5' untranslated region. The amplified products can be analyzed for alternative splice forms, for example by comparing the size of the amplified products with the size of the expected product from normally spliced mRNA, e.g., by agarose gel electrophoresis. Any change in the size of the amplified product can indicate alternative splicing.

The mRNA produced from mutant Ang1, Ang2 or Tie2 genes can also be readily identified with the techniques described above for identifying Ang1, Ang2 or Tie2 alternative splice forms. As used herein, "mutant" Ang1, Ang2 or Tie2 genes or mRNA include human Ang1, Ang2 or Tie2 genes or mRNA which differ in sequence from the Ang1, Ang2 and Tie2 sequences set forth herein. Thus, allelic forms of the Ang1, Ang2 or Tie2 genes, and the mRNA produced from them, are considered "mutants" for purposes of this invention. See also WO 02/20734, which describes several mutants of Tie2, one of which is described in GenBank Record Accession No. AX398356, which is given herein as the cDNA equivalent in SEQ ID NO: 11.

It is understood that human Ang1, Ang2 or Tie2 mRNA may contain target sequences in common with its respective alternative splice forms, cognates or mutants. A single siRNA comprising such a common targeting sequence can therefore induce RNAi-mediated degradation of those different mRNAs which contain the common targeting sequence.

The siRNA of the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA; modifications that make the siRNA resistant to nuclease digestion (e.g., the use of 2'-substituted ribonucleotides or modifications to the sugar-phosphate backbone); or the substitution of one or more nucleotides in the siRNA with deoxyribonucleotides. siRNA which are exposed to serum, lachrymal fluid or other nuclease-rich environments, or which are delivered topically (e.g., by eyedropper), are preferably altered to increase their resistance to nuclease degradation. For example, siRNA which are administered intravascularly or topically to the eye can comprise one or more phosphorothioate linkages.

One or both strands of the siRNA of the invention can also comprise a 3' overhang. As used herein, a "3' overhang" refers to at least one unpaired nucleotide extending from the 3'-end of an RNA strand.

Thus in one embodiment, the siRNA of the invention comprises at least one 3' overhang of from 1 to about 6 nucleotides (which includes ribonucleotides or deoxynucleotides) in length, preferably from 1 to about 5 nucleotides in length, more preferably from 1 to about 4 nucleotides in length, and particularly preferably from about 2 to about 4 nucleotides in length.

In the embodiment in which both strands of the siRNA molecule comprise a 3' overhang, the length of the overhangs can be the same or different for each strand. In a most preferred embodiment, the 3' overhang is present on both strands of the siRNA, and is 2 nucleotides in length. For example, each strand of the siRNA of the invention can comprise 3' overhangs of dithymidylic acid ("TT") or diuridylic acid ("uu").

In order to enhance the stability of the present siRNA, the 3' overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2'-hydroxyl in the 2'-deoxythymidine significantly enhances the nuclease resistance of the 3' overhang in tissue culture medium.

In certain embodiments, the siRNA of the invention comprises the sequence AA(N19)TT or NA(N21), where N is any nucleotide. These siRNA comprise approximately 30-70% GC, and preferably comprise approximately 50% G/C. The sequence of the sense siRNA strand corresponds to (N19)TT or N21 (i.e., positions 3 to 23), respectively. In the latter case, the 3' end of the sense siRNA is converted to TT. The rationale for this sequence conversion is to generate a symmetric duplex with respect to the sequence composition of the sense and antisense strand 3' overhangs. The antisense RNA strand is then synthesized as the complement to positions 1 to 21 of the sense strand.

Because position 1 of the 23-nucleotide sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nucleotide sense strand in either embodiment) is generally complementary to the targeted sequence.

In another embodiment, the siRNA of the invention comprises the sequence NAR(N17)YNN, where R is a purine (e.g., A or G) and Y is a pyrimidine (e.g., C or u/T). The respective 21-nucleotide sense and antisense RNA strands of this embodiment therefore generally begin with a purine nucleotide. Such siRNA can be expressed from pol III expression vectors without a change in targeting site, as expression of RNAs from pol III promoters is only believed to be efficient when the first transcribed nucleotide is a purine.

The siRNA of the invention can be targeted to any stretch of approximately 19-25 contiguous nucleotides in any of the target mRNA sequences (the "target sequence"). Techniques for selecting target sequences for siRNA's are given, for example, in Tuschl T et al., "The siRNA User Guide," revised Oct. 11, 2002, the entire disclosure of which is herein incorporated by reference. "The siRNA User Guide" is available on the world wide web at a website maintained by Dr. Thomas Tuschl, Department of Cellular Biochemistry, AG 105, Max-Planck-Institute for Biophysical Chemistry, 37077 Göttingen, Germany, and can be found by accessing the website of the Max Planck Institute and searching with the keyword "siRNA." Thus, the sense strand of the present siRNA comprises a nucleotide sequence substantially identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3' direction) from the start codon. The target sequence can, however, be located in the 5' or 3' untranslated regions, or in the region nearby the start codon. For example, a suitable target sequence in the human Ang2 cDNA sequence is:

AATGCTGTGCAGAGGGACGCG (SEQ ID NO: 12)

Thus, an siRNA of the invention targeting SEQ ID NO: 12, and which has 3' uu overhangs on each strand (overhangs shown in bold), is:

5'-tgctgtgcagagggacgcguu-3' (SEQ ID NO: 13)
3'-uuucgacacgucucccugcgc-5' (SEQ ID NO: 14)

An siRNA of the invention targeting SEQ ID NO: 12, but having 3' TT overhangs on each strand (overhangs shown in bold) is:

5'-tgctgtgcagagggacgcgTT-3' (SEQ ID NO: 15)
3'-TTucgacacgucucccugcgc-5' (SEQ ID NO: 16)

Another target sequence from the human Ang2 cDNA sequence is:

AAGTATTAAATCAGACCACGA (SEQ ID NO: 17)

Thus, an siRNA of the invention targeting SEQ ID NO: 17, and which has 3' uu overhangs on each strand (overhangs shown in bold), is:

5'-gtattaaatcagaccacgauu-3' (SEQ ID NO: 18)
3'-uucauaauuuagucuggugcu-5' (SEQ ID NO: 19)

An siRNA of the invention targeting SEQ ID NO: 17, but having 3' TT overhangs on each strand (overhangs shown in bold) is:

5'-gtattaaatcagaccacgaTT-3' (SEQ ID NO: 20)
3'-TTcauaauuuagucuggugcu-5' (SEQ ID NO: 21)

A suitable target sequence in the human Ang1 cDNA sequence is:

AATGCAGTTCAGAACCACACG (SEQ ID NO: 22)

Thus, an siRNA of the invention targeting SEQ ID NO: 22, and which has 3' uu overhangs on each strand (overhangs shown in bold), is:

5'-tgcagttcagaaccacacguu-3' (SEQ ID NO: 23)
3'-uu acgucaagucuugguguge-5' (SEQ ID NO: 24)

An siRNA of the invention targeting SEQ ID NO: 22, but having 3' TT overhangs on each strand (overhangs shown in bold) is:

5'-tgcagttcagaaccacacgTT-3' (SEQ ID NO: 25)
3'-TTacgucaagucuugguguge-5' (SEQ ID NO: 26)

Another target sequence from the human Ang1 cDNA is:
AACTTCTCGACTTGAGATACA (SEQ ID NO: 27)

An siRNA of the invention targeting SEQ ID NO: 27, but having 3' uu overhangs on each strand (overhangs shown in bold) is:

5'-cttctcgacttgagatacauu-3' (SEQ ID NO: 28)
3'-uugaagagcugaacucuaugu-5' (SEQ ID NO: 29)

An siRNA of the invention targeting SEQ ID NO: 27, but having 3' TT overhangs on each strand (overhangs shown in bold) is:

5'-cttctcgacttgagatacaTT-3' (SEQ ID NO: 30)
3'-TTgaagagcugaacucuaugu-5' (SEQ ID NO: 31)

Other Ang1, Ang2 and Tie2 target sequences, from which siRNA of the invention can be derived, include those given herein: Suitable human Ang1 target sequences include those of SEQ ID NOS; 32-227; suitable human Ang2 target sequences include those of SEQ ID NOS: 228-427; and suitable human Tie2 target sequences include those of SEQ ID NOS: 428-739. It is understood that the target sequences given herein are with reference to the human Ang1, Ang2 or Tie2 cDNA, and thus these sequences contain deoxythymidines represented by "T." One skilled in the art would understand that, in the actual target sequence of the mRNA, the deoxythymidines would be replaced by uridines ("u"). Likewise, a target sequence contained within an siRNA of the invention would also contain uridines in place of deoxythymidines.

The siRNA of the invention can be obtained using a number of techniques known to those of skill in the art. For example, the siRNA can be chemically synthesized or recombinantly produced using methods known in the art, such as the *Drosophila* in vitro system described in U.S. published application 2002/0086356 of Tuschl et al., the entire disclosure of which is herein incorporated by reference.

Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

Alternatively, siRNA can also be expressed from recombinant circular or linear DNA plasmids using any suitable promoter. Suitable promoters for expressing siRNA of the invention from a plasmid include, for example, the U6 or H1 RNA pol III promoter sequences and the cytomegalovirus promoter. Selection of other suitable promoters is within the skill in the art. The recombinant plasmids of the invention can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly. The use of recombinant plasmids to deliver siRNA of the invention to cells in vivo is discussed in more detail below.

siRNA of the invention can be expressed from a recombinant plasmid either as two separate, complementary RNA molecules, or as a single RNA molecule with two complementary regions.

Selection of plasmids suitable for expressing siRNA of the invention, methods for inserting nucleic acid sequences for expressing the siRNA into the plasmid, and methods of delivering the recombinant plasmid to the cells of interest are within the skill in the art. See, for example Tuschl, T. (2002), *Nat. Biotechnol*, 20: 446-448; Brummelkamp T R et al. (2002), *Science* 296: 550-553; Miyagishi M et al. (2002), *Nat. Biotechnol.* 20: 497-500; Paddison P J et al. (2002), *Genes Dev.* 16: 948-958; Lee N S et al. (2002), *Nat. Biotechnol.* 20: 500-505; and Paul C P et al. (2002), *Nat. Biotechnol.* 20: 505-508, the entire disclosures of which are herein incorporated by reference.

In one embodiment, a plasmid expressing an siRNA of the invention comprises a sense RNA strand coding sequence in operable connection with a polyT termination sequence under the control of a human U6 RNA promoter, and an antisense RNA strand coding sequence in operable connection with a polyT termination sequence under the control of a human U6 RNA promoter. Such a plasmid can be used in producing an recombinant adeno-associated viral vector for expressing an siRNA of the invention.

As used herein, "in operable connection with a polyT termination sequence" means that the nucleic acid sequences encoding the sense or antisense strands are immediately adjacent to the polyT termination signal in the 5' direction. During transcription of the sense or antisense sequences from the plasmid, the polyT termination signals act to terminate transcription.

As used herein, "under the control" of a promoter means that the nucleic acid sequences encoding the sense or antisense strands are located 3' of the promoter, so that the promoter can initiate transcription of the sense or antisense coding sequences.

The siRNA of the invention can also be expressed from recombinant viral vectors intracellularly in vivo. The recombinant viral vectors of the invention comprise sequences encoding the siRNA of the invention and any suitable promoter for expressing the siRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the siRNA in a particular tissue or in a particular intracellular environment. The use of recombinant viral vectors to deliver siRNA of the invention to cells in vivo is discussed in more detail below.

siRNA of the invention can be expressed from a recombinant viral vector either as two separate, complementary RNA molecules, or as a single RNA molecule with two complementary regions.

Any viral vector capable of accepting the coding sequences for the siRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), *J Virol* 76:791-801, the entire disclosure of which is herein incorporated by reference.

Selection of recombinant viral vectors suitable for use in the invention, methods for inserting nucleic acid sequences for expressing the siRNA into the vector, and methods of delivering the viral vector to the cells of interest are within the skill in the art. See, for example, Dornburg R (1995), *Gene Therap.* 2: 301-310; Eglitis M A (1988), *Biotechniques* 6: 608-614; Miller A D (1990), *Hum Gene Therap.* 1: 5-14; Anderson W F (1998), Nature 392: 25-30; and Rubinson D A et al., *Nat. Genet.* 33: 401-406, the entire disclosures of which are herein incorporated by reference.

Preferred viral vectors are those derived from AV and AAV. In a particularly preferred embodiment, the siRNA of the invention is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the siRNA of the invention, a method for constructing the recombinant AV vector, and a method for delivering the vector into target cells, are described in Xia H et al. (2002), *Nat. Biotech.* 20: 1006-1010.

Suitable AAV vectors for expressing the siRNA of the invention, methods for constructing the recombinant AV vector, and methods for delivering the vectors into target cells are described in Samulski R et al. (1987), *J. Virol.* 61: 3096-3101; Fisher K J et al. (1996), *J. Virol.*, 70: 520-532; Samulski R et al. (1989), *J. Virol.* 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

The ability of an siRNA containing a given target sequence to cause RNAi-mediated degradation of the target mRNA can be evaluated using standard techniques for measuring the levels of RNA or protein in cells. For example, siRNA of the invention can be delivered to cultured cells, and the levels of target mRNA can be measured by Northern blot or dot blotting techniques, or by quantitative RT-PCR. Alternatively, the levels of Ang1, Ang2 or Tie2 protein in the cultured cells can be measured by ELISA or Western blot. Suitable protocols for the delivery of siRNA to cultured cells, and assays for detecting protein and mRNA levels in cultured cells, are given in the Examples below.

For example, cells which naturally express Ang1, Ang2 or Tie2, or which are induced to express Ang1, Ang2 or Tie2, are grown to confluence in suitable cell culture vessels; e.g., 12- or 25-well culture plates or 96-well microtiter plates. siRNA of the invention can be administered to one group of Ang1, Ang2 or Tie2 expressing cells. A non-specific siRNA (or no siRNA) can be administered to a second group of Ang1, Ang2 or Tie2 expressing cells as a control. The cells are washed and directly fixed to the microtiter plate wells with 1 to 2% paraformaldehyde. Nonspecific binding sites on the microtiter plate are blocked with 2% bovine serum albumin, and the cells incubated with an Ang1, Ang2 or Tie2 specific monoclonal antibody. Bound Ang1, Ang2 or Tie2 antibody can be detected, for example, by incubation with a 1:1000 dilution of biotinylated goat anti-mouse IgG (Bethesda Research Laboratories, Gaithersberg, Md.) for 1 hour at 37° C. and with a 1:1000 dilution of streptavidin conjugated to beta-galactosidase (Bethesda Research Laboratories) for 1 hour at 37° C. The amount of beta-galactosidase bound to the Ang1, Ang2 or Tie2 specific monoclonal antibody is determined, for example, by developing the microtiter plate in a solution of 3.3 mM chlorophenolred-beta-D-galactopyranoside, 50 mM sodium phosphate, 1.5 mM $MgCl_2$; pH 7.2 for 2 to 15 minutes at 37° C., and measuring the concentration of bound antibody at 575 nm in an ELISA microtiter plate reader.

The ability of the present siRNA to down-regulate Ang1, Ang2 or Tie2 expression can also be evaluated in vitro by measuring tube formation by bovine retinal endothelial cells (BRECs), using techniques within the skill in the art. An inhibition of tube formation indicates a down-regulation of Ang1, Ang2 or Tie2 by the present siRNA.

A suitable BREC tube formation assay comprises culturing BRECs on fibronectin-coated dishes containing Dulbecco's modified Eagle's medium (DMEM) with 5.5 mM glucose, 10% platelet-derived horse serum (PDHS; Wheaton, Pipersville, Pa.), 50 mg/mL heparin, and 50 U/mL endothelial cell growth factor (Roche Molecular Biochemicals). BRECs suitable for use in the tube-formation assay exhibit endothelial homogeneity by immunoreactivity for factor VIII antigen, and remain morphologically unchanged under these conditions as confirmed by light microscopy.

The tube formation assay can be performed as described in King G L et al., *J. Clin. Invest.* 75:1028-1036 (1985) and Otani A et al., *Circ. Res.* 82: 619-628 (1998), the entire disclosures of which are herein incorporated by reference. Briefly, an 8:1:1 (400 microliter) mixture of Vitrogen 100 (Celtrix, Palo Alto, Calif.), 0.2 N NaOH and 200 mM HEPES in 10×RPMI medium (Gibco BRL, Gaithersburg, Md.), containing 5 microgram/mL fibronectin and 5 microgram/mL laminin, is added to 24-well plates. After polymerization of the gels, $1.0 \times 10^5$ of the cultured BRECs are seeded in the wells and incubated for 24 hours at 37° C. with DMEM containing 20% PDHS. The cell number is chosen to optimize the shape and tube length, as is known in the art (see King G L et al., 1985, supra and Otani A et al., 1998, supra). The medium is then removed, and additional collagen gel is introduced onto the cell layer. Before making the collagen gel, reference points can be randomly marked in the center area of the bottom of each well, in order to measure the density per surface area of any tubelike structures formed by the BRECs. Either VEGF or hypoxia-conditioned medium is then added to the wells to induce tube formation. One or more siRNA of the invention are then introduced into the BRECs of certain wells by any suitable procedure (see below). Other wells are treated with either no siRNA or a non-specific siRNA as controls. Inhibition of tube formation in the wells treated with siRNA as compared to the control wells indicates that expression of the target RNA has been has been inhibited.

RNAi-mediated degradation of Ang1, Ang2 or Tie2 mRNA by an siRNA of the invention can also be evaluated with animal models of neovascularization, such as the retinopathy of prematurity ("ROP") or choroidal neovascularization ("CNV") rat or mouse models. For example, areas of neovascularization in a CNV rat or mouse can be measured before and after administration of the present siRNA, as in Example 6 below. A reduction in the areas of neovascularization upon administration of the siRNA indicates the down-regulation of target mRNA and an inhibition of angiogenesis. Down-regulation of target mRNA and an inhibition of angiogenesis is also demonstrated below in the streptozotocin-induced diabetic retinopathy rat model (Example 3), a rat model of VEGF-induced retinal vascular permeability and leukostasis (Example 4), and a rat model of ocular neovascularization induced by corneal/limbal injury (Example 5).

The mouse model of ischemia-induced retinal neovascularization as described in Takagi et al., 2003, supra can also be used to detect RNAi-mediated degradation of Ang1, Ang2 or Tie2 with the present siRNA. Briefly, litters of 7-day-old ("postnatal day 7" or "P7") C57BL/6J mice are exposed to 75%±2% oxygen for 5 days, and are then returned to room air at P12 to produce retinal neovascularization. Mice of the same age, maintained in room air, serve as a control. Maximal retinal neovascularization is typically observed at P17, 5 days after return to room air. One or more siRNA of the invention are injected subretinally into one eye of each treatment animal on P12 and P14. Either no siRNA, or a non-specific siRNA is injected into the contralateral eye as a control. At P17, the mice are killed by cardiac perfusion of 1 mL 4% paraformaldehyde in PBS, and the eyes are enucleated and fixed in 4% paraformaldehyde overnight at 4° C. before paraffin embedding. Serial sections of the paraffin-embedded eyes can be obtained for observation of the extent of neovascularization in the retina. Reduced neovascularization in the retinas of eyes treated with one or more siRNA of the invention, as compared to controls, indicate inhibition in expression of the target mRNA.

As discussed above, the siRNA of the invention target can cause the RNAi-mediated degradation of Ang1, Ang2 or Tie2 mRNA, or alternative splice forms, mutants or cognates thereof. Degradation of the target mRNA by the present siRNA reduces the production of a functional gene product from the Ang1, Ang2 and/or Tie2 genes. Thus, the invention provides a method of inhibiting expression of Ang1, Ang2 or Tie2 in a subject, comprising administering an effective amount of an siRNA of the invention to the subject, such that the target mRNA is degraded. As the products of the Ang1, Ang2 or Tie2 genes are involved in angiogenesis, the invention also provides a method of inhibiting angiogenesis in a subject by the RNAi-mediated degradation of the target mRNA by the present siRNA.

In the practice of the present methods, two or more siRNA comprising different target sequences in the Ang1, Ang2 or Tie2 mRNA can be administered to the subject. Likewise, two or more siRNA, each comprising target sequences from a different target mRNA (i.e., Ang1, Ang2 and Tie2 mRNA) can also be administered to a subject.

As discussed above, Ang1 or Ang2 in conjunction with Tie2 appear to promote angiogenesis in the presence of VEGF, and Ang2 in conjunction with Tie2 appears to promote angiogenesis under hypoxic conditions. However, it is not clear whether VEGF and/or hypoxic conditions are required for Ang1-, Ang2- and Tie2-mediated angiogenesis. Also, downregulation of either Ang1, Ang2 or Tie2 expression alone can be sufficient to inhibit angiogenesis. It is therefore not necessary to verify the presence of VEGF or hypoxia in the practice of the present methods.

As used herein, a "subject" includes a human being or non-human animal. Preferably, the subject is a human being.

As used herein, an "effective amount" of the siRNA is an amount sufficient to cause RNAi-mediated degradation of the target mRNA, or an amount sufficient to inhibit the progression of angiogenesis in a subject.

RNAi-mediated degradation of the target mRNA can be detected by measuring levels of the target mRNA or protein in the cells of a subject, using standard techniques for isolating and quantifying mRNA or protein as described above.

Inhibition of angiogenesis can be evaluated by directly measuring the progress of pathogenic or nonpathogenic angiogenesis in a subject; for example, by observing the size of a neovascularized area before and after treatment with the siRNA of the invention. An inhibition of angiogenesis is indicated if the size of the neovascularized area stays the same or is reduced. Techniques for observing and measuring the size of neovascularized areas in a subject are within the skill in the art; for example, areas of choroid neovascularization can be observed by ophthalmoscopy.

Inhibition of angiogenesis can also be inferred through observing a change or reversal in a pathogenic condition associated with the angiogenesis. For example, in AMD, a slowing, halting or reversal of vision loss indicates an inhibition of angiogenesis in the choroid. For tumors, a slowing, halting or reversal of tumor growth, or a slowing or halting of tumor metastasis, indicates an inhibition of angiogenesis at or near the tumor site. Inhibition of non-pathogenic angiogenesis can also be inferred from, for example, fat loss or a reduction in cholesterol levels upon administration of the siRNA of the invention.

It is understood that the siRNA of the invention can mediate RNA interference (and thus inhibit angiogenesis) in sub-stoichiometric amounts. Without wishing to be bound by any theory, it is believed that the siRNA of the invention induces the RISC to degrade the target mRNA in a catalytic manner. Thus, compared to standard therapies for cell adhesion or cell adhesion mediated pathologies, significantly less siRNA needs to be administered to the subject to have a therapeutic effect.

One skilled in the art can readily determine an effective amount of the siRNA of the invention to be administered to a given subject, by taking into account factors such as the size and weight of the subject; the extent of the neovascularization or disease penetration; the age, health and sex of the subject; the route of administration; and whether the administration is regional or systemic. Generally, an effective amount of the siRNA of the invention comprises an intercellular concentration at or near the neovascularization site of from about 1 nanomolar (nM) to about 100 nM, preferably from about 2 nM to about 50 nM, more preferably from about 2.5 nM to about 10 nM. Particularly preferred effective amounts of the siRNA of the invention can comprise an intercellular concentration at or near the neovascularization site of about 1 nM, about 5 nM, or about 25 nM. It is contemplated that greater or lesser effective amounts of siRNA can be administered.

The present methods can be used to inhibit angiogenesis which is non-pathogenic; i.e., angiogenesis which results from normal processes in the subject. Examples of non-pathogenic angiogenesis include endometrial neovascularization, and processes involved in the production of fatty tissues or cholesterol. Thus, the invention provides a method for inhibiting non-pathogenic angiogenesis; e.g., for controlling weight or promoting fat loss, for reducing cholesterol levels, an inhibitor of the menstrual cycle, or as an abortifacient.

The present methods can also inhibit angiogenesis which is associated with an angiogenic disease; i.e., a disease in which pathogenicity is associated with inappropriate or uncontrolled angiogenesis. For example, most cancerous solid tumors generate an adequate blood supply for themselves by inducing angiogenesis in and around the tumor site. This tumor-induced angiogenesis is often required for tumor growth, and also allows metastatic cells to enter the bloodstream.

Other angiogenic diseases include AMD, psoriasis, rheumatoid arthritis and other inflammatory diseases. These diseases are characterized by the destruction of normal tissue by newly formed blood vessels in the area of neovascularization. For example, in the wet form of AMD, the choroid is invaded and destroyed by capillaries. The angiogenesis-driven destruction of the choroid in AMD eventually leads to partial or full blindness.

In another embodiment, the invention provides a method of treating a subject for complications arising from type I diabetes, by the RNAi-mediated degradation of the target mRNA by the present siRNA. Preferably, the complications arising from type I diabetes to be treated by the present method are diabetic retinopathy, diabetic neuropathy, diabetic nephropathy, and macrovascular disease (including coronary artery disease, cerebrovascular disease, and peripheral vascular disease).

Preferably, an siRNA of the invention is used to inhibit the growth or metastasis of solid tumors associated with cancers; for example breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma; skin cancer (e.g., melanoma), lymphomas and blood cancer.

More preferably, an siRNA of the invention is used to treat complications arising from type I diabetes, such as diabetic retinopathy, diabetic neuropathy, diabetic nephropathy and macrovascular disease.

Particularly preferably, an siRNA of the invention is used to inhibit ocular neovascularization, for example to inhibit choroidal neovascularization in AMD.

For treating angiogenic diseases, the siRNA of the invention can administered to a subject in combination with a pharmaceutical agent which is different from the present siRNA. Alternatively, the siRNA of the invention can be administered to a subject in combination with another therapeutic method designed to treat the angiogenic disease. For example, the siRNA of the invention can be administered in combination with therapeutic methods currently employed for treating cancer or preventing tumor metastasis (e.g., radiation therapy, chemotherapy, and surgery). For treating tumors, the siRNA of the invention is preferably administered to a subject in combination with radiation therapy, or in combination with chemotherapeutic agents such as cisplatin, carboplatin, cyclophosphamide, 5-fluorouracil, adriamycin, daunorubicin or tamoxifen.

In the present methods, the present siRNA can be administered to the subject either as naked siRNA, in conjunction with a delivery reagent, or as a recombinant plasmid or viral vector which expresses the siRNA.

Suitable delivery reagents for administration in conjunction with the present siRNA include the Minis Transit TKO lipophilic reagent; lipofectin; lipofectamine; cellfectin; or polycations (e.g., polylysine), or liposomes. A preferred delivery reagent is a liposome.

Liposomes can aid in the delivery of the siRNA to a particular tissue, such as retinal or tumor tissue, and can also increase the blood half-life of the siRNA. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), *Ann. Rev. Biophys. Bioeng.* 9: 467; and U.S. Pat. Nos. 4,235,871, 4,501,728, 4,837,028, and 5,019,369, the entire disclosures of which are herein incorporated by reference.

Preferably, liposomes encapsulating the present siRNA comprise a ligand molecule that can target the liposome to cells such as endothelial cells which express Ang1, Ang2 or Tie2 at or near the site of angiogenesis. Ligands which bind to receptors prevalent in vascular EC, such as monoclonal antibodies that bind to EC surface antigens, are preferred.

Particularly preferably, the liposomes encapsulating the present siRNA's are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, tissue characterized by such microvasculature defects, for example solid tumors, will efficiently accumulate these liposomes; see Gabizon, et al. (1988), *P.N.A.S., USA,* 18: 6949-53. In addition, the reduced uptake by the RES lowers the toxicity of stealth liposomes by preventing significant accumulation in the liver and spleen. Thus, liposomes of the invention that are modified with opsonization-inhibition moieties are particularly suited to deliver the present siRNA to tumor cells.

Opsonization inhibiting moieties suitable for modifying liposomes are preferably water-soluble polymers with a number average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside $GM_1$. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

Preferably, the opsonization-inhibiting moiety is a PEG, PPG, or derivatives thereof. Liposomes modified with PEG or PEG-derivatives are sometimes called "PEGylated liposomes."

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture such as tetrahydrofuran and water in a 30:12 ratio at 60° C.

Recombinant plasmids which express siRNA of the invention are discussed above. Such recombinant plasmids can also be administered directly or in conjunction with a suitable delivery reagent, including the Mirus Transit LT1 lipophilic reagent; lipofectin; lipofectamine; cellfectin; polycations (e.g., polylysine) or liposomes. Recombinant viral vectors which express siRNA of the invention are also discussed above, and methods for delivering such vectors to cells of a subject which are expressing Ang1, Ang2 or Tie2 are within the skill in the art.

The siRNA of the invention can be administered to the subject by any means suitable for delivering the siRNA to the cells expressing Ang1, Ang2 or Tie2. For example, the siRNA can be administered by gene gun, electroporation, or by other suitable parenteral or enteral administration routes.

Suitable enteral administration routes include oral, rectal, or intranasal delivery.

Suitable parenteral administration routes include intravascular administration (e.g. intravenous bolus injection, intravenous infusion, intra-arterial bolus injection, intra-arterial infusion and catheter instillation into the vasculature); peri- and intra-tissue administration (e.g., peri-tumoral and intra-tumoral injection, intra-retinal injection or subretinal injection); subcutaneous injection or deposition including subcutaneous infusion (such as by osmotic pumps); direct (e.g., topical) application to the area at or near the site of neovascularization, for example by a catheter or other placement device (e.g., a corneal pellet or a suppository, eye-dropper, or an implant comprising a porous, non-porous, or gelatinous material); and inhalation. Suitable placement devices include the ocular implants described in U.S. Pat. Nos. 5,902,598 and 6,375,972, and the biodegradable ocular implants described in U.S. Pat. No. 6,331,313, the entire disclosures of which are herein incorporated by reference. Such ocular implants are available from Control Delivery Systems, Inc. (Watertown, Mass.) and Oculex Pharmaceuticals, Inc. (Sunnyvale, Calif.).

In a preferred embodiment, injections or infusions of the siRNA are given at or near the site of neovascularization. For example, the siRNA of the invention can be delivered to retinal pigment epithelial cells in the eye. Preferably, the siRNA is administered topically to the eye, e.g. in liquid or gel form to the lower eye lid or conjunctival cul-de-sac, or by electroporation or iontophoresis, as is within the skill in the art (see, e.g., Acheampong A A et al, 2002, *Drug Metabol. and Disposition* 30: 421-429, the entire disclosure of which is herein incorporated by reference).

Typically, the siRNA of the invention is administered topically to the eye in volumes of from about 5 microliters to about 75 microliters, for example from about 7 microliters to about 50 microliters, preferably from about 10 microliters to about 30 microliters. The siRNA of the invention is highly soluble in aqueous solutions, and it is understood that topical instillation in the eye of siRNA in volumes greater than 75 microliters can result in loss of siRNA from the eye through spillage and drainage. Thus, it is preferable to administer a high concentration of siRNA (e.g., about 10 to about 200 mg/ml, or about 100 to about 1000 nM) by topical instillation to the eye in volumes of from about 5 microliters to about 75 microliters.

A particularly preferred parenteral administration route is intraocular administration. It is understood that intraocular administration of the present siRNA can be accomplished by injection or direct (e.g., topical) administration to the eye, as long as the administration route allows the siRNA to enter the eye. In addition to the topical routes of administration to the eye described above, suitable intraocular routes of administration include intravitreal, intraretinal, subretinal, subtenon, peri- and retro-orbital, trans-corneal and trans-scleral administration. Such intraocular administration routes are within the skill in the art; see, e.g., and Acheampong A A et al, 2002, supra; and Bennett et al. (1996), *Hum. Gene Ther.* 7: 1763-1769 and Ambati J et al., 2002, *Progress in Retinal and Eye Res.* 21: 145-151, the entire disclosures of which are herein incorporated by reference.

The siRNA of the invention can be administered in a single dose or in multiple doses. Where the administration of the siRNA of the invention is by infusion, the infusion can be a single sustained dose or can be delivered by multiple infusions.

One skilled in the art can also readily determine an appropriate dosage regimen for administering the siRNA of the invention to a given subject. For example, the siRNA can be administered to the subject once, such as by a single injection or deposition at or near the neovascularization site. Alternatively, the siRNA can be administered to a subject multiple times daily or weekly. For example, the siRNA can be administered to a subject once weekly for a period of from about three to about twenty-eight weeks, more preferably from about seven to about ten weeks. In a preferred dosage regimen, the siRNA is injected at or near the site of neovascularization (e.g., intravitreally) once a week for seven weeks. It is understood that periodic administrations of the siRNA of the invention for an indefinite length of time may be necessary for subjects suffering from a chronic neovascularization disease, such as wet AMD or diabetic retinopathy.

Where a dosage regimen comprises multiple administrations or the administration of two or more siRNA, each of which comprise a different target sequence, it is understood that the effective amount of siRNA administered to the subject can comprise the total amount of siRNA administered over the entire dosage regimen.

The siRNA of the invention are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in *Remington's Pharmaceutical Science*, 17th ed., Mack Publishing Company, Easton, Pa. (1985), the entire disclosure of which is herein incorporated by reference.

The present pharmaceutical formulations comprise an siRNA of the invention (e.g., 0.1 to 90% by weight), or a physiologically acceptable salt thereof, mixed with a physiologically acceptable carrier medium. Preferred physiologically acceptable carrier media are water, buffered water, normal saline, 0.4% saline, 0.3% glycine, hyaluronic acid and the like.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For topical administration to the eye, conventional intraocular delivery reagents can be used. For example, pharmaceutical compositions of the invention for topical intraocular delivery can comprise saline solutions as described above, corneal penetration enhancers, insoluble particles, petrolatum or other gel-based ointments, polymers which undergo a viscosity increase upon instillation in the eye, or mucoadhesive polymers. Preferably, the intraocular delivery reagent increases corneal penetration, or prolongs preocular retention of the siRNA through viscosity effects or by establishing physicochemical interactions with the mucin layer covering the corneal epithelium.

Suitable insoluble particles for topical intraocular delivery include the calcium phosphate particles described in U.S. Pat. No. 6,355,271 of Bell et al., the entire disclosure of which is herein incorporated by reference. Suitable polymers which undergo a viscosity increase upon instillation in the eye include polyethylenepolyoxypropylene block copolymers such as poloxamer 407 (e.g., at a concentration of 25%), cellulose acetophthalate (e.g., at a concentration of 30%), or a low-acetyl gellan gum such as Gelrite® (available from CP Kelco, Wilmington, Del.). Suitable mucoadhesive polymers include hydrocolloids with multiple hydrophilic functional groups such as carboxyl, hydroxyl, amide and/or sulfate groups; for example, hydroxypropylcellulose, polyacrylic acid, high-molecular weight polyethylene glycols (e.g., >200,000 number average molecular weight), dextrans, hyaluronic acid, polygalacturonic acid, and xylocan. Suitable corneal penetration enhancers include cyclodextrins, benzalkonium chloride, polyoxyethylene glycol lauryl ether (e.g., Brij® 35), polyoxyethylene glycol stearyl ether (e.g., Brij® 78), polyoxyethylene glycol oleyl ether (e.g., Brij® 98), ethylene diamine tetraacetic acid (EDTA), digitonin, sodium taurocholate, saponins and polyoxyethylated castor oil such as Cremaphor EL.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of one or more siRNA of the invention. A pharmaceutical composition for aerosol (inhalational) administration can comprise 0.01-20% by weight, preferably 1%-10% by weight, of one or more siRNA of the invention encapsulated in a liposome as described above, and propellant. A carrier can also be included as desired; e.g., lecithin for intranasal delivery.

The invention will now be illustrated by the following non-limiting examples.

Example 1

Inhibition of Ang2 Expression in Cultured Human Cells with siRNA Targeted to Ang2 mRNA Human embryonic kidney (HEK-293 cells) were cultured in 24 well plates at 37° C. with 5% $CO_2$ overnight in standard growth medium. Transfections were performed the next day when the cells were about 70% confluent. The HEK-293 cells were separately transfected with twelve different siRNA (25 nM each) targeted to human Ang2 ("hANG2") mRNA, mixed with a CaPi transfection reagent. These twelve siRNAs target the sequences listed in Table 1, and all siRNAs contained 3' TT overhangs on each strand. Control cells were transfected with CaPi transfection reagent lacking siRNA, or a nonspecific siRNA targeted to enhanced green fluorescent protein (EGFP siRNA) mixed with CaPi transfection reagent. Forty eight hours post-transfection, the growth medium was removed from all wells, and a human ANG2 ELISA (R & D systems, Minneapolis, Minn.) was performed as described in the Quantikine human ANG2 ELISA protocol, the entire disclosure of which is herein incorporated by reference. ELISA results were read on an AD340 plate reader (Beckman Coulter), and are reported in FIG. 1.

TABLE 1

Target Sequences for hANG2 siRNAs Tested in HEK-293 Cells

| Target Sequence | SEQ ID NO: | siRNA |
|---|---|---|
| AAGAGCATGGACAGCATAGGA | 232 | hANG2#1 |
| AACCAGACGGCTGTGATGATA | 254 | hANG2#2 |
| AAACGCGGAAGTTAACTGATG | 262 | hANG2#3 |
| AACGCGGAAGTTAACTGATGT | 263 | hANG2#4 |
| AAGAAGGTGCTAGCTATGGAA | 291 | hANG2#5 |
| AATAGTGACTGCCACGGTGAA | 316 | hANG2#6 |
| AATAACTTACTGACTATGATG | 323 | hANG2#7 |
| AATCAGGACACACCACAAATG | 336 | hANG2#8 |

TABLE 1-continued

Target Sequences for hANG2 siRNAs Tested in HEK-293 Cells

| Target Sequence | SEQ ID NO: | siRNA |
|---|---|---|
| AAATGGCATCTACACGTTAAC | 337 | hANG2#9 |
| AATGGCATCTACACGTTAACA | 338 | hANG2#10 |
| AATTATTCAGCGACGTGAGGA | 344 | hANG2#11 |
| AAGAACTCAATTATAGGATTC | 366 | hANG2#12 |

As can be seen from FIG. 1, the level of hANG2 protein secreted into the growth medium was reduced in HEK-293 cells transfected with hANG2#2, #3, #4, #9 and #10 siRNA. Transfection of HEK-293 cells with non-specific siRNA had no apparent effect on hANG2 protein levels.

After the growth medium was removed from each well, a cytotoxicity assay was performed on the cells as follows. Complete growth medium containing 10% AlamarBlue (Biosource, Camarillo, Calif.) was added to each well, and cells were incubated at 37° C. with 5% $CO_2$ for 3 hours. Cell proliferation was measured by detecting the color change of medium containing AlamarBlue which resulted from cell metabolic activity. The cytotoxicity assay results were read on an AD340 plate reader (Beckman Coulter), and are reported in FIG. 2.

Figure 2:
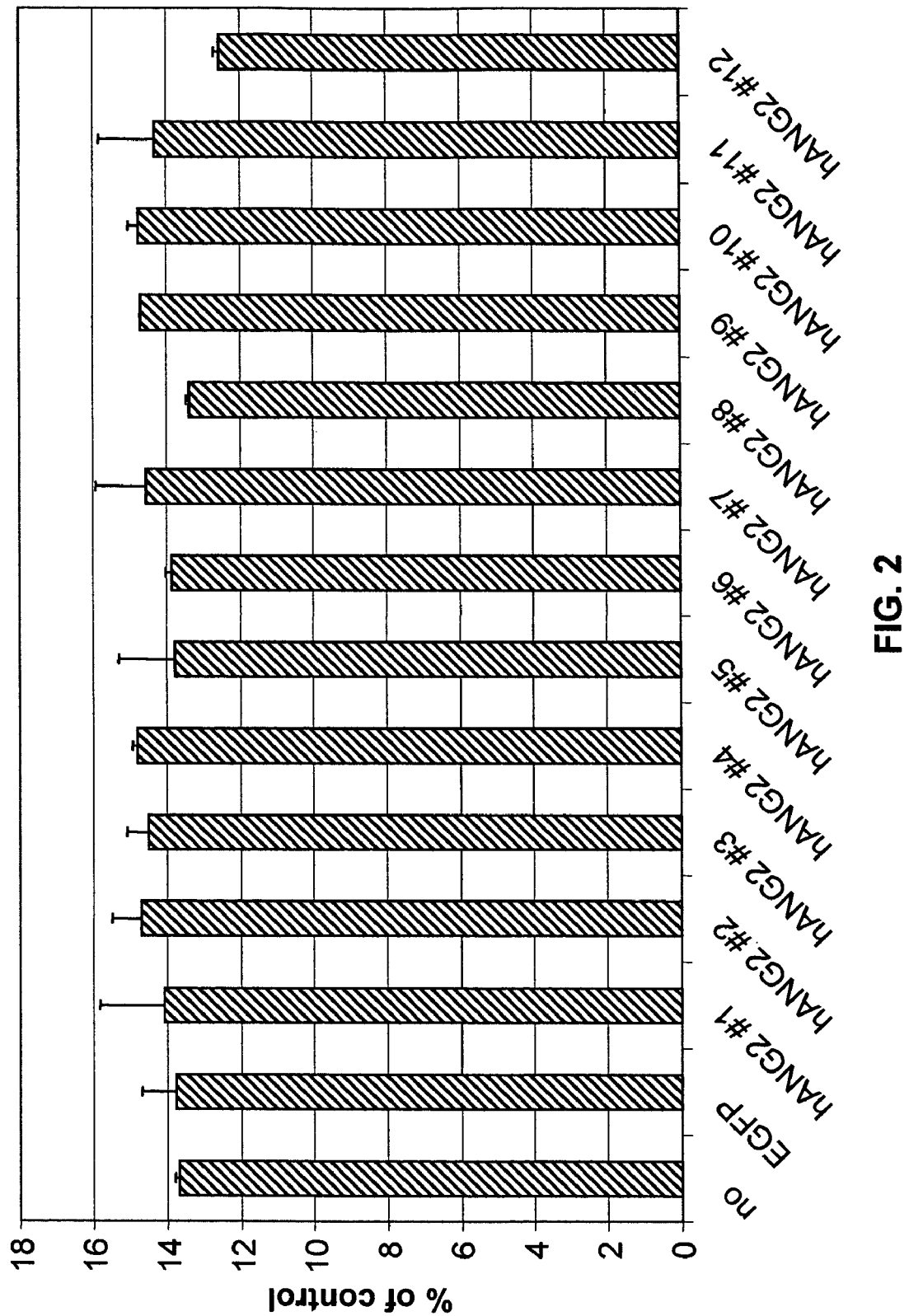
FIG. 2 is a histogram showing lack of cytotoxicity in HEK-293 cells transfected with twelve different siRNA targeted to hANG2 mRNA (hANG2#1-hANG2#12). Control cells were transfected with nonspecific siRNA targeted to enhanced green fluorescent protein mRNA ("EGFP"), or with transfection reagent containing no siRNA ("no"). Cytotoxicity is measured as percent growth of cells treated with siRNA vs. cells treated with transfection reagent alone.

As can be seen in FIG. 2, the transfection of HEK-293 cells with the hANG2#8 and #12 siRNA produced a slight reduction in cell growth as compared to control cells. The remaining hANG2 siRNAs showed no apparent cytotoxicity as compared with control cells.

After cytotoxicity assay was performed, the AlamarBlue-containing medium in each well was completely removed and RNA extractions were performed using the RNAqueous RNA isolation kit (Ambion, Austin, Tex.). The levels of hANG2 mRNA in the HEK-293 cells were measured by a quantitative reverse-transcriptase/polymerase chain reaction (RT-PCR) assay. Expression of human glyceraldehyde-3-phosphate dehydrogenase (GAPDH) mRNA was used as a internal control. The levels of hANG2 mRNA in HEK-293 cells were reduced by transfection with the hANG2 siRNA compared to control cells, in a pattern which correlated with the reduction in hANG2 protein shown in FIG. 1.

Example 2

Dose-Response of hAng2 #2 and #3 in Cultured Human Cells

HEK-293 cells were grown to about 70% confluency as in Example 1 above. The cells were then transfected with 1 nanomolar ("nM"), 5 nM or 25 nM doses of hANG2#2 or #3 siRNA in CaPi transfection reagent. Control cells were transfected with 25 nM nonspecific EGFP siRNA in CaPi transfection reagent, or with transfection reagent alone. hANG2 protein levels were measured in the growth medium at 48 hours post-transfection by ANG2 ELISA as described in Example 1 above, and the results are presented in FIG. 3.

Figure 3:
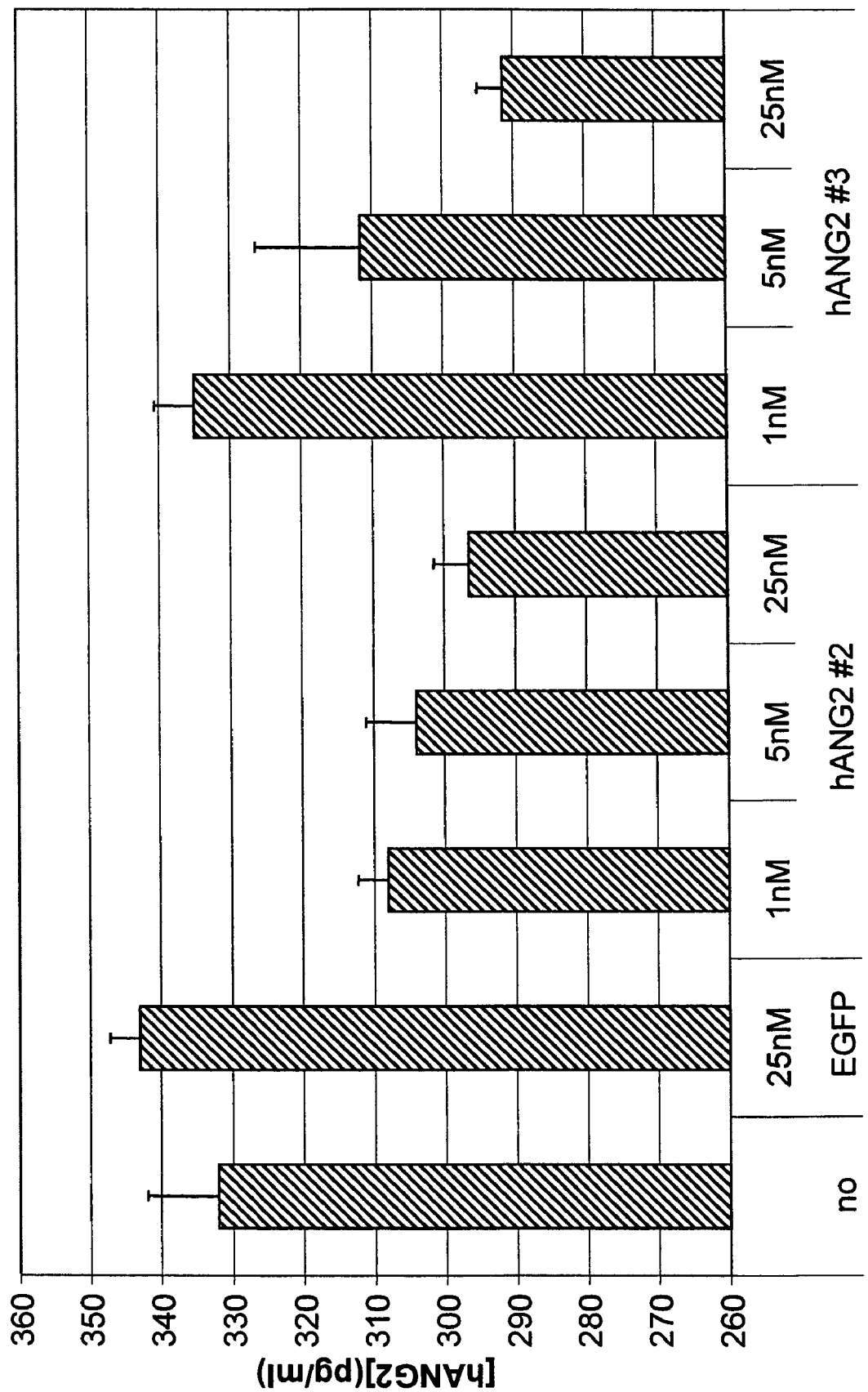
FIG. 3 is a histogram showing the silencing effect of increasing doses of hANG2#2 and hANG2#3 on the level of hANG2 protein secreted by HEK-293 cells. The HEK-293 cells were transfected with 1 nanomolar ("nM"), 5 nM, or 25 nM hANG2#2 or hANG2#3 siRNA. Control cells were transfected with 25 nM nonspecific siRNA targeted to enhanced green fluorescent protein mRNA ("EGFP"), or with transfection reagent containing no siRNA ("no"). hANG2 protein level is given in picograms of protein per milliliter of growth medium (pg/ml), as measured by hANG2 ELISA at 48 hours post-transfection.

As can be seen from FIG. 3, the levels of hANG2 protein level were reduced in HEK-293 cells transfected with the hANG2#2 and #3 siRNA, in a dose-dependent manner. All doses of hANG2#2 siRNA and the 5 and 25 nM doses of hANG2#3 siRNA reduced the level of hANG2 protein secreted into the growth medium, as compared to control cells. The 1 nM dose of hANG2#3 siRNA did not reduce the hANG2 protein level as compared to control cells mock-transfected with transfection reagent alone. However, the level of hANG2 protein secreted by cells transfected with 1 nM hANG2#3 siRNA was slightly reduced as compared to control cells transfected with the nonspecific siRNA. Transfections with the non-specific siRNA had no apparent effect on hANG2 protein levels.

Figure 4:
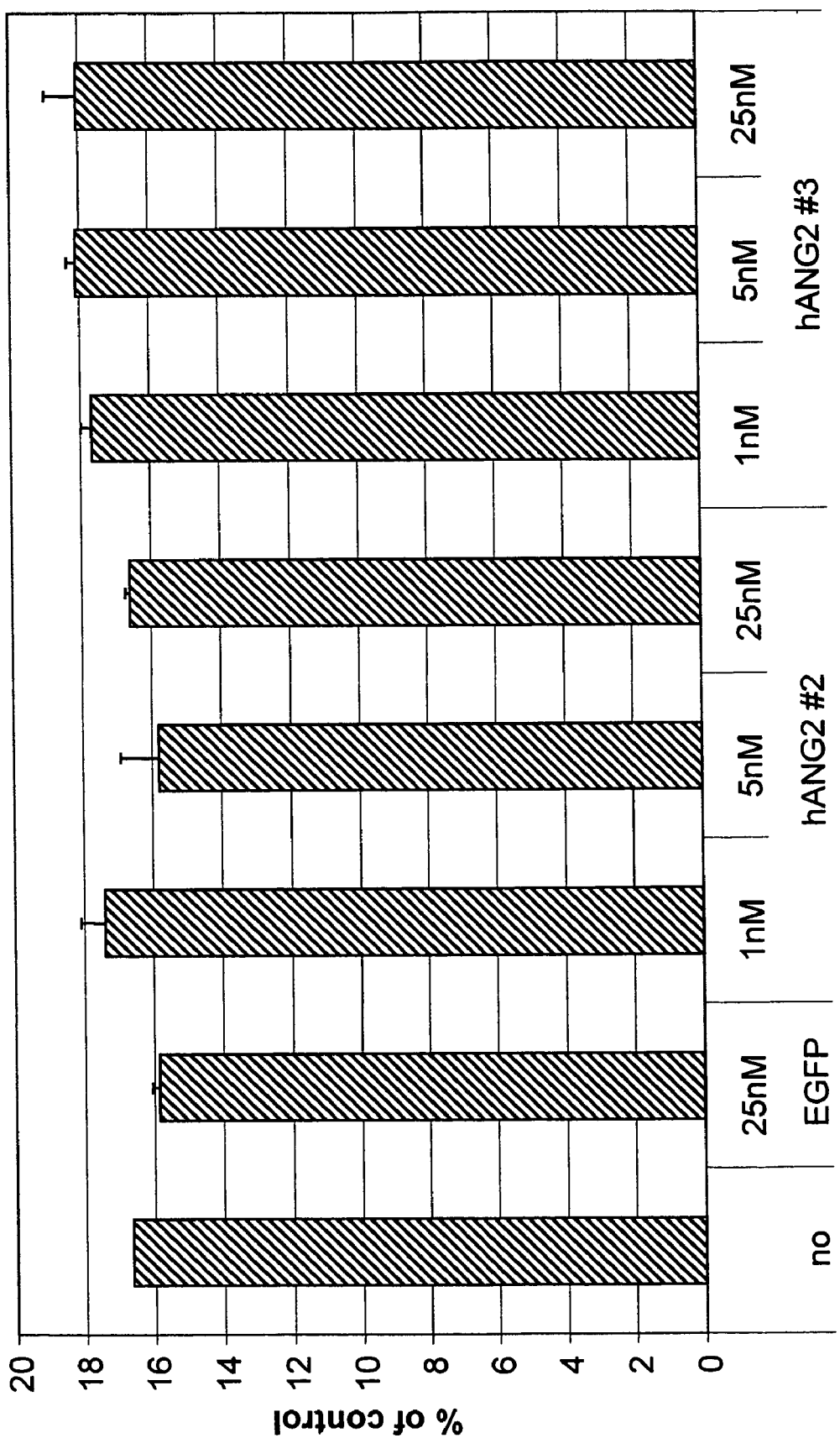
FIG. 4 is a histogram showing lack of cytotoxicity in HEK-293 cells transfected with increasing doses of hANG2#2 and hANG2#3 siRNA. Control cells were transfected with nonspecific siRNA targeted to enhanced green fluorescent protein mRNA ("EGFP"), or with transfection reagent containing no siRNA ("no"). Cytotoxicity is measured as percent growth of cells treated with siRNA vs. cells treated with transfection reagent alone.

A cytotoxicity assay was performed on the control HEK-293 cells and the HEK-293 cells transfected with the different doses of hANG2#2 and #3 siRNA as described above in Example 1. As can be seen in FIG. 4, the transfection of HEK-293 cells with 5 nM hANG2#2 siRNA produced a slight reduction in cell growth as compared to control cells mock-transfected with transfection reagent alone. There was no apparent toxicity of the 5 nM hANG2#2 siRNA dose as compared to control cells transfected with the nonspecific siRNA. The remaining doses of hANG2#2 or #3 siRNA showed no apparent cytotoxicity as compared with control cells transfected with nonspecific siRNA or with transfection reagent alone.

Example 3

Treatment of Streptozotocin-Induced Diabetic Retinopathy with siRNA Targeted to Ang1, Ang2 or Tie2

Vascular leakage and non-perfusion in the retinas of individuals with diabetic retinopathy is spatially and temporally associated with leukocyte stasis. See, e.g., Miyamoto K et al. (1999), *Proc. Nat. Acad. Sci. USA* 96(19):10836-41, the entire disclosure of which is herein incorporated by reference. It is expected that intravitreal injection of siRNA targeted to Ang1, Ang2 or Tie2 will decrease leukocyte stasis, and therefore reduce retinal vascular permeability, in diabetic rats.

Long-Evans rats (approximately 200 g) will be injected with streptozotocin in citrate buffer intravenously after an overnight fast to induce diabetes, as described in Miyamoto K et al. (1999), supra. Long-Evans rats (approximately 200 g) will be injected with citrate buffer alone after an overnight fast as a control. The serum blood sugar will be measured and blood pressure will be recorded daily. Elevated levels of serum blood sugar as compared to control animals are considered diabetic.

Intravitreal injections of siRNA targeted to Ang1, Ang2 or Tie2 ("experimental siRNA") will be performed OD in each rat. Non-specific siRNA will be injected as a control OS. The overall group scheme will be as shown in Table 2.

TABLE 2

| | Overall Group Scheme | |
|---|---|---|
| | OD (experimental siRNA) | OS (non-specific siRNA) |
| Diabetic Rat (STZ) | Experimental group | Control |
| Non-diabetic Rat | Control | Control |

At day 7 post treatment, the rats will be subjected to Acridine Orange Leukocyte Fluorography (AOLF), as described in Miyamoto K et al (1999), supra. Briefly, the rats will be anaesthetized, and their pupils dilated with tropicamide. The rats will then be injected intravenously with acridine orange suspended in sterile saline. The fundus of each eye will be observed and imaged with a scanning laser ophthalmoscope (argon blue laser as a light source) for leukocyte stasis. The rats will then be perfused with fluorescein dextran and the eyes will be further imaged. The density of leukocyte stasis will be calculated as a percentage of bright pixels in a 10 disk diameter radius. The density of leukocyte stasis will be used as an endpoint.

Also on day 7, the rats will undergo an isotope dilution technique to quantify vascular leakage, as described in Miyamoto K et al (1999), supra. Briefly, the rats will be injected intravenously with $I^{125}$ in BSA at one time point, and with $I^{131}$ at a second time point. The rats will be sacrificed minutes after the second injection, the retinas will be isolated, and arterial samples will be taken. The retinas and the arterial samples will be analyzed using γ-spectroscopy after correcting for activity in the retinas using a quantitative index of iodine clearance. The measurements will then be normalized for exact dose given, body weight and tissue weight. The corrected quantity of γ activity will be used as a marker of vascular leakage in the retina (second endpoint). It is expected that the γ activity will be decreased in the retinas of the experimental animals, indicating decreased vascular leakage.

Example 4

Treatment of VEGF-Induced Vascular Permeability and Leukostasis with siRNA Targeted to Ang1, Ang2 or Tie2

The presence of VEGF in the eye causes retinal leukostasis that corresponds with increased vascular permeability and capillary non-perfusion in the retina. See, e.g., Miyamoto K et al. (2000), Am. J. Pathol. 156(5):1733-9, the entire disclosure of which is herein incorporated by reference. It is expected that intravitreal injection of siRNA targeted to Ang1, Ang2 or Tie2 will decrease the permeability and leukostasis created by intravitreal injection of VEGF in rats.

Long-Evans rats (approximately 200 g) will be anaesthetized and injected intravitreally with VEGF in buffer OU. siRNA targeted to Ang1, Ang2 or Tie2 ("experimental siRNA") will be simultaneously delivered OD to each rat by intravitreal injection. Non-specific siRNA will be injected intravitreally as a control OS. Additional controls will include rats injected with buffer alone (no VEGF). The overall group scheme will be as shown in Table 3.

TABLE 3

| Overall Group Scheme | | |
|---|---|---|
| | OD (experimental siRNA) | OS (Non-specific siRNA) |
| VEGF | Experimental group | Control |
| Buffer | Control | Control |

At 24 hours post injection the rats are subjected to AOLF and an isotope dilution technique as described in Example 3.

Example 5

Treatment of Neovascularization in Eyes Subjected to Corneal/Limbal Injury with siRNA Targeted to Ang1, Ang2 or Tie2

Injury to the ocular surface can cause the destruction of corneal limbal stem cells. Destruction of these cells induces a VEGF-dependent corneal neovascularization, which can lead to blindness. The VEGF which drives the neovascularization is supplied by neutrophils and monocytes that infiltrate the cornea after injury to the ocular surface. See, e.g., Moromizato Y et al. (2000), Am. J. Pathol. 157(4):1277-81, the entire disclosure of which is herein incorporated by reference in its entirety. It is expected that siRNA targeted to Ang1, Ang2 or Tie2 applied to the cornea after limbal injury will decrease the resultant area of neovascularization of the cornea in mice. The area of neovascularization can be measured directly. Alternatively, a reduction in corneal neovascularization can be inferred from a decrease in the number of VEGF-producing polymorphonuclear cells in the cornea.

Corneal neovascularization will be induced in C57Bl/6 by damaging the limbus, as described in Moromizato Y et al., supra. Briefly, the mice will be anaesthetized and sodium hydroxide will be applied to the cornea. The corneal and limbal epithelia will be debrided using a corneal knife OU. siRNA targeted to Ang1, Ang2 or Tie2 will be applied to the corneal surface OD immediately after removal, and 3 times a day for the duration of the study (7 days). Non-specific siRNA will be administered OS with the same dosing regimen as a control.

On days 2, 4 and 7 after debridement of the corneal and limbal epithelia, mice will be evaluated for the degree of corneal neovascularization as described in Moromizato Y et al., supra. Briefly, endothelial-specific, fluorescein-conjugated lectin will be injected intravenously. Thirty minutes after injection, mice will be sacrificed, and the eyes will be harvested and fixed in formalin for 24 hours. Flat mounts of the corneas will be made, and pictures of the corneal flat mounts will be taken under fluorescent microscopy and imported into Openlab software for analysis. Using the Openlab software, threshold level of fluorescence will be set, above which only vessels are seen. The area of fluorescent vessels and the area of the cornea (demarcated by the limbal arcade) will be calculated. The area of vessels will be divided by the total corneal area, and this value will equal the percent neovascular area. The percent neovascular area of the treatment and control groups will be compared.

On days 2, 4 and 7 after debridement of the corneal and limbal epithelia, additional mice will be sacrificed for quantification of corneal polymorphonuclear cells (PMNs) as described in Moromizato Y et al., supra. Briefly, mice will be sacrificed, and the eyes will be harvested and fixed in formalin for 24 hours. After formalin fixation, the enucleated eyes will be embedded in paraffin and sectioned. One paraffin section from each eye which correlates to the corneal anatomical center will be chosen and used for microscopy. The PMNs (identified as multilobulated cells) will be counted on this one section, and the number of PMNs in the sections from the treatment and control groups will be compared.

Example 6

Treatment of Laser-Induced Choroidal Neovascularization with siRNA Targeted to Ang1, Ang2 or Tie2

Laser photocoagulation that ruptures Bruch's membrane will induce choroidal neovascularization (CNV) similar to that seen in wet macular degeneration. It is expected that intravitreal injection of siRNA targeted to Ang1, Ang2 or Tie2 will decrease the area of laser-induced CNV in mice.

CNV will be induced in mice by the procedure described in Sakurai E et al. (2003), Invest. Ophthalmol. & Visual Sci. 44(6):2743-9, the entire disclosure of which is herein incorporated by reference. Briefly, C57Bl/6 mice will be anaesthetized, and their pupils will be dilated with tropicamide. The retinas of the mice will be laser photocoagulated with one laser spot at the 9, 12, and 3 o'clock positions of each retinal OU. Immediately following laser photocoagulation, inject siRNA targeted to Ang1, Ang2 or Tie2 will be injected intravitreally OD. Non-specific siRNA will be injected intravitreally OS as a control.

Fourteen days after laser photocoagulation, the mice will be sacrificed and retinal flat mounts will be prepared for CNV area quantification as described in Sakurai E et al. (2003), supra. Briefly, the mice will be anaesthetized, the chest will be opened, and the descending aorta will be cross-clamped. The right atrium will then be clipped and fluorescein-labeled dextran will be injected slowly into the left ventricle.

After injection of the fluorescein-labeled dextran, the eyes will be enucleated and fixed in paraformaldehyde for 24 hours. The anterior chamber and retina will then be removed, and a flat mount of each choroid will be prepared for analysis. Choroidal flat mounts will be analyzed by taking a picture of each under fluorescent microscopy, and importing the picture into Openlab software. Using the Openlab software, the area of neovascularization will be outlined and quantified, being sure known laser location is compared to the fluorescent tuft. The neovascular area of the treatment animals will be compared to that of the control animals.

We claim:

1. A pharmaceutical composition comprising an effective amount of an siRNA and a pharmaceutically acceptable carrier, wherein the siRNA comprises a sense RNA strand and an antisense RNA strand, wherein the sense and an antisense RNA strands form an RNA duplex, and wherein the sense RNA strand comprises a nucleotide sequence substantially identical to a target sequence in human Ang2 mRNA, wherein said target sequence consists of SEQ ID NO: 254 or SEQ ID NO: 262, wherein said effective amount is effective to inhibit the expression of Ang2.

2. The pharmaceutical composition of claim 1, further comprising lipofectin, lipofectamine, cellfectin, polycations, or liposomes.

3. A pharmaceutical composition comprising a recombinant plasmid comprising nucleic acid sequences for expressing an siRNA comprising a sense RNA strand and an antisense RNA strand, wherein the sense and the antisense RNA strands form an RNA duplex, and wherein the sense RNA strand comprises a nucleotide sequence substantially identical to a target sequence in human Ang2 mRNA, wherein said target sequence consists of SEQ ID NO: 254 or SEQ ID NO: 262, or a physiologically acceptable salt thereof, and wherein the siRNA is expressed in an effective amount when the recombinant plasmid is administered to a subject and a pharmaceutically acceptable carrier, wherein said effective amount is effective to inhibit the expression of Ang2.

4. The pharmaceutical composition of claim 3, further comprising lipofectin, lipofectamine, cellfectin, polycations, or liposomes.

5. A pharmaceutical composition comprising a recombinant viral vector comprising nucleic acid sequences for expressing an siRNA comprising a sense RNA strand and an antisense RNA strand, wherein the sense and the antisense RNA strands form an RNA duplex, and wherein the sense RNA strand comprises a nucleotide sequence substantially identical to a target sequence in human Ang2 mRNA, wherein said target sequence consists of SEQ ID NO: 254 or SEQ ID NO: 262 wherein the siRNA is expressed in an effective amount when the recombinant viral vector is administered to a subject and a pharmaceutically acceptable carrier, wherein said effective amount is effective to inhibit the expression of Ang2.

6. A method of inhibiting expression of human Ang2 mRNA, or an alternative splice form, mutant or cognate thereof, comprising administering to a subject a pharmaceutical composition comprising an effective amount of an siRNA and a pharmaceutically acceptable carrier wherein the siRNA comprises a sense RNA strand and an antisense RNA strand, wherein the sense and an antisense RNA strands form an RNA duplex, and wherein the sense RNA strand comprises a nucleotide sequence substantially identical to a target sequence in human Ang2 mRNA, wherein said target sequence consists of SEQ ID NO: 254 or SEQ ID NO: 262, such that the human Ang2 mRNA, is degraded.

7. The method of claim 6, wherein the subject is a human being.

8. The method of claim 6, wherein the siRNA is administered in conjunction with a delivery reagent.

9. The method of claim 8, wherein the delivery agent is selected from the group consisting of lipofectin, lipofectamine, cellfectin, polycations, and liposomes.

10. The method of claim 9, wherein the delivery agent is a liposome.

11. The method claim 10, wherein the liposome comprises a ligand which targets the liposome to cells expressing Ang2.

12. The method of claim 11, wherein the cells are endothelial cells.

13. The method of claim 12, wherein the ligand comprises a monoclonal antibody.

14. The method of claim 10, wherein the liposome is modified with an opsonization-inhibition moiety.

15. The method of claim 14, wherein the opsonization-inhibiting moiety comprises a PEG, PPG, or derivatives thereof.

16. The method of claim 6, wherein the siRNA is expressed from a recombinant plasmid.

17. The method of claim 6, wherein the siRNA is expressed from a recombinant viral vector.

18. The method of claim 17, wherein the recombinant viral vector comprises an adenoviral vector, an adeno-associated viral vector, a lentiviral vector, a retroviral vector, or a herpes virus vector.

19. The method of claim 18, wherein the recombinant viral vector is pseudotyped with surface proteins from vesicular stomatitis virus, rabies virus, Ebola virus, or Mokola virus.

20. The method of claim 17, wherein the recombinant viral vector comprises an adeno-associated viral vector.

21. The method of claim 6, wherein two or more siRNA are administered to the subject, and wherein each siRNA comprises a nucleotide sequence which is substantially identical to a different Ang2 mRNA target sequence.

22. The method of claim 6, wherein two or more siRNA are administered to the subject, and wherein each siRNA administered comprises a nucleotide sequence which is substantially identical to a target sequence from a different target mRNA.

23. The method of claim 6, wherein the siRNA is administered by an enteral administration route.

24. The method of claim 23, wherein the enteral administration route is selected from the group consisting of oral, rectal, and intranasal.

25. The method of claim 6, wherein the siRNA is administered by a parenteral administration route.

26. The method of claim 25, wherein the parenteral administration route is selected from the group consisting of intravascular administration, peri- and intra-tissue administration, subcutaneous injection or deposition, subcutaneous infusion, intraocular administration, and direct application at or near a site of neovascularization.

27. The method of claim 26, wherein the intravascular administration is selected from the group consisting of intravenous bolus injection, intravenous infusion, intra-arterial bolus injection, intra-arterial infusion and catheter instillation into the vasculature.

28. The method of claim 26, wherein the peri- and intra-tissue injection is selected from the group consisting of peri-tumoral injection, intra-tumoral injection, intra-retinal injection, and subretinal injection.

29. The method of claim 26, wherein the intraocular administration comprises intravitreal, intraretinal, subretinal, subtenon, peri- and retro-orbital, trans-corneal or trans-scleral administration.

30. The method of claim 26, wherein the direct application at or near the site of neovascularization comprises application by catheter, corneal pellet, eye dropper, suppository, an implant comprising a porous material, an implant comprising a non-porous material, or an implant comprising a gelatinous material.

31. The method of claim 30, wherein the site of neovascularization is in the eye, and the direct application at or near the site of neovascularization comprises application by eyedropper.

32. The pharmaceutical composition of claim 1, wherein the sense RNA strand comprises one RNA molecule, and the antisense RNA strand comprises one RNA molecule.

33. The pharmaceutical composition of claim 1, wherein the sense and antisense RNA strands forming the RNA duplex are covalently linked by a single-stranded hairpin.

34. The pharmaceutical composition of claim 1, wherein the siRNA further comprises non-nucleotide material.

35. The pharmaceutical composition of claim 1, wherein the siRNA further comprises an addition, deletion, substitution or alteration of one or more nucleotides.

36. The pharmaceutical composition of claim 1, wherein the sense and antisense RNA strands are stabilized against nuclease degradation.

37. The pharmaceutical composition of claim 1, further comprising a 3' overhang.

38. The pharmaceutical composition of claim 37, wherein the 3' overhang comprises from 1 to about 6 nucleotides.

39. The pharmaceutical composition of claim 37, wherein the 3' overhang comprises about 2 nucleotides.

40. The pharmaceutical composition of claim 32, wherein the sense RNA strand comprises a 3' overhang, and the antisense RNA strand comprises a 3' overhang.

41. The pharmaceutical composition of claim 40, wherein the sense and antisense 3' overhangs separately comprise from 1 to about 6 nucleotides.

42. The pharmaceutical composition of claim 41, wherein the sense 3' overhang comprises a dinucleotide and the antisense 3' overhang comprises a dinucleotide.

43. The pharmaceutical composition of claim 42, where the dinucleotide comprising the sense and antisense 3' overhangs is dithymidylic acid (TT) or diuridylic acid (uu).

44. The pharmaceutical composition of claim 37, wherein the 3' overhang is stabilized against nuclease degradation.

45. The pharmaceutical composition of claim 1, wherein the human Ang2 sequence is SEQ ID NO: 2.

46. The pharmaceutical composition of claim 1, wherein the composition is suitable for enteral administration.

47. The pharmaceutical composition of claim 46, wherein the enteral administration is selected from oral administration, rectal administration, and intranasal administration.

48. The pharmaceutical composition of claim 1, wherein the composition is suitable for parenteral administration.

49. The pharmaceutical composition of claim 48, wherein the parenteral administration is selected from intravascular administration, peri-tissue injection, intra-tissue injection, subcutaneous injection, direct application at or near a site of neovascularization, and inhalation.

50. The pharmaceutical composition of claim 49, wherein the intravascular administration is selected from intravenous bolus injection, intravenous infusion, intra-arterial bolus injection, intra-arterial infusion, and catheter installation into the vasculature.

51. The pharmaceutical composition of claim 49, wherein the peri-tissue injection is selected from peri-tumoral injection and subretinal injection.

52. The pharmaceutical composition of claim 49, wherein the intra-tissue injection is selected from intra-tumoral injection and intra-retinal injection.

53. The pharmaceutical composition of claim 49, wherein the direct application is selected from a catheter, retinal pellet, suppository, implant or a pump.

54. A pharmaceutical composition comprising a pharmaceutically acceptable carrier and an effective amount of an siRNA targeting a nucleotide sequence consisting of SEQ ID NO: 2, wherein the siRNA comprises a sense RNA strand and an antisense RNA strand, wherein the sense and an antisense RNA strands form an RNA duplex, and wherein the sense RNA strand comprises a nucleotide sequence substantially identical to a target sequence in human Ang2 mRNA, wherein said target sequence consists of SEQ ID NO: 254 or SEQ ID NO: 262, wherein said effective amount is effective to inhibit the expression of Ang2.

55. A pharmaceutical composition comprising a recombinant plasmid comprising nucleic acid sequences for expressing an siRNA targeting a nucleotide sequence consisting of SEQ ID NO: 2, further comprising a sense RNA strand and an antisense RNA strand, wherein the sense and the antisense RNA strands form an RNA duplex, and wherein the sense RNA strand comprises a nucleotide sequence substantially identical to a target sequence in human Ang2 mRNA, wherein said target sequence consists of SEQ ID NO: 254 or SEQ ID NO: 262, or a physiologically acceptable salt thereof, and wherein the siRNA is expressed in an effective amount when the recombinant plasmid is administered to a subject with a pharmaceutically acceptable carrier, wherein said effective amount is effective to inhibit the expression of Ang2.

56. A pharmaceutical composition comprising a recombinant viral vector comprising nucleic acid sequences for expressing an siRNA targeting a nucleotide sequence consisting of SEQ ID NO: 2, further comprising a sense RNA strand and an antisense RNA strand, wherein the sense and the antisense RNA strands form an RNA duplex, and wherein the sense RNA strand comprises a nucleotide sequence substantially identical to a target sequence in human Ang2 mRNA, wherein said target sequence consists of SEQ ID NO: 254 or SEQ ID NO: 262, wherein the siRNA is expressed in an effective amount when the recombinant viral vector is administered to a subject with a pharmaceutically acceptable carrier, wherein said effective amount is effective to inhibit the expression of Ang2.

57. The pharmaceutical composition of claim 1, wherein said siRNA is naked siRNA.

58. The pharmaceutical composition of claim 1, wherein said target sequence consists of SEQ ID NO: 254.

59. The pharmaceutical composition of claim 1, wherein said target sequence consists of SEQ ID NO: 262.

* * * * *